US010227658B2

(12) United States Patent
Jewell et al.

(10) Patent No.: US 10,227,658 B2
(45) Date of Patent: Mar. 12, 2019

(54) METHODS FOR THE ANALYSIS OF SPITZ TUMOR SAMPLES

(71) Applicant: ABBOTT MOLECULAR INC., Des Plaines, IL (US)

(72) Inventors: Susan Jewell, Elmhurst, IL (US); Ekaterina Pestova, Glenview, IL (US); Gu Li, Lincolnshire, IL (US); Carl Slenk, Gurnee, IL (US); Pedram Gerami, Clarendon Hills, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 37 days.

(21) Appl. No.: 15/354,854

(22) Filed: Nov. 17, 2016

(65) Prior Publication Data

US 2017/0067126 A1 Mar. 9, 2017

Related U.S. Application Data

(62) Division of application No. 13/709,082, filed on Dec. 10, 2012.

(60) Provisional application No. 61/569,245, filed on Dec. 10, 2011.

(51) Int. Cl.
*C12Q 1/6886* (2018.01)
*G01N 33/574* (2006.01)

(52) U.S. Cl.
CPC ......... *C12Q 1/6886* (2013.01); *G01N 33/574* (2013.01); *C12Q 2537/16* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 5,491,224 A | 2/1996 | Bittner et al. |
| 5,756,696 A | 5/1998 | Gray et al. |
| 6,582,908 B2 | 6/2003 | Fodor et al. |
| 2005/0252773 A1 | 11/2005 | McBride et al. |
| 2007/0059747 A1 | 3/2007 | Bastian et al. |
| 2009/0069194 A1 | 3/2009 | Ramakrishnan |
| 2010/0145897 A1 | 6/2010 | Semizarov et al. |

FOREIGN PATENT DOCUMENTS

| WO | WO-9318186 A1 | 9/1993 |
| WO | WO-9617958 A1 | 6/1996 |
| WO | WO-2007028031 A2 | 3/2007 |
| WO | WO-2010051319 A2 | 5/2010 |

OTHER PUBLICATIONS

Gerami, P. Pigment Cell Res. available online Oct. 2011. 24:1015.*
Affymetrix, GeneChip® Human Genome U133 Plus 2.0 Array, P/N 701502 Rev. 5, Copyright @ 2003-2009 Affymetrix, Inc., 2 pages.
Ahern H., "Biochemical, Reagent Kits Offer Scientists Good Return on Investment," The Scientist, 1995, vol. 9 (15), pp. 20-25.
American Cancer Society (ACS), Melanoma, www.cancer.org/docroot/CRI/content/CRI_2_4_1x_What_are_the_key_statistics_for_melanoma_50.asp?sitearea= (2009).
Balch C.M., et al., "Final Version of 2009 AJCC Melanoma Staging and Classification," Journal of Clinical Oncology, 2009, vol. 27 (36), pp. 6199-6206.
Barnhill R.L., et al., "Atypical Spitz Nevi/tumors: Lack of Consensus for Diagnosis, Discrimination from Melanoma, and Prediction of Outcome," Human Pathology, 1999, vol. 30 (5), pp. 513-520.
Bastian B.C., et al., "Chromosomal Gains and Losses in Primary Cutaneous Melanomas Detected by Comparative Genomic Hybridization," Cancer Research, 1998, vol. 58 (10), pp. 2170-2175.
Bastian B.C., et al., "Classifying Melanocytic Tumors Based on Dna Copy Number Changes," The American Journal of Pathology, 2003, vol. 163 (5), pp. 1765-1770.
Bastian B.C., "Molecular Cytogenetics as a Diagnostic Tool for Typing Melanocytic Tumors," Recent Results in Cancer Research, 2002, vol. 160, pp. 92-99.
Busam K.J., et al., "Distinction of Conjunctival Melanocytic Nevi from Melanomas by Fluorescence in Situ Hybridization," Journal of Cutaneous Pathology, 2010, vol. 37 (2), pp. 196-203.
Carter N.P., "Methods and Strategies for Analyzing Copy Number Variation Using DNA Microarrays," Nature Genetics, 2007, vol. 39 (Suppl. 7), pp. S16-S21.
Corona R., et al., "Interobserver Variability on the Histopathologic Diagnosis of Cutaneous Melanoma and Other Pigmented Skin Lesions," Journal of Clinical Oncology, 1996, vol. 14 (4), pp. 1218-1223.
Curtin J.A., et al., "Distinct Sets of Genetic Alterations in Melanoma," The New England Journal of Medicine, 2005, vol. 353 (20), pp. 2135-2147.
Dahabreh I.J., et al., "Somatic EGFR Mutation and Gene Copy Gain as Predictive Biomarkers for Response to Tyrosine Kinase Inhibitors in Non-Small Cell Lung Cancer," Clinical Cancer Research, 2010, vol. 16 (1), pp. 291-303.
Dalton et al., Use of Fluoresecence in Situ Hybridization (FISH) to Distinguish Intranodal Nevus From Metastatic Melanoma, Amer. J. Surg. PathoL, 34(2): 1-15 (2010).
De Klein A., et al., "Multicolor FISH with Improved Sensitivity and Specificity in the Diagnosis of Malignant Melanoma," Expert Review of Molecular Diagnostics, 2012, vol. 12 (7), pp. 683-685.
Gammon B., et al., "Enhanced Detection of Spitzoid Melanomas Using Fluorescence in Situ Hybridization with 9p21 as an Adjunctive Probe," The American Journal of Surgical Pathology, 2012, vol. 36 (1), pp. 81-88.

(Continued)

*Primary Examiner* — Carla J Myers
(74) *Attorney, Agent, or Firm* — Melissa E. Kolom; Casimir Jones, S.C.

(57) ABSTRACT

Methods, probes and kits for diagnosing malignant melanoma and prognosing metastasis thereof in a patient.

1 Claim, 16 Drawing Sheets

(56) References Cited

OTHER PUBLICATIONS

GeneCards GeneAnnot search for CCND1, [retrieved on Jul. 21, 2014]. Retrieved from the Internet:< URL: genecards.weizmann.ac.il/cgi-bin/geneannot/>.
GeneCards GeneAnnot search for CDKN2A, [retrieved on Jul. 21, 2014]. Retrieved from the Internet:< URL: genecards.weizmann.ac.il/cgi-bin/geneannot/>.
GeneCards GeneAnnot search for RREB1, [retrieved on Jul. 21, 2014]. Retrieved from the Internet:< URL: genecards.weizmann.ac.il/cgi-bin/geneannot!>.
Gerami P., et al., "A Highly Specific and Discriminatory FISH Assay for Distinguishing Between Benign and Malignant Melanocytic Neoplasms," The American Journal of Surgical Pathology, 2012, vol. 36 (6), pp. 808-817.
Gerami P., et al., "Copy Number Gains in 11q13 and 8q24 [corrected] are Highly Linked to Prognosis in Cutaneous Malignant Melanoma," Journal of Molecular Diagnostics, 2011, vol. 13 (3), pp. 352-358.
Gerami P., et al., "Copy Number Gains in 11q13 and 8q24 [corrected] are Highly Linked to Prognosis in Cutaneous Malignant Melanoma," The Journal of Molecular Diagnostics, 2011, vol. 13 (3), pp. 352-358.
Gerami P., et al., "Cyclin D1 Homogeneous Staining Regions by Fluorescent in Situ Hybridization: A Possible Indicator of Aggressive Behavior in Melanomas," Archives of Dermatology, 2008, vol. 144 (9), pp. 1235-1236.
Gerami P., et al., "Fluorescence in Situ Hybridization (Fish) as an Ancillary Diagnostic Tool in the Diagnosis of Melanoma," The American Journal of Surgical Pathology, 2009, vol. 33 (8), pp. 1146-1156.
Gerami P., et al., "Fluorescence in Situ Hybridization for Distinguishing Nevoid Melanomas from Mitotically Active Nevi," The American Journal of Surgical Pathology, 2009, vol. 33 (12), pp. 1783-1788.
Herrick J., et al., "Quantifying Single Gene Copy Number By Measuring Fluorescent Probe Lengths on Combed Genomic DNA,"Proceedings of the National Academy of Sciences, 2000, vol. 97 (1), pp. 222-227.
Hodi F.S., et al., "Major Response to Imatinib Mesylate in KIT-Mutated Melanoma," Journal of Clinical Oncology, 2008, vol. 26 (12), pp. 2046-2051.
International Search Report for Application No. PCT/US2012/068653, dated Feb. 22, 2013, 5 pages.
Isaac A.K., et al., "Polyploidy in Spitz Nevi: A not Uncommon Karyotypic Abnormality Identifiable by Fluorescence in Situ Hybridization," The American Journal of Dermatopathology, 2010, vol. 32 (2), pp. 144-148.
Jiang X., et al., "Imatinib Targeting of KIT-Mutant Oncoprotein in Melanoma," Clinical Cancer Research, 2008, vol. 14 (23), pp. 7726-7732.
Kallioniemi A., et al., "Comparative Genomic Hybridization for Molecular Cytogenetic Analysis of Solid Tumors," Science, 1992, vol. 258 (5083), pp. 818-821.
Kallioniemi A., et al., "Detection of Retinoblastoma Gene Copy Number in Metaphase Chromosomes and Interphase Nuclei by Fluorescence in Situ Hybridization," Cytogenetics and Cell Genetics, 1992, vol. 60 (3-4), pp. 190-193.
Kallioniemi O.P., et al., "ERBB2 Amplification in Breast Cancer Analyzed by Fluorescence in Situ Hybridization," Proceedings of the National Academy of Sciences, 1992, vol. 89 (12), pp. 5321-5325.
Kumar J., et al., "Detection of Differential Gene Copy Number Using Denaturing High Performance Liquid Chromatography," Journal of Biochemical and Biophysical Methods, 2005, vol. 64 (3), pp. 226-234.
Liu Z., et al., "Simple Copy Number Determination with Reference Query Pyrosequencing (RQPS)," Cold Spring Harbor Protocols, 2010, vol. 2010 (9), 10 pages.
Lutzky J., et al., "Dose-Dependent, Complete Response to Imatinib of a Metastatic Mucosal Melanoma with a K642E KIT Mutation," Pigment Cell & Melanoma Research, 2008, vol. 21 (4), pp. 492-493.
Maj Scott R. Dalton., et al., "Use of Situ Hybridization Fluorescence to Distinguish Intranodal Metastatic Melanoma," The American Journal of Surgical Pathology, 2010, vol. 34 (2), pp. 1-15.
McGinnis K.S., et al., "Pathology Review of Cases Presenting to a Multidisciplinary Pigmented Lesion Clinic," Archives of Dermatology, 2002, vol. 138 (5), pp. 617-621.
Morrison, L.E. et al., "Labeling Fluorescence in Situ Hybridization Probes for Genomic Targets," Methods in Molecular Biology, 2002, vol. 204, pp. 21-40.
North J.P., et al., "Assessment of Copy Number Status of Chromosomes 6 and 11 by Fish Provides Independent Prognostic Information in Primary Melanoma," The American Journal of Surgical Pathology, 2011, vol. 35 (8), pp. 1146-1150.
Pinkel D., et al., "Fluorescence in Situ Hybridization with Human Chromosome-Specific Libraries: Detection of Trisomy 21 and Translocations of Chromosome 4," Proceedings of the National Academy of Sciences, 1988, vol. 85 (23), pp. 9138-9142.
Pouryazdanparast P., et al., "Distinctive Clinical and Histologic Features in Cutaneous Melanoma with Copy Number Gains in 8q24," The American Journal of Surgical Pathology, 2012, vol. 36 (2), pp. 253-264.
Pouryazdanparast P., et al., "Distinguishing Epithelioid Blue Nevus from Blue Nevus-like Cutaneous Melanoma Metastasis Using Fluorescence in Situ Hybridization," The American Journal of Surgical Pathology, 2009, vol. 33 (9), pp. 1396-1400.
Pouryazdanparast P., et al., "Malignant Melanoma with Monster Cells Showing Massive Cyclin D1 Amplification," The American Journal of Dermatopathology, 2009, vol. 31 (4), pp. 402-403.
Pouryazdanparast P., et al., "The Role of 8q24 Copy Number Gains and c-MYC Expression in Amelanotic Cutaneous Melanoma," Modern Pathology, 2012, vol. 25 (9), pp. 1221-1226.
Rigby P.W., et al., "Labeling Deoxyribonucleic Acid to High Specific Activity in Vitro by Nick Translation with DNA Polymerase I," Journal of Molecular Biology, 1977, vol. 113 (1), pp. 113-237.
Sambrook J., et al., eds., Molecular Cloning: A Laboratory Manual, 3rd Edition, Cold Spring Harbor Laboratory, 2001, Table of Contents.
Schouten J.P., et al. , "Relative Quantification of 40 Nucleic Acid Sequences by Multiplex Ligation-dependent Probe Amplification," Nucleic Acids Research, 2002, vol. 30 (12), pp. e57.
Service R.F., , "Gene Sequencing. The Race for the $1000 Genome," Science, 2006, vol. 311 (5767), pp. 1544-1546.
Shendure J., et al., "Advanced Sequencing Technologies: Methods and Goals," Nature Reviews. Genetics, 2004, vol. 5 (5), pp. 335-344.
Tijssen P., "Overview of Principles of Hybridization and the Strategy of Nucleic Acid Probe Assays, Hybridization with Nucleic Acid Probes" in: Laboratory Techniques in Biochemistry and Molecular Biology, vol. 24, Chapter 2, Van der Vliet P.C., ed., Elsevier Publisher, 1993, pp. 19-78.
Tovey S.M., et al., "Poor Survival Outcomes in HER2-Positive Breast Cancer Patients with Low-Grade, Node-Negative Tumours," British Journal of Cancer, 2009, vol. 100 (5), pp. 680-683.
Viros A., et al., "Improving Melanoma Classification by Integrating Genetic and Morphologic Features," PLOS Medicine, 2008, vol. 5 (6), pp. e120.
Vogelstein B., et al., "Digital PCR," Proceedings of the National Academy of Sciences, 1999, vol. 96 (16), pp. 9236-9241.
Gerami, P. et al., Pigment Cell and Melanoma Research, 2010, 23, 6, p. 952, Abstract No. 215.
European Extended Search Report for Application No. 17165446.0 dated Jun. 21, 2017 (6 pages).
Massi et al., "Atypical Spitzoid melanocytic tumors: Amorphological, mutational, and FISH analysis," Journal of the American Academy of Dermatology, 2011, vol. 64, No. 5, pp. 919-935.
Gaiser et al., "Classifying ambiguous melanocytic lessions with FISH and correlation with clinical long-term follow up," Modern Pathology, 2010, vol. 23, No. 3, pp. 413-419.

(56) References Cited

OTHER PUBLICATIONS

Song et al., "Nevus Versus Melanoma: to FISH, or Not to FISH," Advances in Anatomic Patho, 2011, vol. 18, No. 3, pp. 229-234.
Raskin et al., "Copy Number Variations and Clinical Outcome in Atypical Tumors," American Journal of Surgical Pathol, 2011, vol. 35, No. 2, pp. 243-252.

* cited by examiner

METHODS FOR THE ANALYSIS OF SPITZ TUMOR SAMPLES

CROSS REFERENCE TO RELATED APPLICATIONS

This is a divisional of U.S. patent application Ser. No. 13/709,082, filed on Dec. 10, 2012, which claims priority to U.S. Provisional Patent Application No. 61/569,245, filed on Dec. 10, 2011, the entire contents of all of which are fully incorporated herein by reference.

TECHNICAL FIELD

The present disclosure relates to the diagnosis of malignant melanoma, the prognosis of metastasis of malignant melanoma, the determination of copy numbers of genes and/or regions of chromosomes, and in situ hybridization, as well as sets of one or more probes and kits useful for the diagnosis of malignant melanoma and the prognosis of metastasis thereof.

BACKGROUND

The incidence and mortality rates of melanoma have been increasing over the last few decades (Balch et al., J. Clin. Oncol. 27(36): 6199-6206 (Dec. 20, 2009)). The American Cancer Society (ACS) estimates that the lifetime risk of developing melanoma is approximately 1 in 50 for Caucasians, 1 in 1,000 for African-Americans, and 1 in 200 for Hispanics. Overall, melanoma is the sixth most common cancer in men and the seventh most common cancer in women (American Cancer Society (ACS), Melanoma, cancer.org/docroot/CRI/content/CRI_2 4_1x hd What_are the key_statistics_for_melan oma_50.asp?sitearea=(2009)). In 2009, 68,720 new cases of invasive melanoma, and 8,650deaths were reported in the United States (ACS (2009), supra).

Currently, histology is recognized as the gold standard for the diagnosis of melanoma, and it is, therefore, the current gold standard for predicting clinical behavior. Histology is essentially a surrogate marker for predicting clinical outcome. However, histology is the method of choice by default, and it has not been completely validated. Numerous epidemiologic and clinical studies illustrate the limitations of histology. For example, it is well-recognized that a large percentage of histologically malignant-appearing lesions behave in a benign manner; such lesions are referred to as "indolent melanoma." By contrast, a small percentage of melanomas, which invade the skin to a shallow Breslow's depth, behave in a very malignant and aggressive manner, resulting in metastasis and death.

Sentinel lymph node biopsy is performed in melanoma patients with a high risk for metastases to evaluate the lymph node for metastatic involvement by melanoma. Generally, patients with a melanoma of Breslow's depth greater than about 0.75 mm are biopsied. Such patients have a poor prognosis based on histological factors such as high mitotic rate, ulceration, or Clark's level IV or V. When the sentinel lymph node is involved in melanoma, there is an 80-90% chance that the patient will develop a metastatic disease. Hence, the sentinel lymph node status is the strongest prognostic indicator of melanoma. Those patients in whom the sentinel lymph node is not involved in melanoma are considered to be a cohort of patients with significantly better prognosis compared to those patients in whom the sentinel lymph node is involved in melanoma.

Although the number of melanoma cancer-related deaths continues to increase and the treatment of advanced melanoma continues to show dismal results, there have been several breakthroughs in the past decade. These breakthroughs include the stratification of melanoma into molecular subtypes, which correlate to prognosis (Viros et al., PLoS Med 5(6): e120 (Jun. 3, 2008)), as well as targeted therapy, which can be tailored to the specific activated oncogenic pathway (Hodi et al., J. Clin. Oncol. 26(12): 2046-2051 (Apr. 20, 2008); and Jiang et al., Clin. Cancer Res. 14(23): 7726-7732 (Dec. 1, 2008)). For example, specific targeted inhibitors, such as BRAF inhibitors or CKIT inhibitors, such as imatinib mesylate, have been successfully used to treat patients with advanced melanoma (Hodi et al. (2008), supra; and Lutzky et al., Pigment Cell Melanoma Res. 21(4): 492-493 (August 2008)). Hence, identifying specific oncogenic pathways in melanoma can help stratify melanoma patients prognostically and can help predict therapeutic results.

In addition to somatic mutations, copy number aberrations through gain of specific oncogenes or loss of specific tumor suppressor genes are highly characteristic of melanoma. The genomic classification of malignant melanoma based on patterns of gene copy number alterations has been proposed; such classification reportedly would enable rational patient selection for treatment (U.S. Pat. App. Pub. No. 2010/0145897 and Int'l Pat. App. Pub. No. WO 2010/051319). Comparative genomic hybridization (CGH) studies show that 95% of melanomas have chromosomal copy number aberrations (Bastian et al., Cancer Res. 58(10): 2170-2175 (May 15, 1998)). Frequent chromosomal copy number losses include deletions at 9p (82%), 10q (63%), 6q (28%), and 8p (22%). Frequent copy number gains may occur at 7q (50%), 8q (34%), 6p (28%), and 1q (25%), among others (Bastian et al. (1998), supra). Melanomas on acral sites reportedly have significantly more aberrations involving chromosomes 5p, 11q, 12q, and 15, as well as focused gene amplifications (Bastian et al., Amer. J. Path. 163: 1765-1770 (2003)). An algorithm using signal counts from a combination of four fluorescent in situ hybridization (FISH) probes targeting chromosome 6p25, 6 centromere, 6q23, and 11q13 provides the highest diagnostic discrimination between melanomas and nevi with 86.7% sensitivity and 95.4% specificity (Gerami et al., Am. J. Surgical Path. 33: 1146-1156 (2009)); see, also, Gerami et al., Arch. Dermatol. 144(9): 1235-1236 (September 2008), and Pouryazdanparast et al., Amer. J. Dermatopathol. 31(4): 402-403 (June 2009)). Melanomas with wild-type BRAF or N-RAS reportedly have frequent increases in the number of copies of the genes for cyclin-dependent kinase 4 (CDK4) and cyclin D1 (CCND1) (Curtin et al., New England J. of Med. 353: 2135-2147 (Nov. 17, 2005)). A small subset of Spitz nevi reportedly shows an isolated gain of the short arm of chromosome 11p, which has not been observed in melanomas (Bastian, Recent Results Cancer Res. 160: 92-99 (2002); and Bastian et al. (2003), supra). However, while copy number gains have been linked to diagnosis of melanoma, to date there has been no linkage to prognosis. The ability to relate genetic alterations to prognosis of melanoma would help to improve prognostication and management of patients with conventional therapies and could help identification of therapeutic targets.

Copy number gains of specific oncogenes have been linked to prognosis in a number of cancers. For example, amplification of Her-2/neu has been associated with poor prognosis in breast cancers (Tovey et al., Br. J. Cancer 100(5): 680-683 (Mar. 10, 2009)), while elevated copy numbers of the epidermal growth factor receptor (EGFR) gene are highly associated with likely response and survival benefit of non-small cell lung cancer treated with EGFR tyrosine kinase inhibitors (Dahabreh et al., Clin. Cancer Res. 16(1): 291-303 (Jan. 1, 2010)).

The present disclosure seeks to provide a method for prognosing malignant melanoma, including atypical Spitz tumors, in a patient. This and other objects and advantages, as well as additional features, will become apparent from the detailed description provided herein.

In addition to the foregoing, the present disclosure seeks to provide a method for diagnosing malignant melanoma in a patient. It is well-accepted among pathologists that there are several subsets of melanocytic tumors that can be difficult to classify clearly as either benign or malignant (Barnhill et al., Hum. Pathol. 30(5): 513-520 (1999); Corona et al., J. Clin. Oncol. 14(4): 1218-1223 (1996); and McGinnis et al., Arch. Dermatol. 138(5): 617-621 (2002)). In many cases the differential diagnosis includes an entirely benign lesion, such as a spitz nevus, as opposed to a highly lethal, malignant lesion, such as melanoma with spitzoid morphological features. Given the development of new biological therapies for melanoma, it is desirable to be able to distinguish malignant and benign lesions. Added advantages of differential diagnosis include the avoidance of undue psychological burden resulting from an incorrect diagnosis, the determination of appropriate surgical management with or without sentinel lymph node biopsy, and the determination of appropriate systemic therapy.

In addition to conventional microscopy, molecular diagnostic techniques are emerging and are showing promise as diagnostic aids. A four-probe fluorescence in situ hybridization (FISH) assay targeting 6p25 (RREB1), 6q23 (MYB), Cep6 (centromere 6), and 11q13 (CCND1) has been shown to distinguish hisologically unequivocal melanomas from benign nevi with a sensitivity of 86.7% and a specificity of 95.4% (Gerami et al., Am. J. Surg. Pathol. 33(8):1146-56 (2009)). When this probe set and the predetermined criteria were applied to a set of ambiguous melanocytic neoplasms with known follow-up, there was a significant difference in the results among the group with metastasis (6/6 positive) versus the group with no metastasis (6/21 positive). The p-value showing the difference in likelihood of a positive result in the metastasis versus the non-metastasis group was highly significant, i.e., less than 0.003 by Fisher's exact test. The foregoing probe set was also helpful in distinguishing nevoid melanoma from mitotically active nevi (Gerami et al., Am. J. Surg. Pathol. 33(12): 1783-1788 (2009)), blue nevus-like metastasis from epithelioid blue nevus (Pouryazdanparast et al., Am. J. Surg. Pathol. 33(9): 1396-400 (2009)), and conjunctival melanoma from conjunctival nevi (Busam et al., J. Cutan. Pathol. 37(2): 196-203 (2010)). However, a separate analysis of a series of spitzoid melanomas showed a sensitivity of 70% in this subset of lesions (Gammon et al., Am. J. Surg. Pathol., "Enhanced Detection of Spitzoid Melanomas Using Fluorescence In Situ Hybridization With 9p21 as an Adjunctive Probe" (Epub ahead of print, Oct. 10, 2011)). Hence, while the development of the above-described probe set was a significant advancement in molecular diagnosis of melanocytic neoplasms, there is room for improvement in the sensitivity of the assay, particularly for spitzoid melanomas. While the above-described probe set is relatively highly specific, the presence of tetraploid cells in spitzoid neoplasms can occasionally cause difficulty in interpreting the results of the FISH (Isaac et al., Am. J. Dermatopathol. 32(2): 144-148 (2010)). Other objects and advantages of the method for diagnosing malignant melanoma in a patient, as well as additional features, will become apparent from the detailed description provided herein.

SUMMARY

A method of prognosing metastasis of malignant melanoma in a patient is provided. The method comprises determining in a sample of malignant melanoma obtained from the patient (i) (a) and/or (b), (ii) (c) and/or (d), (iii) (a) and/or (d), or (iv) (b) and/or (c), wherein:

(a) is a copy number ratio of CCND1/control centromere or a copy number of CCND1, wherein a copy number ratio of CCND1/control centromere greater than about 1.55 per cell or a copy number of CCND1 greater than about 2.81 per cell indicates that metastasis will likely occur, (b) is a copy number of MYC, wherein a copy number of MYC greater than about 2.48 per cell indicates that metastasis will likely occur, (c) is a percentage of cells having a gain of CCND1/control centromere or a percentage of cells having a gain of CCND1, wherein a percentage of cells of greater than or equal to about 30% having a gain of CCND1 or a percentage of cells of greater than or equal to about 54% having a gain of CCND1/control centromere indicates that metastasis will likely occur, and (d) is a percentage of cells having a gain of MYC, wherein a percentage of cells of greater than about 20% having a gain of MYC indicates that metastasis will likely occur.

A method of prognosing metastasis of malignant melanoma in a patient having a melanoma with a Breslow's depth less than about 1 mm is also provided. The method comprises determining in a sample of malignant melanoma obtained from the patient a copy number ratio of CCND1/control centromere and a copy number of MYC. A copy number ratio of CCND1/control centromere greater than about 1.55 per cell or a copy number of MYC greater than about 2.48 per cell indicates that metastasis will likely occur.

Also provided is a method of prognosing metastasis of malignant melanoma in a patient having a melanoma with a Breslow's depth less than or equal to 2 mm. The method comprises determining in a sample of malignant melanoma obtained from the patient a copy number ratio of CCND1/control centromere and a copy number of MYC. A copy number ratio of CCND1/control centromere greater than about 1.38 per cell and a copy number of MYC greater than about 2.36 per cell indicates that metastasis will likely occur.

Further provided is a method of prognosing metastasis of malignant melanoma in a patient having a melanoma with a Breslow's depth greater than or equal to 1 mm but less than about 4 mm. The method comprises determining in a sample of malignant melanoma obtained from the patient a copy number ratio of CCND1/control centromere. A copy number ratio of CCND1/control centromere greater than about 1.55 per cell indicates that metastasis will likely occur. The method can further comprise detecting in the patient a copy number of MYC, wherein a copy number of MYC greater than about 2.60 per cell also indicates that metastasis will likely occur.

Still further provided is a method of prognosing metastasis of malignant melanoma in a patient having melanoma with a Breslow's depth greater than about 2.0 mm. The method comprises determining in a sample of malignant melanoma obtained from the patient a copy number ratio of CCND1/control centromere or a copy number of MYC. A copy number ratio of CCND1/control centromere greater than about 1.55 per cell indicates that metastasis will likely occur. A copy number of MYC greater than about 2.22 per cell indicates that metastasis will likely occur.

The above methods can comprise determining the copy number ratio of CCND1/control centromere and/or the copy number of MYC by in situ hybridization. The in situ hybridization can be fluorescent in situ hybridization (FISH).

Also in view of the above, a kit comprising (a) a set of one or more probes that enables prognosis of metastasis of malignant melanoma in a patient and (b) instructions for prognosing metastasis of malignant melanoma in the patient is provided. The set of one or more probes comprises (i') a probe for CCND1, alone or in further combination with a probe for a control centromere, and/or (ii') a probe for MYC. The instructions can comprise determining in a sample of malignant melanoma obtained from the patient (i) (a) and/or (b), (ii) (c) and/or (d), (iii) (a) and/or (d), or (iv) (b) and/or (c), wherein:

(a) is a copy number ratio of CCND1/control centromere or a copy number of CCND1, wherein a copy number ratio of CCND1/control centromere greater than about 1.55 per cell or a copy number of CCND1 greater than about 2.81 per cell indicates that metastasis will likely occur, (b) is a copy number of MYC, wherein a copy number of MYC greater than about 2.48 per cell indicates that metastasis will likely occur, (c) is a percentage of cells having a gain of CCND1/control centromere or a percentage of cells having a gain of CCND1, wherein a percentage of cells of greater than or equal to about 30% having a gain of CCND1 or a percentage of cells of greater than or equal to about 54% having a gain of CCND1/control centromere indicates that metastasis will likely occur, and (d) is a percentage of cells having a gain of MYC, wherein a percentage of cells of greater than about 20% having a gain of MYC indicates that metastasis will likely occur.

A method of diagnosing malignant melanoma in a patient is also provided. The method comprises determining in a number of nuclei in a diagnostic sample, which comprises nucleated cells, obtained from the patient a copy number of RREB1, a copy number of MYC, a copy number of CCND1, and a copy number of CDKN2A, wherein an increase in the copy number of RREB1, an increase in the copy number of MYC, an increase in the copy number of CCND1, and a decrease in the copy number of CDKN2A indicates that the sample comprises a malignant melanoma. The number of nuclei can be about 30, wherein, when increases in copy numbers of RREB1, MYC, and CCND1 and a homozygous deletion of CDKN2A are detected in greater than or equal to 27% of the nuclei, the sample comprises a malignant melanoma. Alternatively, the number of nuclei can be about 30, wherein, when increases in copy numbers of RREB1, MYC, and CCND1 and a homozygous deletion of CDKN2A are detected in greater than or equal to 8 nuclei, the sample comprises a malignant melanoma.

Further provided is a set of probes that enables diagnosis and prognosis of malignant melanoma. The set comprises a probe for RREB1, a probe for MYC, a probe for CCND1, and a probe for CDKN2A.

Still further provided is a kit. The kit comprises (a) a set of probes that enables diagnosis and prognosis of malignant melanoma in a patient, wherein the set of probes comprises a probe for RREB1, a probe for MYC, a probe for CCND1, and a probe for CDKN2A, and (b) instructions for diagnosing malignant melanoma in the patient, wherein the instructions comprise determining in a diagnostic sample obtained from the patient a copy number of RREB1, a copy number of MYC, a copy number of CCND1, and a copy number of CDKN2A, wherein an increase in the copy number of RREB1, an increase in the copy number of MYC, an increase in the copy number of CCND1, and a decrease in the copy number of CDKN2A indicates that the patient has malignant melanoma, and/or instructions for prognosing metastasis of malignant melanoma in the patient, wherein the instructions comprise determining in a sample of malignant melanoma obtained from the patient a copy number of RREB1, a copy number of MYC, a copy number of CCND1, and a copy number of CDKN2A, wherein an increase in the copy number of RREB1, an increase in the copy number of MYC, an increase in the copy number of CCND1, and a decrease in the copy number of CDKN2A indicates that metastasis will likely occur.

Also provided is a method of prognosing metastasis of malignant melanoma in a patient. The method comprises determining in a number of nuclei in a sample, which comprises nucleated cells, obtained from the patient a copy number of RREB1, a copy number of MYC or ZNF217, a copy number of CCND1, and a copy number of CDKN2A, wherein an increase in the copy number of RREB1, an increase in the copy number of MYC or ZNF217, an increase in the copy number of CCND1, and a decrease in the copy number of CDKN2A indicates that metastasis will likely occur. The number of nuclei can be about 30, wherein, when increases in copy numbers of RREB1, MYC or ZNF217, and CCND1 and a homozygous deletion of CDKN2A are detected in greater than or equal to 27% of the nuclei, metastasis will likely occur. Alternatively, the number of nuclei can be about 30, wherein, when increases in copy numbers of RREB1, MYC or ZNF217, and CCND1 and a homozygous deletion of CDKN2A are detected in greater than or equal to 8 nuclei, metastasis will likely occur.

A set of probes that enables prognosis of metastasis of malignant melanoma is also provided. The set comprises a probe for RREB1, a probe for MYC or ZNF217, a probe for CCND1, and a probe for CDKN2A.

A kit is also provided. The kit comprises (a) a set of probes that enables prognosis of metastasis of malignant melanoma in a patient, wherein the set of probes comprises a probe for RREB1, a probe for MYC or ZNF217, a probe for CCND1, and a probe for CDKN2A, and (b) instructions for prognosing malignant melanoma in the patient, wherein the instructions comprise determining in a sample obtained from the patient a copy number of RREB1, a copy number of MYC or ZNF217, a copy number of CCND1, and a copy number of CDKN2A, wherein an increase in the copy number of RREB11, an increase in the copy number of MYC or ZNF217, an increase in the copy number of CCND1, and a decrease in the copy number of CDKN2A indicates that metastasis will likely occur.

Additionally, a method of prognosing metastasis of atypical Spitz tumor in a patient is provided. The method comprises determining in a sample of tumor from the patient a copy number of RREB1, CCND1, and/or CDKN2A, wherein an increase in copy number of RREB1 or an increase in copy number of CCND1 or a homozygous deletion of CDKN2A indicates that aggressive metastasis will likely occur and homozygous deletion of CDKN2A indicates that even more aggressive metastasis will likely occur.

In this regard, further provided is a set of probes that enables prognosis of metastasis of atypical Spitz tumor. The set comprises a probe for RREB1, a probe for CCND1, and a probe for CDKN2A.

Still further provided is a kit. The kit comprises (a) a set of probes that enables prognosis of metastasis of atypical Spitz tumor in a patient, wherein the set of probes comprises a probe for RREB1, a probe for CCND1, and a probe for CDKN2A, and (b) instructions for prognosing metastasis of atypical Spitz tumor in the patient, wherein the instructions comprise determining in a sample of tumor from the patient a copy number of RREB1, CCND1, and/or CDKN2A, wherein an increase in copy number of RREB1 or an increase in copy number of CCND1 or a homozygous deletion of CDKN2A indicates that aggressive metastasis will likely occur and homozygous deletion of CDKN2A indicates that even more aggressive metastasis will likely occur.

DETAILED DESCRIPTION

Figure 1A:
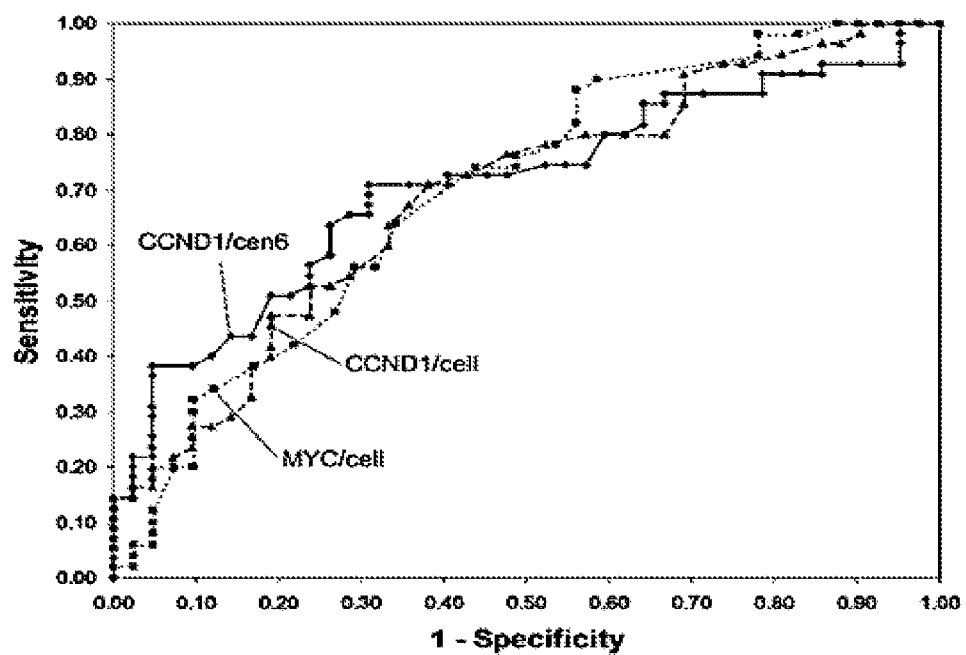
FIG. 1a is a graph of sensitivity vs. 1-specificity for CCND1/chromosome 6, CCND1/cell, and MYC/cell.
Figure 1B:
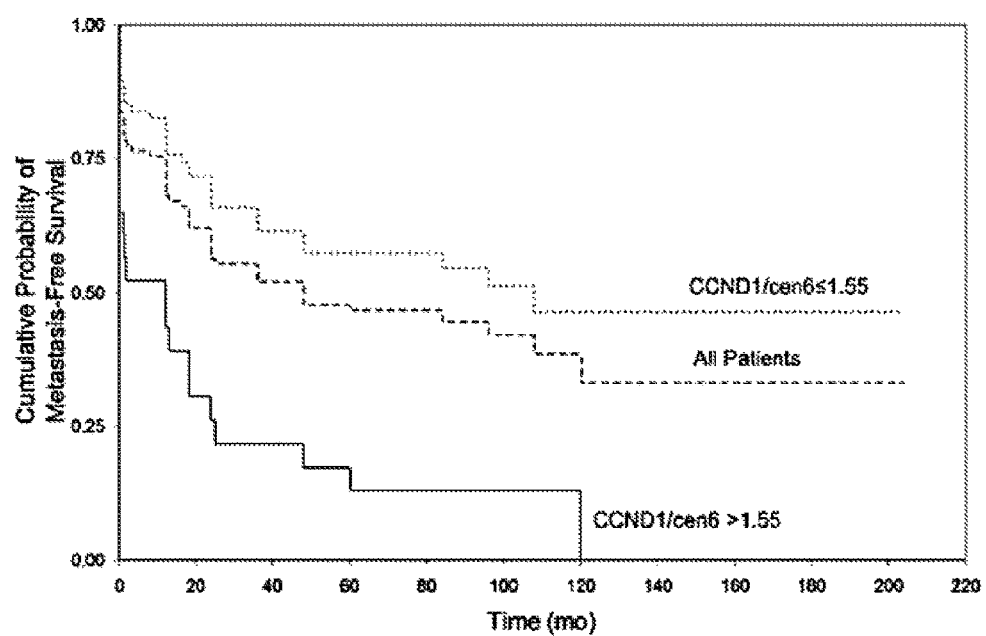
FIG. 1b is a graph of the cumulative probability of metastasis-free survival vs. time (months) for CCND1/chromosome 6≤1.55, all patients, and CCND1/chromosome 6>1.55.
Figure 1C:
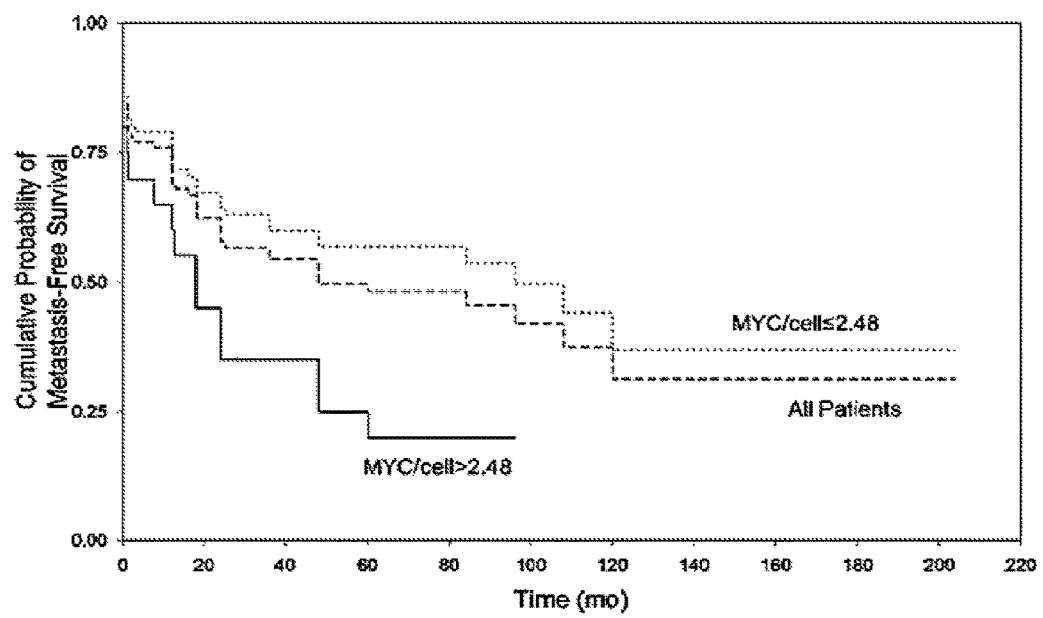
FIG. 1c is a graph of the cumulative probability of metastasis-free survival vs. time (months) for MYC/cell≤2.48, all patients, and MYC/cell>2.48.
Figure 1D:
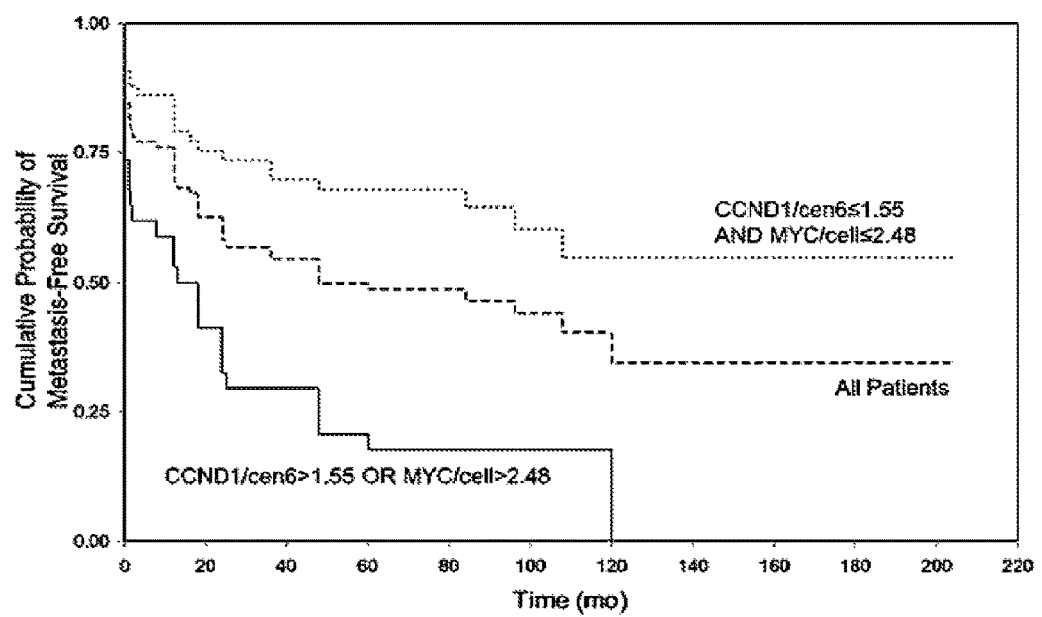
FIG. 1d is a graph of the cumulative probability of metastasis-free survival vs. time (months) for CCND1/chromosome 6≤1.55 and MYC/cell≤2.48, all patients, and CCND1/chromosome 6≤1.55 or MYC/cell>2.48.

The present disclosure is based on the surprising and unexpected discovery that a prognosis for malignant melanoma in a patient can be made based on (i) a determination of the copy number ratio of CCND1/control centromere or the copy number of CCND1 and/or the copy number of MYC in a sample of malignant melanoma obtained from the patient or (ii) a determination of the percentage of cells having a gain of CCND1/control centromere or the percentage of cells having a gain of CCND1 and/or the percentage of cells having a gain of MYC. By comparing (i) the copy number ratio of CCND1/control centromere to a predetermined cutoff and/or the copy number of MYC to a predetermined cutoff or (ii) the percentage of cells having a gain of CCND1 to a predetermined cutoff and/or the percentage of cells having a gain of MYC to a predetermined cutoff, the likelihood of metastasis occurring in the patient can be prognosticated. In view of the foregoing, the present disclosure provides methods of prognosing disease progression, such as metastasis of malignant melanoma, in a patient, a set of one or more probes that enables prognosis of disease progression, such as metastasis of malignant melanoma, and a kit comprising a set of one or more such probes and instructions for prognosing disease progression, such as metastasis of malignant melanoma, in a patient.

The present disclosure is also based on the surprising and unexpected discovery that a diagnosis of malignant melanoma in a patient can be made based on a determination of the copy numbers of RREB1, MYC, a copy number of CCND1, and a copy number of CDKN2A. In view of the foregoing, the present disclosure provides a method of diagnosing malignant melanoma in a patient, a set of probes that enables diagnosis of malignant melanoma, and a kit comprising a set of such probes and instructions for diagnosing melanoma in a patient. The method can be used to classify better histologically ambiguous melanocytic tumors and to identify more selectively those histologically ambiguous melanocytic tumors with the greatest likelihood of resulting in distant metastasis or death of a patient. In this regard, the method also can be used to prognosticate disease progression, such as metastasis of malignant melanoma.

Thus, the present disclosure is also based on the discovery that a prognosis of metastasis of malignant melanoma in a patient can be made based on a determination of the copy numbers of RREB1, MYC or ZNF217, a copy number of CCND1, and a copy number of CDKN2A. In this regard, the present disclosure provides a method of prognosing metastasis of malignant melanoma in a patient, a set of probes that enables prognosis of metastasis of malignant melanoma, and a kit comprising a set of such probes and instructions for prognosing metastasis of malignant melanoma.

The following terms are relevant to the present disclosure:

"About" refers to approximately a +/−10% variation from the stated value. It is to be understood that such a variation is always included in any given value provided herein, whether or not specific reference is made to it.

"Breslow's depth" is considered to be one of the three most important prognostic factors of melanoma. The other factors are T stage and ulceration. Breslow's depth is determined by using an ocular micrometer at a right angle to the skin. The depth from the granular layer of the epidermis to the deepest point of invasion to which tumor cells have invaded the skin is directly measured.

"Cancer diagnosis" generally refers to an identification of a type of cancer. The diagnosis can be differential in nature, e.g., distinguishing histologically ambiguous malanocytic tumors, such as a nevoid melanoma from mitotically active nevi, a blue nevus-like metastasis from an epithelioid blue nevus, or a conjunctival melanoma from a conjunctival nevus.

"Cancer prognosis" generally refers to a forecast or prediction of the probable course (e.g., disease progression) or outcome (e.g., metastasis or death) of the cancer. As used herein, cancer prognosis includes the forecast or the prediction of the progression of melanoma, including the metastasis of malignant melanoma and death.

"Chromosome enumeration probe (CEP)" is any probe that enables the number of specific chromosomes in a cell to be enumerated. A chromosome enumeration probe typically recognizes and binds to a region near to (referred to as "peri-centromeric") or at the centromere of a specific chromosome, typically a repetitive DNA sequence (e.g., alpha satellite DNA). The centromere of a chromosome is typically considered to represent that chromosome, since the centromere is required for faithful segregation during cell division. Deletion or amplification of a particular chromosomal region can be differentiated from loss or gain of the whole chromosome (aneusomy), within which it normally resides, by comparing the number of signals corresponding to the particular locus (copy number) to the number of signals corresponding to the centromere. One method for making this comparison is to divide the number of signals representing the locus by the number of signals representing the centromere. Ratios of less than one indicate relative loss or deletion of the locus, and ratios greater than one indicate relative gain or amplification of the locus. Similarly, comparison can be made between two different loci on the same chromosome, for example on two different arms of the chromosome, to indicate imbalanced gains or losses within the chromosome. In lieu of a centromeric probe for a chromosome, one of skill in the art will recognize that a chromosomal arm probe may alternately be used to approximate whole chromosomal loss or gain. However, such probes are not as accurate at enumerating chromosomes, since the loss of signals for such probes may not always indicate a loss of the entire chromosome. Examples of chromosome enumeration probes include CEP® probes commercially available from Abbott Molecular, Inc., Des Plaines, Ill. (formerly Vysis, Inc., Downers Grove, Ill.).

"Clark's level" is a measure of the layers of skin involved in a melanoma. For example, level I involves the epidermis. Level II involves the epidermis and upper dermis. Level III involves the epidermis, upper dermis, and lower dermis. Level IV involves the epidermis, upper dermis, lower dermis, and subcutis.

"Copy number" is a measurement of DNA, whether of a single locus, one or more loci, or an entire genome. A "copy number" of two is "wild-type" in a human (because of diploidy, except for sex chromosomes). A "copy number" of other than two in a human (except for sex chromosomes) deviates from wild-type. Such deviations include amplifications, i.e., increases in copy numbers, and deletions, i.e., decreases in copy numbers and even the absence of copy numbers.

"Fixatives" include, but are not limited to, alcohol solutions, acid acetone solutions, aldehydes (such as formaldehyde, paraformaldehyde, and glutaraldehyde), methanol/acetic acid, and formalin.

"Labeled," "labeled with a detectable label," and "detectably labeled" are used interchangeably herein to indicate that an entity (e.g., a probe) can be detected. "Label" and "detectable label" mean a moiety attached to an entity to render the entity detectable, such as a moiety attached to a probe to render the probe detectable upon binding to a target sequence. The moiety, itself, may not be detectable but may become detectable upon reaction with yet another moiety. Use of the term "detectably labeled" is intended to encompass such labeling. The detectable label can be selected such that the label generates a signal, which can be measured and the intensity of which is proportional to the amount of bound entity. A wide variety of systems for labeling and/or detecting molecules, such as nucleic acids, e.g., probes, are well-known. Labeled nucleic acids can be prepared by incorporating or conjugating a label that is directly or indirectly detectable by spectroscopic, photochemical, biochemical, immunochemical, electrical, optical, chemical or other means. Suitable detectable labels include radioisotopes, fluorophores, chromophores, chemiluminescent agents, microparticles, enzymes, magnetic particles, electron dense particles, mass labels, spin labels, haptens, and the like. Fluorophores and chemiluminescent agents are preferred herein.

"Locus-specific probe" refers to a probe that selectively binds to a specific locus in a region on a chromosome, e.g., a locus that has been determined to undergo gain/loss in metastasis. A probe can target coding or non-coding regions, or both, including exons, introns, and/or regulatory sequences, such as promoter sequences and the like.

"Nucleic acid sample" refers to a sample comprising nucleic acid in a form suitable for hybridization with a probe, such as a sample comprising nuclei or nucleic acids isolated or purified from such nuclei. The nucleic acid sample may comprise total or partial (e.g., particular chromosome(s)) genomic DNA, total or partial mRNA (e.g., particular chromosome(s) or gene(s)), or selected sequence(s). Condensed chromosomes (such as are present in interphase or metaphase) are suitable for use as targets in in situ hybridization, such as FISH.

"Percentage gain" and "% gain" refer generally to the percentage of cells having an increased number of copies a particular gene, whereas "percentage loss" and "% loss" refer generally to the percentage of cells having a decreased number of copies of a particular gene. For example, a normal or wild-type cell contains two copies of each gene. The percentage gain/loss can be determined as follows:

(number of cells with increased or decreased number of copies of gene/total number of cells)×100=% gain/loss.

"Predetermined cutoff" and "predetermined level" refer generally to a cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). The present disclosure provides exemplary predetermined levels for prognosing metastasis in patients with malignant melanoma. While cutoff values may vary with the manner of assay, the correlations as described herein should remain generally applicable.

"Probe," in the context of the present disclosure, is an oligonucleotide or polynucleotide that can selectively hybridize to at least a portion of a target sequence (e.g., the gene CCND1, the gene MYC, or the centromere of chromosome 6, such as the alpha satellite DNA located at the centromere of chromosome 6) under conditions that allow for or promote selective hybridization. In general, a probe can be complementary to the coding or sense (+) strand of DNA or complementary to the non-coding or anti-sense (−) strand of DNA (sometimes referred to as "reverse-complementary"). Probes can vary significantly in length. A length of about 10 to about 100 nucleotides, such as about 15 to about 75 nucleotides, e.g., about 15 to about 50 nucleotides, can be preferred.

"Section" of a tissue sample is a single part or piece of a tissue sample, e.g., a thin slice of tissue or cells cut from a tissue sample. Two or more sections of tissue samples may be taken and analyzed. If desired, a single section can be analyzed at various levels, e.g., morphological and molecular (e.g., nucleic acid and protein).

"Selectively hybridize to" (as well as "selective hybridization," specifically hybridize to," and "specific hybridization"), in the context of the present disclosure, refers to the binding, duplexing, or hybridizing of a nucleic acid molecule preferentially to a particular nucleotide sequence under stringent conditions. The term "stringent conditions" refers to conditions under which a probe will hybridize preferentially to its target sequence, and to a lesser extent to, or not at all to, other non-target sequences. A "stringent hybridization" and "stringent hybridization wash conditions" in the context of nucleic acid hybridization (e.g., as in array, Southern hybridization, Northern hybridization, or FISH) are sequence-dependent, and differ under different conditions. An extensive guide to the hybridization of nucleic acids is found in, e.g., Tijssen, *Laboratory Techniques in Biochemistry and Molecular Biology—Hybridization with Nucleic Acid Probes*, Part I, Ch. 2, "Overview of principles of hybridization and the strategy of nucleic acid probe assays," Elsevier, NY (1993) ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids, which have more than 100 complementary residues, on an array or on a filter in a Southern or Northern blot is 42° C. using standard hybridization solutions (see, e.g., Sambrook and Russell, *Molecular Cloning: A Laboratory Manual*, 3rd ed., Vol. 1-3, Cold Spring Harbor Laboratory, Cold Spring Harbor Press, NY (2001)).

"Target sequence," "target region," and "nucleic acid target" refer to a nucleotide sequence that resides at a specific chromosomal location whose loss and/or gain is being determined.

The terminology used herein is for the purpose of describing particular embodiments only and is not otherwise intended to be limiting.

Methods of Diagnosing Malignant Melanoma and Prognosing Metastasis of Malignant Melanoma In view of the above, a method of prognosing metastasis of malignant melanoma in a patient is provided. The method comprises determining in a sample of malignant melanoma obtained from the patient (i) (a) and/or (b), (ii) (c) and/or (d), (iii) (a) and/or (d), or (iv) (b) and/or (c), wherein:

(a) is a copy number ratio of CCND1/control centromere or a copy number of CCND1, wherein a copy number ratio of CCND1/control centromere greater than about 1.55 per cell or a copy number of CCND1 greater than about 2.81 per cell indicates that metastasis will likely occur, (b) is a copy number of MYC, wherein a copy number of MYC greater than about 2.48 per cell indicates that metastasis will likely occur, (c) is a percentage of cells having a gain of CCND1/control centromere or a percentage of cells having a gain of CCND1, wherein a percentage of cells of greater than or equal to about 30% having a gain of CCND1 or a percentage of cells of greater than or equal to about 54% having a gain of CCND1/control centromere indicates that metastasis will likely occur, and (d) is a percentage of cells having a gain of MYC, wherein a percentage of cells of greater than about 20% having a gain of MYC indicates that metastasis will likely occur.

A method of prognosing metastasis of malignant melanoma in a patient having a melanoma with a Breslow's depth less than about 1 mm, such as less than 1 mm, is also provided. The method comprises determining in a sample of malignant melanoma obtained from the patient a copy number ratio of CCND1/control centromere and a copy number of MYC. A copy number ratio of CCND1/control centromere greater than about 1.55, such as greater than 1.55, and a copy number of MYC greater than about 2.48, such as greater than 2.48, indicates that metastasis will likely occur.

Also provided is a method of prognosing metastasis of malignant melanoma in a patient having a melanoma with a Breslow's depth less than or equal to 2 mm. The method comprises determining in a sample of malignant melanoma obtained from the patient a copy number ratio of CCND1/control centromere and a copy number of MYC. A copy number ratio of CCND1/control centromere greater than about 1.38, such as greater than 1.38, and a copy number of MYC greater than about 2.36, such as greater than 2.36, indicates that metastasis will likely occur.

Further provided is a method of prognosing metastasis of malignant melanoma in a patient having a melanoma with a Breslow's depth greater than or equal to 1 mm but less than about 4 mm, such as less than about 4 mm. The method comprises determining in a sample of malignant melanoma obtained from the patient a copy number ratio of CCND1/control centromere. A copy number ratio of CCND1/control centromere greater than about 1.55, such as greater than 1.55, indicates that metastasis will likely occur. The method can further comprise determining in a sample of malignant melanoma obtained from the patient a copy number of MYC, wherein a copy number of MYC greater than about 2.60, such as greater than 2.60, also indicates that metastasis will likely occur.

Still further provided is a method of prognosing metastasis of malignant melanoma in a patient having melanoma with a Breslow's depth greater than about 2.0 mm, such as greater than 2.0 mm. The method comprises determining in a sample of malignant melanoma obtained from the patient a copy number ratio of CCND1/control centromere or a copy number of MYC. A copy number ratio of CCND1/control centromere greater than about 1.55, such as greater than 1.55, indicates that metastasis will likely occur. A copy number of MYC greater than about 2.22, such as greater than 2.22, indicates that metastasis will likely occur.

Even still further provided is a method of diagnosing malignant melanoma in a patient. The method comprises determining in a number of nuclei in a diagnostic sample, which comprises nucleated cells, obtained from the patient a copy number of RREB1, a copy number of MYC, a copy number of CCND1, and a copy number of CDKN2A, wherein an increase in the copy number of RREB1, an increase in the copy number of MYC, an increase in the copy number of CCND1, and a decrease in the copy number of CDKN2A indicates that the sample comprises a malignant melanoma. The diagnostic sample can comprise cells, which comprise nuclei, wherein the copy number of RREB1, the copy number of MYC, the copy number of CCND1, and the copy number of CDKN2A are determined in a number of nuclei. The number of nuclei can be about 30, wherein, when increases in copy numbers of RREB1, MYC, and CCND1 and a homozygous deletion of CDKN2A are detected in greater than or equal to 27% of the nuclei, the sample comprises a malignant melanoma. Alternatively, the number of nuclei can be about 30, wherein, when increases in copy numbers of RREB1, MYC, and CCND1 and a homozygous deletion of CDKN2A are detected in greater than or equal to 8 nuclei, the sample comprises a malignant melanoma.

Still further provided is a method of prognosing metastasis of malignant melanoma, which do not involve a characterization of Breslow's depth. The method comprises determining in a number of nuclei in a sample, which comprises nucleated cells, obtained from the patient a copy number of RREB1, a copy number of MYC or ZNF217, a copy number of CCND1, and a copy number of CDKN2A, wherein an increase in the copy number of RREB1, an increase in the copy number of MYC or ZNF217, an increase in the copy number of CCND1, and a decrease in the copy number of CDKN2A indicates that metastasis will likely occur. The sample can comprise cells, which comprise nuclei, wherein the copy number of RREB1, the copy number of MYC or ZNF217, the copy number of CCND1, and the copy number of CDKN2A are determined in a number of nuclei. The number of nuclei can be about 30, wherein, when increases in copy numbers of RREB1, MYC or ZNF217, and CCND1 and a homozygous deletion of CDKN2A are detected in greater than or equal to 27% of the nuclei, metastasis will likely occur. Alternatively, the number of nuclei can be about 30, wherein, when increases in copy numbers of RREB1, MYC or ZNF217, and CCND1 and a homozygous deletion of CDKN2A are detected in greater than or equal to 8 nuclei, metastasis will likely occur.

Even still further provided is a method of prognosing metastasis of atypical Spitz tumor in a patient. The method comprises determining in a sample of tumor from the patient a copy number of RREB1, CCND1, and/or CDKN2A, wherein an increase in copy number of RREB1 or an increase in copy number of CCND1 or a homozygous deletion of CDKN2A indicates that aggressive metastasis will likely occur and homozygous deletion of CDKN2A indicates that even more aggressive metastasis will likely occur.

The above prognostic methods, which involve a characterization of Breslow's depth, can comprise determining the copy number ratio of CCND1/control centromere and/or the copy number of MYC by in situ hybridization, in which each probe is detectably labeled and, when two or more probes are hybridized simultaneously or sequentially to the same sample, each probe is detectably labeled with a distinct label. The in situ hybridization can be fluorescent in situ hybridization (FISH), in which each probe is detectably labeled and, when two or more probes are hybridized simultaneously or sequentially to the same sample, each probe is detectably labeled with a distinct fluorophore. The copy number of the CCND1 gene can be determined by using the probe Vysis Locus Specific Identifier (LSI) CCND1. The copy number of a control centromere can be determined by using a probe that hybridizes to the alpha satellite DNA located at the centromere of a chromosome. This probe functions as a control, thereby enabling accounting of differences in efficiency of hybridization between samples as necessary. An example of a probe that hybridizes to the alpha satellite DNA located at the centromere of a chromosome is a Chromosome Enumerator Probe (Cep). A probe that hybridizes to the alpha satellite DNA located at the centromere of chromosome 1, 2, 3, 4, 5, 6, 7, 8, 9, 10, 11, 12, 13, 14, 15, 16, 17, 18, 19, 20, 21, or 22 can be used. A preferred control centromere probe is one that hybridizes to the alpha satellite DNA of chromosome 11, such as Cep11. The copy number of MYC can be determined by using the probe Vysis LSI MYC.

The above diagnostic methods can comprise determining the copy numbers of RREB1, MYC, CCND1, and CDKN2A by in situ hybridization, in which each probe is detectably labeled and, when two or more probes are hybridized simultaneously or sequentially to the same sample, each probe is detectably labeled with a distinct label. The in situ hybridization can be fluorescent in situ hybridization (FISH), in which each probe is detectably labeled and, when two or more probes are hybridized simultaneously or sequentially to the same sample, each probe is detectably labeled with a distinct fluorophore. The copy number of the RREB1 gene can be determined by using the probe Vysis LSI RREB1. The copy number of the MYC gene can be determined by using the probe Vysis LSI MYC. The copy number of the CCND1 gene can be determined by using the probe Vysis LSI CCND1. The copy number of the CDKN2A gene can be determined by using the probe Vysis LSI CDKN2A.

The above prognostic methods, which do not involve a characterization of Breslow's depth, can comprise determining the copy numbers of RREB1, MYC or ZNF217, CCND1, and CDKN2A by in situ hybridization, in which each probe is detectably labeled and, when two or more probes are hybridized simultaneously or sequentially to the same sample, each probe is detectably labeled with a distinct label. The in situ hybridization can be fluorescent in situ hybridization (FISH), in which each probe is detectably labeled and, when two or more probes are hybridized simultaneously or sequentially to the same sample, each probe is detectably labeled with a distinct fluorophore. The copy number of the RREB1 gene can be determined by using the probe Vysis LSI RREB1. The copy number of the MYC gene can be determined by using the probe Vysis LSI MYC. The copy number of the ZNF217 gene can be determined using the probe Vysis LSI ZNF217. The copy number of the CCND1 gene can be determined by using the probe Vysis LSI CCND1. The copy number of the CDKN2A gene can be determined by using the probe Vysis LSI CDKN2A.

With regard to all of the above methods, the nature/size of the probe will depend, at least in part, on the method used to determine a particular parameter, e.g., copy number, copy number ratio, or percentage gain of a gene of interest. When an above diagnostic/prognostic method is carried out by in situ hybridization, such as FISH, for example, the probe can be relatively large. When an above diagnostic/prognostic method is carried by another method, the probe can be smaller, even substantially smaller, than the probe used for in situ hybridization, such as FISH, in which case the probe preferably hybridizes to a sequence within the gene of interest.

In view of the above, a probe for detecting a parameter involving CCND1, such as the copy number of CCND1, a copy number ratio involving CCND1, or the percentage gain of CCND1, by in situ hybridization, such as FISH, preferably hybridizes to the 11q13 region of chromosome 11, which comprises the CCND1 gene. The probe also can hybridize to an adjacent region, such as the STS (sequence-tagged site) marker D11S1076, which is located on the centromeric side, the FGF4 gene, which is located on the telomeric side, or both of D11S1076 and FGF4. A probe for detecting a parameter involving CCND1 by another method can be smaller, even substantially smaller, than the probe used for in situ hybridization, such as FISH, in which case the probe preferably hybridizes to a sequence within the CCND1 gene (sequence information is available online from sources such as GenBank and GeneCards®). "CCND1" is used herein to refer to any and all probes that can be used to determine a parameter involving CCND1, whether copy number, copy number ratio, percentage gain, and the like, irrespective of the particular method used to determine the parameter.

Likewise, a probe for detecting a parameter involving MYC, such as the copy number of MYC, a copy number ratio involving MYC, or the percentage gain of MYC, by in situ hybridization, such as FISH, preferably hybridizes to the 8q24 region of chromosome 8, which comprises the MYC gene. The probe also can hybridize to an adjacent region located on the centromeric side of 8q24, an adjacent region located on the telomeric side of 8q24, or both. A preferred probe covers approximately 820 kb, such as 821 kb, of 8q24 and is centered on the MYC gene. A probe for detecting a parameter involving MYC by another method can be smaller, even substantially smaller, than the probe used for in situ hybridization, such as FISH, in which case the probe preferably hybridizes to a sequence within the MYC gene (sequence information is available online from sources such as GenBank and GeneCards®). "MYC" is used herein to refer to any and all probes that can be used to determine a parameter involving MYC, whether copy number, copy number ratio, percentage gain, and the like, irrespective of the particular method used to determine the parameter.

Likewise, a probe for detecting a parameter involving CDKN2A, such as the copy number of CDKN2A, a copy number ratio involving CDKN2A, or the percentage gain of CDKN2A, by in situ hybridization, such as FISH, preferably hybridizes to the 9p21 region of chromosome 9, which comprises the CDKN2A gene. The probe also can hybridize to an adjacent region, such as the STS marker D9S1749, which is located on the centromeric side of 9p21, and the STS marker D9S1752, which is located on the telomeric side, or both of D9S1749 and D9S1752. A preferred probe covers approximately 190 kb of 9p21. A probe for detecting a parameter involving CDKN2A by another method can be smaller, even substantially smaller, than the probe used for in situ hybridization, such as FISH, in which case the probe preferably hybridizes to a sequence within the CDKN2A gene (sequence information is available online from sources such as GenBank and GeneCards®). "CDKN2A" is used herein to refer to any and all probes that can be used to determine a parameter involving CDKN2A, whether copy number, copy number ratio, percentage gain, and the like, irrespective of the particular method used to determine the parameter.

Likewise, a probe for detecting a parameter involving RREB1, such as the copy number of RREB1, a copy number ratio involving RREB1, or the percentage gain of RREB1, by in situ hybridization, such as FISH, preferably hybridizes to the 6q25 region of chromosome 6, which comprises the RREB1 gene. The probe also can hybridize to an adjacent region, such as the STS marker SHGC-140278, which is located on the centromeric side, and the STS marker RH61070, which is located on the telomeric side, or both of SHGC-140278 and RH61070. A probe for detecting a parameter involving RREB1 by another method can be smaller, even substantially smaller, than the probe used for in situ hybridization, such as FISH, in which case the probe preferably hybridizes to a sequence within the RREB1 gene (sequence information is available online from sources such as GenBank and GeneCards®). "RREB1" is used herein to refer to any and all probes that can be used to determine a parameter involving RREB1, whether copy number, copy number ratio, percentage gain, and the like, irrespective of the particular method used to determine the parameter.

Likewise, a probe for detecting a parameter involving ZNF217, such as the copy number of ZNF217, a copy number ratio involving ZNF217, or the percentage gain of ZNF217, by in situ hybridization, such as FISH, preferably hybridizes to the 20q13 region of chromosome 20, which comprises the ZNF217 gene. The probe also can hybridize to an adjacent region, such as the STS marker RI-29727, which is located on the centromeric side, and the STS marker SHGC-83153, which is located on the telomeric side, or both of RI-29727 and SHGC-83153. A probe for detecting a parameter involving ZNF217 by another method can be smaller, even substantially smaller, than the probe used for in situ hybridization, such as FISH, in which case the probe preferably hybridizes to a sequence within the ZNF217 gene (sequence information is available online from sources such as GenBank and GeneCards®). "ZNF217" is used herein to refer to any and all probes that can be used to determine a parameter involving ZNF217, whether copy number, copy number ratio, percentage gain, and the like, irrespective of the particular method used to determine the parameter.

When the above methods are carried out by in situ hybridization, in which each probe is detectably (and distinctly, if more than one probe is used simultaneously or sequentially on the same sample) labeled, such as by FISH, in which each probe is detectably (and distinctly, if more than one probe is used simultaneously or sequentially on the same sample) labeled with a fluorophore, the methods are typically carried out on a sample of a melanoma, which is fresh (fresh cells can be cultured for 1-3 days and a blocker, such as Colcemid, can be added to the culture to block the cells in metaphase, during which chromosomes are highly condensed and can be visualized), frozen, or fixed (e.g., fixed in formalin and embedded in paraffin), treated (e.g., with RNase and pepsin) to increase accessibility of target nucleic acid (e.g., DNA) and reduce non-specific binding, and then subjected to hybridization with one or more probes, washing to remove any unbound probes, and detection of hybridized probes. For example, a cell suspension can be applied as a single layer onto a slide, and the cell density can be measured by a light or phase contrast microscope. A section (approximately 5 μm in thickness) of a formalin-fixed, paraffin-embedded sample of melanoma can be mounted onto a slide, such as a SuperFrost Plus positively charged slide (available from ThermoShandon, Pittsburgh, Pa.), baked at 56° C. overnight, de-paraffinized, submerged in 1× saline sodium citrate, pH 6.3, at 80° C. for 35 minutes, and washed in water for three minutes. After protease digestion (4 mg pepsin/mL and 0.2 N HCl) at 37° C. for 15 minutes, the section can be rinsed in water for three minutes, passed through graded ethanol, and dried. Preferably, hybridization with one or more probes as described above is carried out at 37° C. for 16-18 hours in an automated co-denaturation oven (HYBrite or ThermoBrite Denaturation/Hybridization System, Abbot Molecular, Inc., Des Plaines, Ill.) according to the manufacturer's instructions (such methods typically involve denaturation of probes and target nucleic acids). After hybridization, the section is preferably placed in washing buffer (2× saline sodium citrate/0.3% NP40; available from Abbott Molecular, Inc.) at room temperature for 2-10 minutes to remove the coverslip and then immersed in 73 OC washing buffer for two minutes, dried, and mounted with 4'6'-diamidino-2-phenylindole dihydrochloride hydrate (DAPI) I antifade solution (Abbott Molecular, Inc.). Preferably, the slide is analyzed with an epi-fluorescence microscope equipped with single band-pass filters (Abbott Molecular, Inc.).

Prior to detection, cell samples may be optionally pre-selected based on apparent cytologic abnormalities. Pre-selection identifies suspicious cells, thereby allowing the screening to be focused on those cells. Pre-selection allows for faster screening and increases the likelihood that a positive result will not be missed. During pre-selection, cells from a biological sample can be placed on a microscope slide and visually scanned for cytologic abnormalities commonly associated with dysplastic and neoplastic cells. Such abnormalities include abnormalities in nuclear size, nuclear shape, and nuclear staining, as assessed by counterstaining nuclei with nucleic acid stains or dyes such as propidium iodide or 4,6-diamidino-2-phenylindole dihydrochloride (DAPI) usually following hybridization of probes to their target DNAs. Typically, neoplastic cells harbor nuclei that are enlarged, irregular in shape, and/or show a mottled staining pattern. Propidium iodide, typically used at a concentration of about 0.4 μg/ml to about 5 μg/ml, is a red-fluorescing DNA-specific dye that can be observed at an emission peak wavelength of 614 nm. DAPI, typically used at a concentration of about 125 ng/ml to about 1,000 ng/ml, is a blue fluorescing DNA-specific stain that can be observed at an emission peak wavelength of 452 nm with a DAPI filter at low magnification. In this case, only those cells pre-selected for detection are subjected to counting for chromosomal losses and/or gains. Preferably, pre-selected cells on the order of at least 20, and more preferably at least 30-40, in number are chosen for assessing chromosomal losses and/or gains.

Alternatively, a tumor-bearing area can be localized using the DAPI filter at low magnification and thoroughly inspected for the presence of nuclei harboring abnormal copy numbers of any probe. In a normal cell, two copies of a given probe will be detected. In an abnormal cell, more or less copies of a given probe will be detected. Areas with the most significant copy number changes are preferably selected for enumeration. Wherever possible, three abnormal areas are selected and, within each abnormal area, 10 random nuclei are analyzed under high power (64× or 100× objective). Preferably, nuclei are non-overlapping and harbor sufficiently bright signals.

Alternatively, cells for detection may be chosen independent of cytologic or histologic features. For example, all non-overlapping cells in a given area or areas on a microscope slide may be assessed for chromosomal losses and/or gains. As a further example, cells on the slide, e.g., cells that show altered morphology, on the order of at least about 50, and more preferably at least about 100, in number that appear in consecutive order on a microscope slide may be chosen for assessing chromosomal losses and/or gains.

For prognostic methods, such as those involving characterization of Breslow's depth, the copies of CCND1, alone or in further combination with the copies of a control centromere, are counted, and the copy number of CCND1 is determined or the ratio of CCND1/control centromere is determined. Alternatively or additionally, the copies of MYC are counted. The (i) copy number of CCND1 or the copy number ratio of CCND1/control centromere and/or (ii) the copy number of MYC is/are then compared to the appropriate predetermined cutoff(s) set forth herein. A copy number of CCND1 or a copy number ratio of CCND1/control centromere greater than the predetermined cutoff indicates that metastasis will likely occur. Similarly, a copy number of MYC greater than the predetermined cutoff indicates that metastasis will likely occur.

Alternatively, for prognostic methods, such as those involving characterization of Breslow's depth, the copies of CCND1, alone or in further combination with the copies of a control centromere, are counted and the percentage of cells having a gain of CCND1 or the percentage of cells having a gain of CCND1/control centromere is/are determined. Alternatively or additionally, the percentage of cells having a gain of MYC is determined. The percentage of cells having a gain of CCND1 or the percentage of cells having a gain of CCND1/control centromere is then compared to the appropriate predetermined cutoff(s) as set forth herein. A percentage of cells having a gain of CCND1/control centromere or a percentage of cells having a gain of CCND1 greater than the predetermined cutoff indicates that metastasis will likely occur. Similarly, a percentage of cells having a gain of MYC greater than the predetermined cutoff indicates that metastasis will likely occur.

For the diagnostic methods, the copies of RREB1, MYC, CCND1, and CDKN2A are counted. An increase in the copy number of RREB1, an increase in the copy number of MYC, an increase in the copy number of CCND1, and a decrease in the copy number of CDKN2A indicates that the sample comprises a malignant melanoma. The diagnostic sample can comprise cells, which comprise nuclei, wherein the copy number of RREB1, the copy number of MYC, the copy number of CCND1, and the copy number of CDKN2A are determined in a number of nuclei. The number of nuclei can be about 30, wherein, when increases in copy numbers of RREB1, MYC, and CCND1 and a homozygous deletion of CDKN2A are detected in greater than or equal to 27% of the nuclei, the sample comprises a malignant melanoma. Alternatively, the number of nuclei can be about 30, wherein, when increases in copy numbers of RREB1, MYC, and CCND1 and a homozygous deletion of CDKN2A are detected in greater than or equal to 8 nuclei, the sample comprises a malignant melanoma.

For other prognostic methods, such as those not involving characterization of Breslow's depth, the copies of RREB11, MYC or ZNF217, CCND1, and CDKN2A are counted. An increase in the copy number of RREB1, an increase in the copy number of MYC or ZNF217, an increase in the copy number of CCND1, and a decrease in the copy number of CDKN2A indicates that the sample comprises a malignant melanoma. The diagnostic sample can comprise cells, which comprise nuclei, wherein the copy number of RREB1, the copy number of MYC or ZNF217, the copy number of CCND1, and the copy number of CDKN2A are determined in a number of nuclei. The number of nuclei can be about 30, wherein, when increases in copy numbers of RREB1, MYC or ZNF217, and CCND1 and a homozygous deletion of CDKN2A are detected in greater than or equal to 27% of the nuclei, metastasis is likely to occur. Alternatively, the number of nuclei can be about 30, wherein, when increases in copy numbers of RREB1, MYC or ZNF217, and CCND1 and a homozygous deletion of CDKN2A are detected in greater than or equal to 8 nuclei, metastasis is likely to occur.

Thus, such methods comprise contacting a sample of malignant melanoma from a patient, e.g., a nucleic acid sample, with at least one probe that binds selectively to a target nucleic acid sequence (i.e., for prognostic methods, such as those involving characterization of Breslow's depth, CCND1, alone or in further combination with a control centromere, and, alternatively or additionally, and simultaneously or sequentially, in either order, MYC; for diagnostic methods, RREB1, MYC, CCND1, and CDKN2A; and, for other prognostic methods, such as those not involving characterization of Breslow's depth, RREB1, MYC or ZNF217, CCND1, and CDKN2A) under conditions that allow (or promote) the probe to bind selectively with its target nucleic acid sequence and form a stable hybridization complex. Such methods further comprise detecting the formation of the hybridization complex and counting the number of hybridization complexes.

In view of the number of hybridization complexes comprising CCND1, alone or in further combination with the number of hybridization complexes comprising the control centromere, the prognostic methods further comprise determining the copy number of CCND1 or the copy number ratio of CCND1/control centromere and comparing the copy number or the copy number ratio to the appropriate predetermined cutoff, wherein a copy number of a copy number ratio greater than the appropriate predetermined cutoff indicates that metastasis will likely occur. In view of the number of hybridization complexes comprising MYC, the prognostic methods further comprise determining the copy number of MYC and comparing the copy number to the predetermined cutoff, wherein a copy number greater than the predetermined cutoff indicates that metastasis will likely occur.

Also in view of the number of hybridization complexes comprising CCND1, alone or in further combination with the number of hybridization complexes comprising the control centromere, alternatively the prognostic methods further comprise determining the percentage of cells having a gain of CCND1 or CCND1/control centromere and comparing the percentage of cells having a gain to the appropriate predetermined cutoff, wherein a percentage of cells having a gain greater than the appropriate predetermined cutoff indicates that metastasis will likely occur. In view of the number of hybridization complexes comprising MYC, the prognostic methods further comprise determining the percentage of cells having a gain of MYC and comparing the percentage of cells having a gain to the predetermined cutoff, wherein a percentage of cells having a gain greater than the appropriate predetermined cutoff indicates that metastasis will likely occur.

In view of the number of hybridization complexes comprising RREB1, MYC, CCND1, and CDKN2A, the diagnostic methods further comprise determining the copy numbers of RREB1, MYC, CCND1, and CDKN2A, wherein an increase in the copy numbers of RREB1, MYC, CCND1, and a decrease in the copy number of CDKN2A indicates that the sample comprises malignant melanoma. In view of the number of hybridization complexes comprising RREB1, MYC or ZNF217, CCND1, and CDKN2A, the prognostic methods, which do not involve characterization of Breslow's depth, further comprise determining the copy numbers of RREB1, MYC or ZNF217, CCND1, and CDKN2A, wherein an increase in the copy numbers of RREB1, MYC or ZNF217, CCND1, and a decrease in the copy number of CDKN2A indicates that metastasis will likely occur.

While the above methods are preferred, it is possible to determine a copy number of a gene or a copy number ratio (e.g., of two genes, of two chromosomes, or of a gene and a chromosome) in accordance with other methods already known in the art or currently under development. Such methods may necessitate the use of a sample of malignant melanoma that is other than a section of a malignant melanoma that is fixed in formalin and embedded in paraffin, e.g., a fresh or frozen section of a malignant melanoma, homogenized cells from a malignant melanoma, lysed cells from a malignant melanoma, or isolated or purified nucleic acids (e.g., a "nucleic acid sample" such as DNA) from a malignant melanoma ("sample of malignant melanoma" as used herein is intended to encompass all forms of a sample of malignant melanoma that enable the determination of the copy number ratio). In this regard, a touch preparation (a monolayer of cells obtained by pressing fresh or frozen tissue against a slide) prepared from an uncultured primary tumor can be used (see, e.g., Kallioniemi et al., Cytogenet. Cell Genet. 60: 190-193 (1992)). Touch preparations contain intact nuclei and do not suffer from the truncation artifact of sectioning. The monolayer of cells in a touch preparation may be fixed, e.g., in alcohol, such as ethanol, or alcoholic solution, such as 3:1 methanol:acetic acid. Nuclei also can be extracted from thick sections of paraffin-embedded specimens to reduce truncation artifacts and eliminate extraneous embedded material. Typically, biological samples, once obtained, are harvested and processed prior to hybridization using standard methods known in the art. Such processing typically includes protease treatment and additional fixation in an aldehyde solution, such as formaldehyde.

Examples of methods that can be used herein include, but are not limited to, quantitative polymerase chain reaction (Q-PCR), real-time Q-PCR (Applied Biosystems, Foster City, Calif.), densitometric scanning of PCR products, digital PCR, optionally with pre-amplification of the gene(s) and/or chromosomal region(s) for which copy number(s) is/are to be determined (see, e.g., Vogelstein et al., PNAS USA 96: 9236-9241 (1999); U.S. Pat. App. Pub. No. 2005/0252773; and U.S. Pat. App. Pub. No. 2009/0069194), comparative genomic hybridization (CGH; see, e.g., Kallioniemi et al., Science 258: 818-821 (1992); and Int'l Pat. App. Pub. No. WO 93/18186), microsatellite or Southern allelotype analysis, dot blots, arrays, microarrays (Carter, Nature Genetics Supplement 39: S16-S21 (July 2007)), multiplex amplifiable probe hybridization (MAPH), multiplex ligation-dependent probe amplification (MLPA; see, e.g., Schouten et al., Nucleic Acids Res. 30: e 57 (2002)), denaturing high performance liquid chromatography (dHPLC; Kumar et al., J. Biochem. Biophys. Methods 64(3): 226-234 (2005)), dynamic allele-specific hybridization (DASH), measuring fluorescent probe lengths on combed genomic DNA (Herrick et al., PNAS 97(1): 222-227 (2000)), reference query pyrosequencing (RQPS; Liu et al., Cold Spring Harb. Protoc. doi: 10.1101/pdb.prot5491 (2010)), mapping of fosmid ends onto a reference sequence (capillary-based technology), microelectrophoretic and nanopore sequencing (see, e.g., Service, Science 311: 1544-1546 (2006); and Shendure et al., Nat. Rev. Genet. 5: 335-344 (2004)), and the like.

Denaturation of nucleic acid targets for analysis by in situ hybridization and similar methods typically is done in such a manner as to preserve cell morphology. For example, chromosomal DNA can be denatured by high pH, heat (e.g., temperatures from about 70-95° C.), organic solvents (e.g., formamide), and combinations thereof. Probes, on the other hand, can be denatured by heat in a matter of minutes.

After denaturation, hybridization is carried out. Conditions for specifically hybridizing the probes to their nucleic acid targets generally include the combinations of conditions that are employable in a given hybridization procedure to produce specific hybrids, the conditions of which may easily be determined by one of ordinary skill in the art. Such conditions typically involve controlled temperature, liquid phase, and contact between a probe and a target. Hybridization conditions vary depending upon many factors including probe concentration, target length, target and probe G-C content, solvent composition, temperature, and duration of incubation. At least one denaturation step may precede contact of the probes with the targets. Alternatively, the probe and the target may be subjected to denaturing conditions together while in contact with one another, or with subsequent contact of the probe with the biological sample. Hybridization may be achieved with subsequent incubation of the probe/sample in, for example, a liquid phase of about a 50:50 volume ratio mixture of 2-4×SSC and formamide, at a temperature in the range of about 25 to about 55° C. for a time that is illustratively in the range of about 0.5 to about 96 hours, or more preferably at a temperature of about 32 to about 40° C. for a time in the range of about 2 to about 16 hours. In order to increase specificity, use of a blocking agent, such as unlabeled blocking nucleic acid, as described in U.S. Pat. No. 5,756,696 (the contents of which are herein incorporated by reference in their entirety, and specifically for the description of the use of blocking nucleic acid), may be used. Other conditions may be readily employed for specifically hybridizing the probes to their nucleic acid targets present in the sample, as would be readily apparent to one of skill in the art. Hybridization protocols are described, for example, in Pinket et al., PNAS USA 85: 9138-9142 (1988); *In situ Hybridization Protocols*, Methods in Molecular Biology, Vol. 33, Choo, ed., Humana Press, Totowa, N.J. (1994); and Kallioniemi et al., PNAS USA 89: 5321-5325 (1992).

Upon completion of a suitable incubation period, non-specific binding of chromosomal probes to sample DNA may be removed by a series of washes. Temperature and salt concentrations are suitably chosen for a desired stringency. The level of stringency required depends on the complexity of a specific probe sequence in relation to the genomic sequence, and may be determined by systematically hybridizing probes to samples of known genetic composition. In general, high stringency washes may be carried out at a temperature in the range of about 65 to about 80° C. with about 0.2× to about 2×SSC and about 0.1% to about 1% of a non-ionic detergent such as Nonidet P-40 (NP40). If lower stringency washes are required, the washes may be carried out at a lower temperature with an increased concentration of salt.

When fluorophore-labeled probes or probe compositions are used, the detection method can involve fluorescence microscopy, flow cytometry, or other means for determining probe hybridization. Any suitable microscopic imaging method may be used in conjunction with the methods described herein for observing multiple fluorophores. In the case where fluorescence microscopy is employed, hybridized samples may be viewed under light suitable for excitation of each fluorophore and with the use of an appropriate filter or filters. Automated digital imaging systems such as the MetaSystems, BioView or Applied Imaging systems may alternatively be used.

Depending on the method employed, a digital image analysis system can be used to facilitate the display of results and to improve the sensitivity of detecting small differences in fluorescence intensity. An exemplary system is QUIPS (an acronym for quantitative image processing system), which is an automated image analysis system based on a standard fluorescence microscope equipped with an automated stage, focus control and filter wheel (Ludl Electronic Products, Ltd., Hawthorne, N.Y.). The filter wheel is mounted in the fluorescence excitation path of the microscope for selection of the excitation wavelength. Special filters (Chroma Technology, Brattleboro, Vt.) in the dichroic block allow excitation of the multiple dyes without image registration shift. The microscope has two camera ports, one of which has an intensified CCD camera (Quantex Corp., Sunnyvale, Calif.) for sensitive high-speed video image display which is used for finding interesting areas on a slide as well as for focusing. The other camera port has a cooled CCD camera (model 200 by Photometrics Ltd., Tucson, Ariz.), which is used for the actual image acquisition at high resolution and sensitivity. The cooled CCD camera is interfaced to a SUN 4/330 workstation (SUN Microsystems, Inc., Mountain View, Calif.) through a VME bus. The entire acquisition of multicolor images is controlled using an image processing software package SCIL-Image (Delft Centre for Image Processing, Delft, Netherlands).

In array CGH (aCGH) the probes are immobilized at distinct locations on a substrate and are not labeled (see, e.g., Int'l Pat. App. Pub. No. WO 96/17958). Instead, sample nucleic acids, which comprise target nucleic acid(s), are labeled. Either the sample nucleic acids are labeled prior to hybridization or the hybridization complexes are detectably labeled. In dual- or multi-color aCGH the probe array is simultaneously or sequentially hybridized to two or more collections of differently labeled target nucleic acids.

Probes

In view of the above, a set of one or more probes that enables prognosis of metastasis of malignant melanoma is provided. The set comprises, or consists of, (a) a probe for CCND1, along or in further combination with a probe for a control centromere, and/or (b) a probe for MYC. The probe for CCND1 can be Vysis LSI CCND1. The probe for a control centromere hybridizes to the alpha satellite DNA located at the centromere of a chromosome. An example of a probe for a control centromere is a Chromosome Enumerator Probe (Cep). This probe functions as a control, thereby enabling accounting of differences in efficiency of hybridization between samples as necessary. A probe that hybridizes to the alpha satellite DNA located at the centromere of chromosome 1, 2, 3, 4, 5, 6, 7, 8, 9, 10, 11, 12, 13, 14, 15, 16, 17, 18, 19, 20, 21, or 22 can be used. A preferred control centromere probe is one that hybridizes to the alpha satellite DNA of chromosome 11, such as Cep11. The probe for MYC can be Vysis LSI MYC.

Further in view of the above, a set of probes that enables diagnosis and prognosis of malignant melanoma is provided. The set comprises, or consists of, a probe for RREB1, a probe for MYC, a probe for CCND1, and a probe for CDKN2A. The probe for RREB1 can be Vysis LSI RREB1. The probe for MYC can be Vysis LSI MYC. The probe for CCND1 can be Vysis LSI CCND1. The probe for CDKN2A can be Vysis LSI CDKN2A.

Still further in view of the above, a set of probes that enables prognosis of metastasis of malignant melanoma is provided. The set comprises, or consists of, a probe for RREB1, a probe for MYC or ZNF217, a probe for CCND1, and a probe for CDKN2A. The probe for RREB1 can be Vysis LSI RREB1. The probe for MYC can be Vysis LSI MYC. The probe for ZNF217 can be Vysis LSI ZNF217. The probe for CCND1 can be Vysis LSI CCND1. The probe for CDKN2A can be Vysis LSI CDKN2A.

Even still further in view of the above, a set of probes that enables prognosis of metastasis of atypical Spitz tumor is provided. The set comprises, or consists of, a probe for RREB1, a probe for CCND1, and a probe for CDKN2A. The probe for RREB1 can be Vysis LSI RREB1. The probe for CCND1 can be Vysis LSI CCND1. The probe for CDKN2A can be Vysis LSI CDKN2A.

Chromosome enumerator probes (CEP) and locus-specific probes that target a chromosome region or sub-region can be obtained commercially or readily prepared by those in the art. Such probes can be commercially obtained from Abbott Molecular, Inc. (Des Plaines, Ill.), Molecular Probes, Inc. (Eugene, Oreg.), or Cytocell (Oxfordshire, UK). Chromosomal probes can be prepared, for example, from protein nucleic acids (PNA), cloned human DNA such as plasmids, bacterial artificial chromosomes (BACs), and P1 artificial chromosomes (PACs) that contain inserts of human DNA sequences. A region of interest can be obtained via PCR amplification or cloning. Alternatively, chromosomal probes can be prepared synthetically in accordance with methods known in the art.

When targeting of a particular gene locus is desired, probes that hybridize along the entire length of the targeted gene can be preferred, although not required. A locus-specific probe can be designed to hybridize to an oncogene or tumor suppressor gene, the genetic aberration of which is correlated with metastasis, e.g., CCND1 or MYC.

Preferably, probes are detectably labeled, and, when two or more probes are used simultaneously or sequentially on the same sample, each probe is distinctly labeled. Preferably, the probes are detectably labeled with fluorophores, and, when two or more probes are used simultaneously or sequentially on the same sample, each probe is distinctly labeled. Examples of preferred fluorophores include, but are not limited to, 7-amino-4-methylcoumarin-3-acetic acid (AMCA), 5-carboxy-X-rhodamine, 6-carboxy-X-rhodamine, lissamine rhodamine B, 5-carboxyfluorescein, 6-carboxyfluorescein, fluorescein-5-isothiocyanate (FITC), 7-diethylaminocoumarin-3-carboxylic acid, tetramethylrhodamine-5-isothiocyanate, tetramethylrhodamine-6-isothiocyanate, 5-carboxyltetramethylrhodamine, 6-carboxytetramethylrhodamine, 7-hydroxycoumarin-3-carboxylic acid, N-4,4-difluoro-5,7-dimethy-4-bora-3a,4a-diaza-3-indacenepropionic acid, eosin-5-isothiocyanate, erythrosine-5-isothiocyanate, SpectrumRed (Abbott Molecular, Inc.), SpectrumGold (Abbott Molecular, Inc.), SpectrumGreen (Abbott Molecular, Inc.), SpectrumAqua (Abbott Molecular, Inc.), TEXAS RED (Molecular Probes, Inc.), and CASCADE blue acetylazide (Molecular Probes, Inc.). The particular label used is not critical; desirably, however, the particular label does not interfere with in situ hybridization of the probe. The label desirably is detectable in as low copy number as possible to maximize the sensitivity of the assay and be detectable above any background signal. Also desirably, the label provides a highly localized signal, thereby providing a high degree of spatial resolution.

Attachment of fluorophores to nucleic acid probes is well-known in the art and can be accomplished by any available means. Fluorophores can be covalently attached to a particular nucleotide, for example, and the labeled nucleotide incorporated into the probe using standard techniques such as nick translation, random priming (Rigby et al., J. Mol. Biol. 113: 237 (1997)), PCR labeling, direct labeling by chemical modification of particular residues, such as cytosine residues (U.S. Pat. No. 5,491,224), and the like. Alternatively, the fluorophore can be covalently attached via a linker to the deoxycytidine nucleotides of the probe that have been transaminated. Methods for labeling probes are described in U.S. Pat. No. 5,491,224, and Morrison et al., *Molecular Cytogenetics: Protocols and Applications*, Chapter 2, "Labeling Fluorescence In Situ Hybridization Probes for Genomic Targets," pp. 21-40, Fan, Ed., Humana Press (2002), both of which are herein incorporated by reference for their descriptions of labeling probes.

One of skill in the art will recognize that other agents or dyes can be used in lieu of fluorophores as label-containing moieties. Luminescent agents include, for example, radioluminescent, chemiluminescent, bioluminescent, and phosphorescent label containing moieties. Alternatively, detection moieties that are visualized by indirect means can be used. For example, probes can be labeled with biotin or digoxygenin using routine methods known in the art, and then further processed for detection. Visualization of a biotin-containing probe can be achieved via subsequent binding of avidin conjugated to a detectable marker. The detectable marker may be a fluorophore, in which case visualization and discrimination of probes can be achieved as described below.

Chromosomal probes hybridized to target regions may alternatively be visualized by enzymatic reactions of label moieties with suitable substrates for the production of insoluble color products. Each probe may be discriminated from other probes within the set by choice of a distinct label moiety. A biotin-containing probe within a set may be detected via subsequent incubation with avidin conjugated to alkaline phosphatase (AP) or horseradish peroxidase (HRP) and a suitable substrate. 5-bromo-4-chloro-3-indolylphosphate and nitro blue tetrazolium (NBT) serve as substrates for alkaline phosphatase, while diaminobenzoate serves as a substrate for HRP.

Kits

Also in view of the above, a kit comprising, or consisting of, (a) a set of one or more probes that enables prognosis of metastasis of malignant melanoma in a patient and (b) instructions for prognosing metastasis of malignant melanoma in the patient is provided. The set of one or more probes comprises (i') a probe for CCND1, alone or in further combination with a probe for a control centromere, and/or (ii') a probe for MYC. The instructions comprise (i') determining in a sample of malignant melanoma obtained from the patient (i) (a) and/or (b), (ii) (c) and/or (d), (iii) (a) and/or (d), or (iv) (b) and/or (c), wherein:

(a) is a copy number ratio of CCND1/control centromere or a copy number of CCND1, wherein a copy number ratio of CCND1/control centromere greater than about 1.55 per cell or a copy number of CCND1 greater than about 2.81 per cell indicates that metastasis will likely occur, (b) is a copy number of MYC, wherein a copy number of MYC greater than about 2.48 per cell indicates that metastasis will likely occur, (c) is a percentage of cells having a gain of CCND1/control centromere or a percentage of cells having a gain of CCND1, wherein a percentage of cells of greater than or equal to about 30% having a gain of CCND1 or a percentage of cells of greater than or equal to about 54% having a gain of CCND1/control centromere indicates that metastasis will likely occur, and (d) is a percentage of cells having a gain of MYC, wherein a percentage of cells of greater than about 20% having a gain of MYC indicates that metastasis will likely occur. The probe for CCND1 can be Vysis LSI CCND1. A probe for a centromere control hybridizes to the alpha satellite DNA located at the centromere of a chromosome. An example of a centromere control probe is a Chromosome Enumerator Probe (Cep). This probe functions as a control, thereby enabling accounting of differences in efficiency of hybridization between samples as necessary. A probe that hybridizes to the alpha satellite DNA located at the centromere of chromosome 1, 2, 3, 4, 5, 6, 7, 8, 9, 10, 11, 12, 13, 14, 15, 16, 17, 18, 19, 20, 21, or 22 can be used. A preferred control centromere probe is one that hybridizes to the alpha satellite DNA of chromosome 11, such as Cep11. The probe for MYC can be Vysis LSI MYC. The kit may further comprise, or consist of, blocking agents or probes, various labels or labeling agents to facilitate detection of the probes, reagents for hybridization (e.g., buffers), a metaphase spread, and the like.

A kit comprising, or consisting of, (a) a set of one or more probes that enables diagnosis and prognosis of malignant melanoma in a patient and (b) instructions for diagnosing malignant melanoma and/or instructions for prognosing metastasis of malignant melanoma in a patient is also provided. The set of probes comprises a probe for RREB1, a probe for MYC, a probe for CCND1, and a probe for CDKN2A, and (b) either instructions for diagnosing malignant melanoma in the patient, wherein the instructions comprise determining in a diagnostic sample obtained from the patient a copy number of RREB1, a copy number of MYC, a copy number of CCND1, and a copy number of CDKN2A, wherein an increase in the copy number of RREB1, an increase in the copy number of MYC, an increase in the copy number of CCND1, and a decrease in the copy number of CDKN2A indicates that the patient has malignant melanoma and/or instructions for prognosing metastasis of malignant melanoma in the patient, wherein the instructions comprise determining in a sample of malignant melanoma obtained from the patient a copy number of RREB1, a copy number of MYC, a copy number of CCND1, and a copy number of CDKN2A, wherein an increase in the copy number of RREB1, an increase in the copy number of MYC, an increase in the copy number of CCND1, and a decrease in the copy number of CDKN2A indicates that metastasis will likely occur. The probe for RREB1 can be Vysis LSI RREB1. The probe for MYC can be Vysis LSI MYC. The probe for CCND1 can be Vysis LSI CCND1. The probe for CDKN2A can be Vysis LSI CDKN2A. The kit may further comprise, or consist of, blocking agents or probes, various labels or labeling agents to facilitate detection of the probes, reagents for hybridization (e.g., buffers), a metaphase spread, and the like.

Further provided is a kit comprising, or consisting of, (a) a set of probes that enables prognosis of metastasis of malignant melanoma in a patient, wherein the set of probes comprises a probe for RREB1, a probe for MYC or ZNF217, a probe for CCND1, and a probe for CDKN2A, and (b) instructions for prognosing malignant melanoma in the patient, wherein the instructions comprise determining in a sample obtained from the patient a copy number of RREB1, a copy number of MYC or ZNF217, a copy number of CCND1, and a copy number of CDKN2A, wherein an increase in the copy number of RREB1, an increase in the copy number of MYC or ZNF217, an increase in the copy number of CCND1, and a decrease in the copy number of CDKN2A indicates that metastasis will likely occur. The probe for RREB1 can be Vysis LSI RREB1. The probe for MYC can be Vysis LSI MYC. The probe for CCND1 can be Vysis LSI CCND1. The probe for CDKN2A can be Vysis LSI CDKN2A. The probe for ZNF217 can be Vysis LSI ZNF217. The kit may further comprise, or consist of, blocking agents or probes, various labels or labeling agents to facilitate detection of the probes, reagents for hybridization (e.g., buffers), a metaphase spread, and the like.

Still further provided is a kit comprising, or consisting of, (a) a set of probes that enables prognosis of metastasis of atypical Spitz tumor in a patient, wherein the set of probes comprises a probe for RREB1, a probe for CCND1, and a probe for CDKN2A, and (b) instructions for prognosing metastasis of atypical Spitz tumor in the patient, wherein the instructions comprise determining in a sample of tumor from the patient a copy number of RREB1, CCND1, and/or CDKN2A, wherein an increase in copy number of RREB1 or an increase in copy number of CCND1 or a homozygous deletion of CDKN2A indicates that aggressive metastasis will likely occur and homozygous deletion of CDKN2A indicates that even more aggressive metastasis will likely occur. The probe for RREB1 can be Vysis LSI RREB1. The probe for CCND1 can be Vysis LSI CCND1. The probe for CDKN2A can be Vysis LSI CDKN2A. The kit may further comprise, or consist of, blocking agents or probes, various labels or labeling agents to facilitate detection of the probes, reagents for hybridization (e.g., buffers), a metaphase spread, and the like.

EXAMPLES

The following examples serve to illustrate the present disclosure. The examples are not intended to limit the scope of the claimed invention in any way.

Example 1

This example describes the evaluation of CCND1, alone or in further combination with a control centromere, and MYC in the prognosis of metastasis in patients with malignant melanoma.

Patients (n=55) with melanoma and documented metastasis were identified in the Northwestern University Dermatology Archives. The patients included those with metastasis limited to the lymph nodes (n=15), in-transit disease (n=8), and distant metastasis (n=32). Twenty seven (27) of the 55 patients were deceased as a result of their disease. The number of patients with Breslow's depths≤1 mm was four, 1 mm<Breslow's depths≤4 mm was 37, and Breslow's depths>4 mm was 14. Forty two patients without metastasis after a minimum of five years of follow-up had Breslow's depths approximately matching those of patients with metastasis. The number of patients with Breslow's depths≤1 mm was 12, 1 mm<Breslow's depths≤4 mm was 24, and Breslow's depths>4 mm was six. Only cases in which the slides, tissue block and clinical course were all available were included in the study. The histopathology of all cases was verified by a dermatopathologist. Along with the clinical course, Breslow's depth, age, sex, site, presence/absence of ulceration, mitotic count, and Clark's level were recorded.

At the time of the initiation of the study, analysis of a database of melanomas revealed 182 melanomas studied by FISH with the clinical diagnostic probe set for melanoma targeting 6p25, Cen 6 (centromere 6), 6q23, and 11q13. Thirty one melanomas showed no evidence of copy number aberrations in the targeted areas (cohort 1). Thirty five unequivocally benign nevi were selected as controls. The 31 melanomas and the 35 nevus controls were then evaluated with probes for eight additional loci, namely 9p21 (CDKN2A), Cen 9 (centromere 9), 8q24 (MYC), 7q34 (BRAF), Cen 17 (centromere 17), Cen 10 (centromere 10), 20q13 (ZNF217), and 1q25 (Cox2). These 8 loci, along with 6p25, 6q23, Cen 6, and 11q13, were among the top 12 loci originally identified by combinatorial analysis of CGH data for the most frequently aberrant loci in melanoma (Gerami et al. (2009), supra). The probes were arranged in two panels. The first panel included 9p21, Cen 9, 1q25, and Cen 17. The second panel included 8q24, 7q34, Cen 10, and 20q13. The hybridizations were all performed on formalin-fixed, paraffin-embedded sections as previously described (Gerami et al. (2009), supra). A reviewer blinded to the case diagnosis enumerated the cases using the protocol described below. A discriminatory analysis looking at the most frequently aberrant loci in the melanoma group relative to the nevus control group was performed to identify the most complementary and additive additional targets.

Ninety seven melanomas (cohort 2), including 55 with metastasis and 42 without metastasis, were analyzed by FISH with two panels of probes. The first panel included the index probe set for melanoma targeting 6p25 (RREB1), 6q23 (MYB), cen 6, and 11q13 (CCND1). The second panel included the four targets identified in the discriminatory analysis of cohort 1, i.e., 9p21 (CDKN2A), cen 9, 8q24 (MYC), and 20q13 (ZNF217). A reviewer blinded to the status of the case as metastasizing or non-metastasizing enumerated all specimens. Sufficient tissue with high quality hybridizations for enumeration was obtained in 97 of 97 cases with the first panel and 91 of 97 cases with the second panel.

The hybridization procedure was performed as previously described (Gerami et al. (2009), supra). The slides were analyzed with an epi-fluorescence microscope equipped with single band-pass filters (Abbott Molecular, Inc., Des Plaines, Ill.). The analyses were performed by a trained technician and a dermatopathologist. All analyses were performed blinded of the specimens' diagnoses. Tumor-bearing areas were localized using the DAPI filter at low magnification. The tumor area was then thoroughly inspected for the presence of nuclei harboring abnormal copy numbers of any probe. Areas with the most significant copy number changes were selected for enumeration. Wherever possible, three abnormal areas were selected, and, within each area, ten random nuclei were analyzed under high power (60× objective). Nuclei had to be nonoverlapping and harbor sufficiently bright signals. Nuclei that showed no signals for more than one probe were not analyzed. Thirty cells were enumerated in each specimen.

The following parameters were calculated for each probe for each specimen: the average signal number per nucleus, the percentage of nuclei with signal counts greater than (percent gain), less than (percent loss), or different (percent aberrant) from two signals. The percentage of nuclei that had more or fewer signals of one probe compared to another (percent relative gain and percent relative loss, respectively), as well as the ratio of the two probes (the total of all signals of one probe divided by that of another probe), were also calculated. A broad number of parameters were separately calculated for the metastasizing and non-metastasizing cases and compared by the Student's t-test. The individual cutoffs and parameter combinations that yielded the best combinations that discriminated the metastasizing versus the non-metastasizing cases were determined by calculating the 'distance from ideal' (DFI) parameter (DFI= $[(1-\text{sensitivity})^2+(1-\text{specificity})^2]^{-1/2}$), as well as the AUC, i.e., the area under the receiver operator characteristic (ROC) curve (see FIG. 1a-FIG. 1d). Varying thresholds independently for each parameter generated a field of points on the graph, and the points with the highest sensitivity value at each specificity value were used to define the curve. Optimal criteria for distinguishing metastatic versus non-metastatic cases were identified, and Kaplan Meier curves for cases meeting the criteria versus those cases not meeting the criteria, as well as the Kaplan Meier curve for the entire group, were then plotted.

ROC curves were also calculated according to Breslow's depth as well as depth combined with other statistically significant FISH parameters. Kaplan Meier curves for the optimally discriminating criteria combining Breslow's depth and FISH were then plotted. This analysis was repeated within Breslow subgroups including cases with Breslow's depth≤1 mm, 1 mm<Breslow's depth≤4 mm, and Breslow's depth>4 mm. A separate analysis for all cases≤2 mm, as well as all cases>2 mm, was also performed. P-values for differences in Kaplan Meier curves were calculated using the Log-rank test.

A log regression analysis, which used all current American Joint Committee on Cancer (AJCC) criteria, including Breslow's depth, age, sex, site, mitotic count, presence/absence of ulceration, and Clark's level, as well as the optimal single parameter FISH criteria of CCND1/Cep6 and MYC value as continuous variables, was performed.

The loci 9p21, 8q24, and 20q13 were identified as the most frequently altered loci in the data set for cohort 1 and, therefore, the most complementary targets. An average CCND1/chromosome 6 of greater than about 1.55 and an average MYC copy number of greater than about 2.48 were identified as the two parameters most highly associated with metastasis in the data set for cohort 2 (see FIG. 1a). The CCND1/chromosome 6 criterion was 95% specific and 38% sensitive for metastasis. The positive predictive value (PPV) was 91%, and the negative predictive value (NPV) was 54%. A Kaplan Meier curve was plotted for cases meeting this criterion versus those that did not and for the entire group (see FIG. 1b). The difference between the metastasizing group and the non-metastasizing group resulted in a p-value of $6.48 \times 10^{-6}$ using a Log-rank test. The MYC criterion was 90% specific and 32% sensitive for metastasis, with a PPV of 80% and an NPV of 53%. A Kaplan Meier curve also demonstrated the difference between those cases meeting the MYC criterion, those that did not, and the entire group (see FIG. 1c). The difference between the metastasizing group and the non-metastasizing group resulted in a p-value of $5.61 \times 10^{-3}$ by the Log rank test, which also reached significance. Hence, patients had a high likelihood of being in the metastatic group if either of the two criteria were met.

A combined criterion, which allowed for meeting a specific CCND1/chromosome 6 value or MYC average copy number value was also highly associated with metastasis. The p-value for the difference in the Kaplan Meier curve for those cases with a CCND1/chromosome 6 value greater than 1.59 or a MYC average copy number greater than 2.48 versus those cases meeting neither of these criteria was $8.9 \times 10^{-7}$ (see FIG. 1d).

A total of 16 patients with Breslow's depth of 1 mm or less were included in the study; 4 of those patients had metastasis. Increased copies of MYC and/or CCND1/chromosome 6 was/were also characteristic of the metastasizing patients in this group. All of the 16 patients were analyzed for CCND1/chromosome 6 value, and 15 of the 16 patients were analyzed for MYC average copy number. The CCND1/chromosome 6 cutoff value of 1.55 was 100% specific for metastasis among patients with a Breslow's depth of ≤1 mm, with 2/2 patients meeting this criterion having metastasis. The CCND1/chromosome 6 cutoff criterion was 50% sensitive, identifying 2/4 metastatic patients in the group. The MYC cutoff value of 2.48 was also 100% specific for metastasis among patients with a Breslow's depth of ≤1 mm, with 2/2 patients meeting this criterion having metastasis. The MYC cutoff criterion was 67% sensitive, identifying 2/3 metastatic patients in the group. Using a combined criterion of patients having a CCND1/chromosome 6 value greater than 1.55 or a MYC average copy number of greater than 2.48 was 100% sensitive and 100% specific for patients with a Breslow's depth of ≤1 mm. While these numbers are too small for a more detailed statistical analysis, these preliminary results suggest that these markers may be able to identify high risk patients among patients with thin melanomas.

Figure 2A:
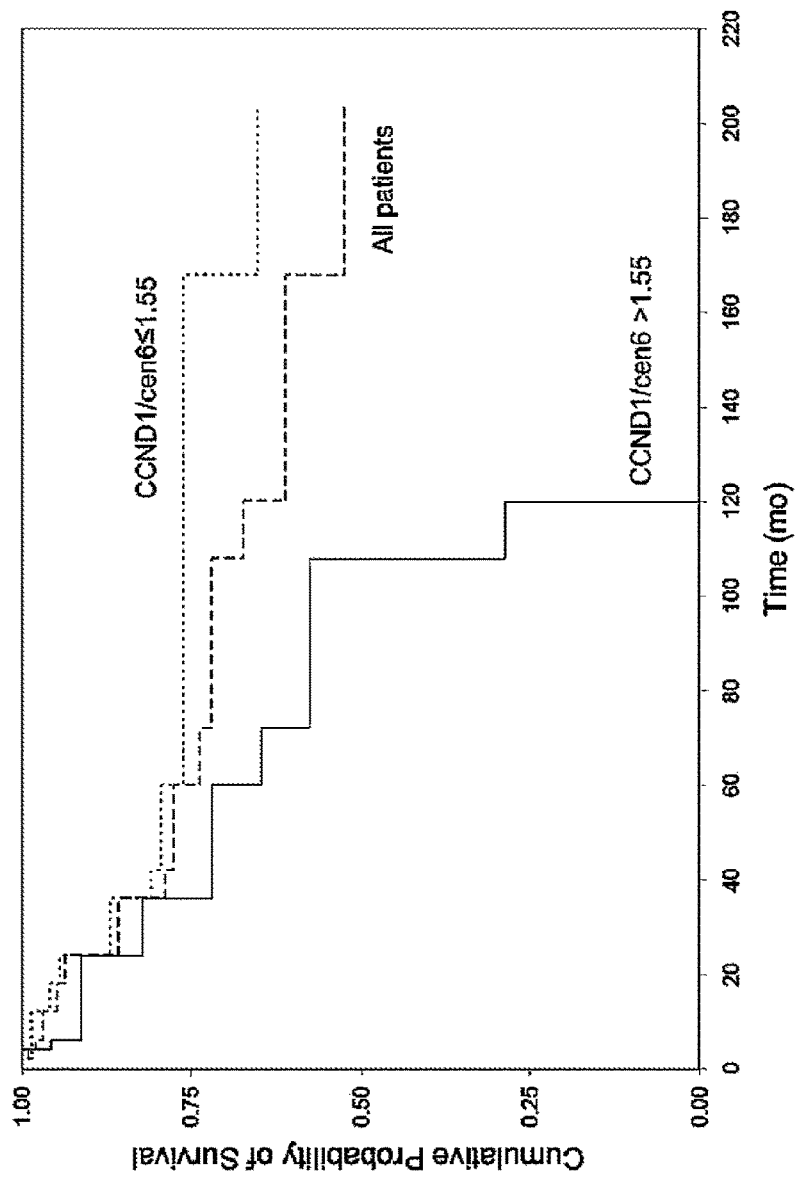
FIG. 2a is a graph of cumulative probability of survival vs. time (months) for CCND1/chromosome 6≤1.55, all patients, and CCND1/chromosome 6>1.55.
Figure 2B:
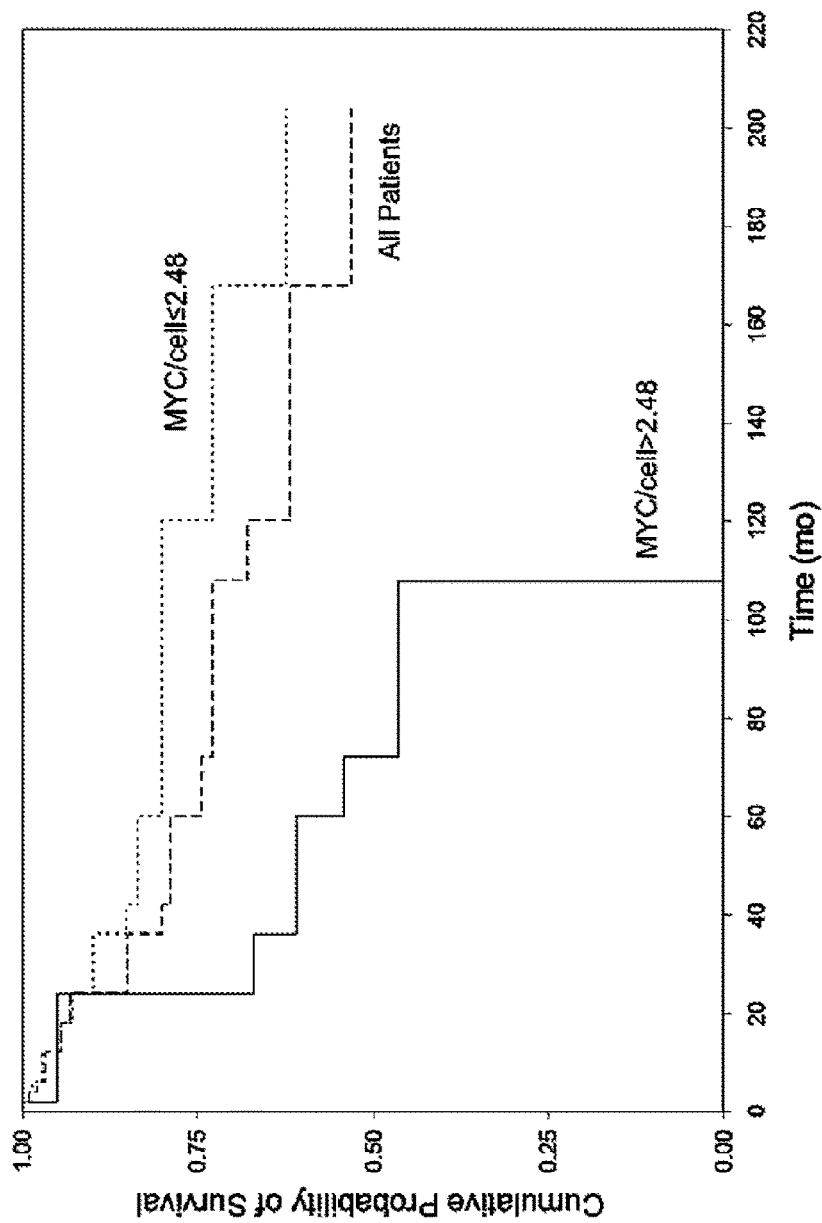
FIG. 2b is a graph of cumulative probability of survival vs. time (months) for MYC/cell≤2.48, all patients, and MYC/cell>2.48.

A total of 57 patients with Breslow's depth of ≤2 mm were included in the study. Data for CCND1/chromosome 6 value was available for all of the 57 patients, whereas data for average MYC value was available for 53/57 patients. Among the 57 patients, there were 26 metastatic events. A CCND1/chromosome 6 value of greater than about 1.55 was 94% specific and 42% sensitive for metastasis in patients with Breslow's depth of ≤2 mm. FIG. 2a shows a Kaplan Meier curve for all patients with Breslow's depth of ≤2 mm, those with CCND1/chromosome 6 greater than 1.55, and those with CCND1/chromosome 6 below 1.55. The p-value in comparing the curve for patients above and below 1.55 was highly significant at $4.8 \times 10^{-5}$. A MYC criterion of average cell count of greater than 2.48 showed the strongest association with metastasis in patients with Breslow's depth of ≤2 mm. The cutoff value of 1.55 was 87% specific and 39% sensitive. FIG. 2b shows the Kaplan Meier curve for all patients with Breslow's depth of ≤2 mm and for those meeting and not meeting the MYC criterion. The difference in the curve for those patients meeting and not meeting the criterion was highly statistically significant with a p-value of $8.24 \times 10^{-3}$. A cutoff requiring an average MYC copy number of 2.36 and CCND1/chromosome 6 of 1.38 resulted in a specificity of 93% and a sensitivity of 48%. The difference in the Kaplan Meier curve for those cases meeting this criterion versus those not meeting this criterion was $4.16 \times 10^{-5}$.

Figure 3A:
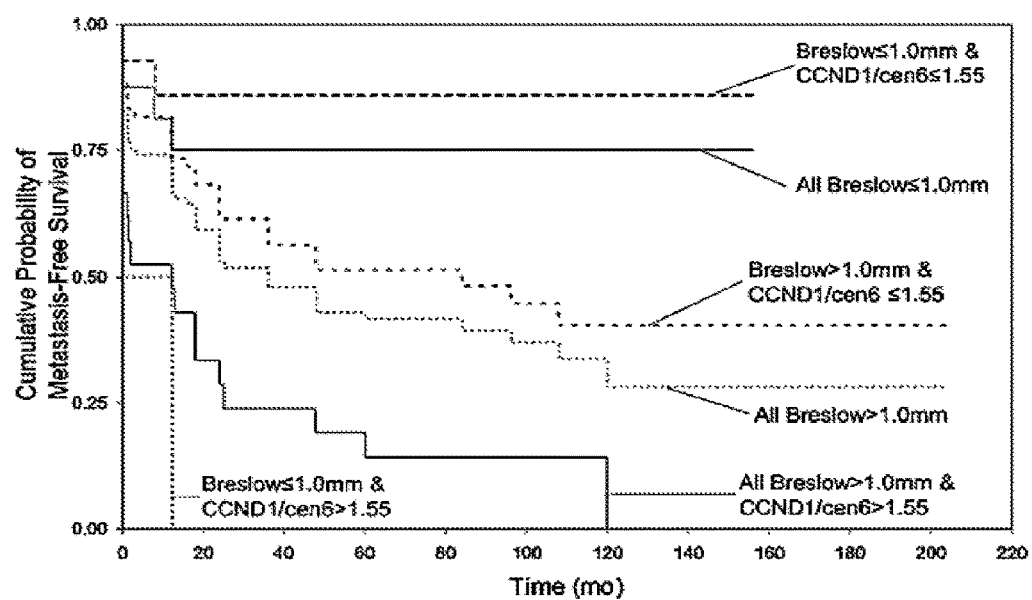
FIG. 3a is a graph of cumulative probability of metastasis-free survival vs. time (months) for Breslow's depths≤1.0 mm and CCND1/chromosome 6≤1.55, all Breslow's depths≤1.0 mm, Breslow's depths≤1.0 mm and CCND1/chromosome 6≤1.55, all Breslow's depths>1.0 mm, all Breslow's depths>1.0 mm and CCND1/chromosome 6>1.55, and Breslow's depths≤1.0 mm and CCND1/chromosome 6>1.55.
Figure 3B:
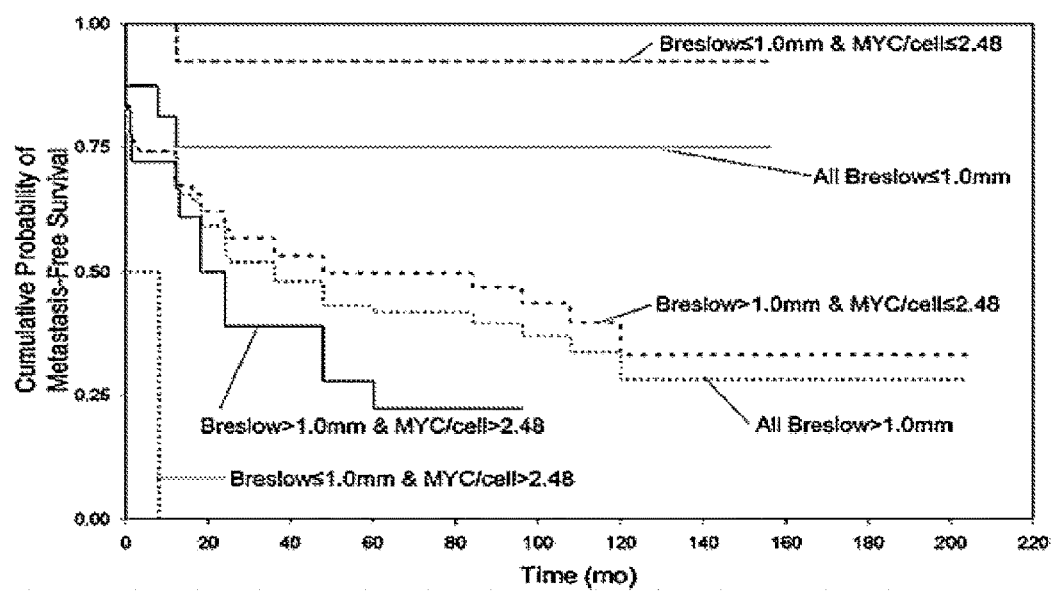
FIG. 3b is a graph of cumulative probability of metastasis-free survival vs. time (months) for Breslow's depths≤1.0 mm and MYC/cell≤2.48, all Breslow's depths≤1.0 mm, Breslow's depths>1.0 mm and MYC/cell≤2.48, all Breslow's depths>1.0 mm, all Breslow's depths>1.0 mm and MYC/cell>2.48, and Breslow's depths≤1.0 mm and MYC/cell>2.48.
Figure 3C:
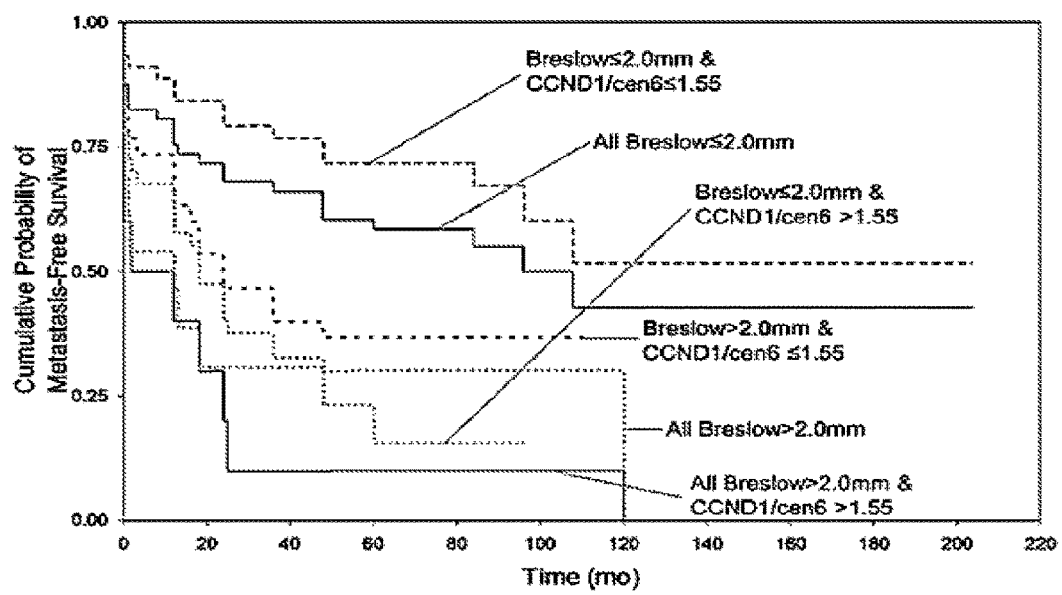
FIG. 3c is a graph of cumulative probability of metastasis-free survival vs. time (months) for Breslow's depths≤2.0 mm and CCND1/chromosome 6≤1.55, all Breslow's depths≤2.0 mm, Breslow's depths>2.0 mm and CCND1/chromosome 6≤1.55, all Breslow's depths>2.0 mm, Breslow's depths≤2.0 mm and CCND1/chromosome 6>1.55, and all Breslow's depths>2.0 mm and CCND1/chromosome 6>1.55.
Figure 3D:
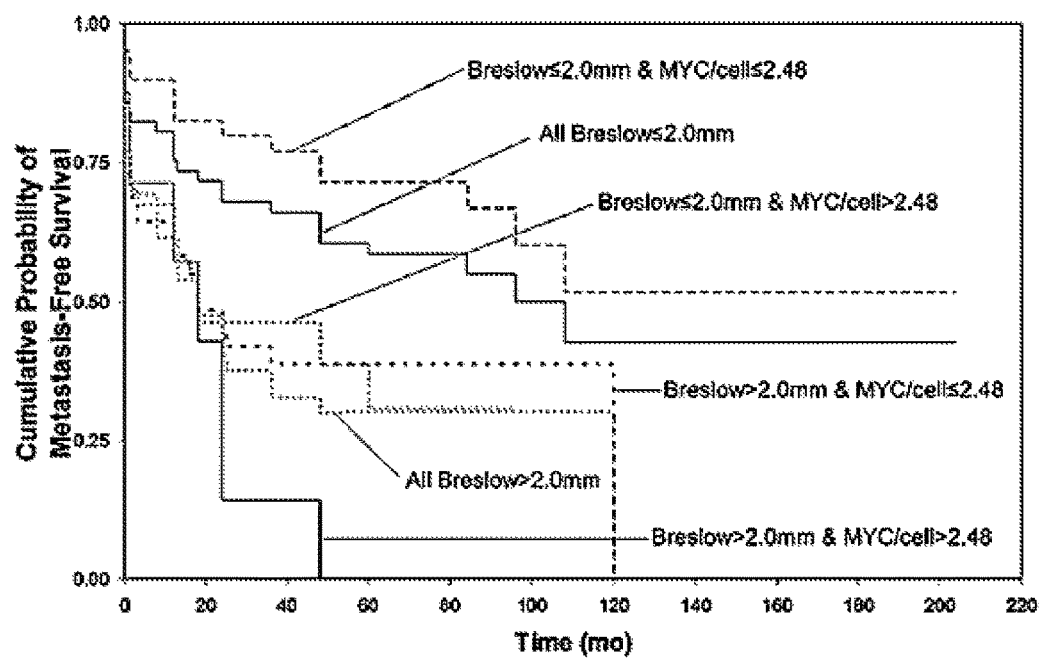
FIG. 3d is a graph of cumulative probability of metastasis-free survival vs. time (months) for Breslow's depths≤2.0 mm and MYC/cell≤2.48, all Breslow's depths≤2.0 mm, Breslow's depths>2.0 mm and MYC/cell≤2.48, all Breslow's depths>2.0 mm and MYC/cell≤2.48, all Breslow's depths>2.0 mm, and Breslow's depths>2.0 mm and MYC/cell>2.48.

Among patients with 1 mm≤Breslow's depth≤4 mm, a CCND1/chromosome 6 cutoff of greater than 1.55 retained the greatest discriminatory value. A CCND1/chromosome 6 value was available for 61 patients in this Breslow category, and MYC average copy number was available for 58 patients in this Breslow category. A CCND1/chromosome 6 value was 92% specific and 43% sensitive for metastasis in this Breslow group. The p-value for the difference in the Kaplan Meier curve for those patients meeting this criterion versus those patients not meeting this criterion was $5.57 \times 10^{-4}$ by the Log-rank test (see FIG. 3a). The MYC cutoff of average copy number greater than 2.60 was 91% specific and 17% sensitive. While cases above this value clearly had a high tendency for metastasis, the p-value for the difference in the Kaplan-Meier curve between those patients meeting this criterion and those not meeting this criterion did not reach statistical significance because of the low sensitivity (see FIG. 3b).

Figure 4A:
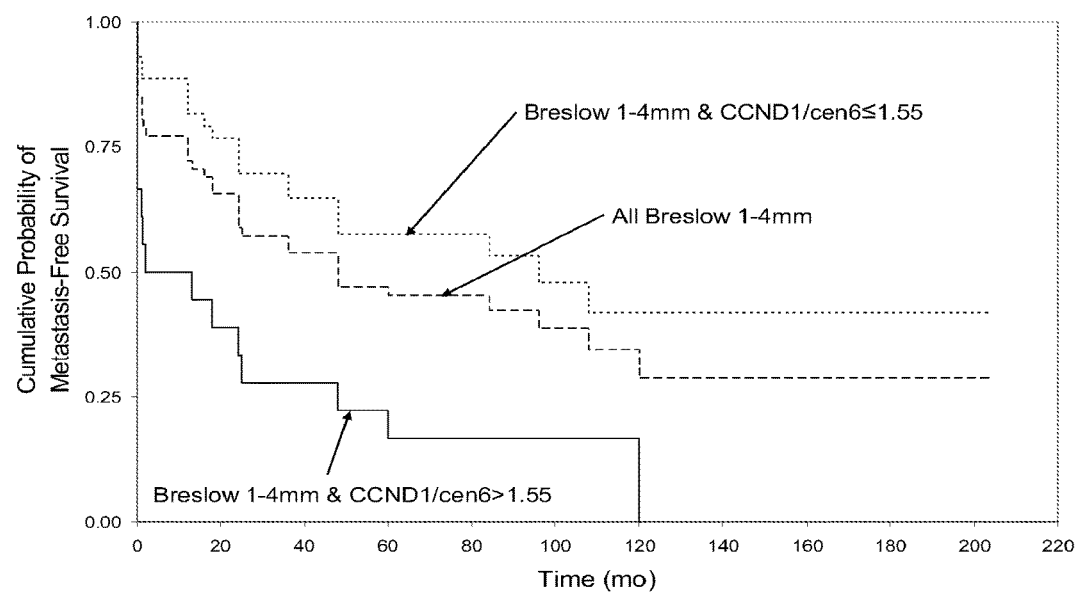
FIG. 4a is a graph of cumulative probability of metastasis-free survival vs. time (months (mo)) for Breslow's depths 1-4 mm and CCND1/chromosome 6 (cen6)≤1.55, all Breslow's depths 1-4 mm, and Breslow's depths 1-4 mm and CCND1/chromosome 6 (cen6)>1.55.

For patients with a Breslow's depth>2.0 mm, the CCND1/chromosome 6 and MYC parameters continued to show a strong association with the highest risk cases. Ten of 10 cases with a CCND1/chromosome 6 cutoff value of greater than 1.55 had metastasis (100% specificity), while only 19/30 patients with a Breslow's depth>2.0 mm and a CCND1/chromosome 6 value below 1.55 had metastasis. In FIG. 4a the Kaplan Meier curve shows the difference in the curve for those cases with a CCND1/chromosome 6 value greater than 1.55 and Breslow's depths≥2.0 mm versus those cases with a CCND1/chromosome 6 less than 1.55 and Breslow's depths greater 2.0, those with CCND1/chromosome 6 greater than 1.55 and Breslow's depths≤2.0, as well as those with a CCND1/chromosome 6 value less than 1.55 and Breslow's depths less than 2.0. Patients with a CCND1/chromosome 6 value≥2.0 and a CCND1/chromosome 6 greater than 1.55 had a significantly higher likelihood for metastasis than those with a CCND1/chromosome 6≤1.55. The p-value by Log-rank test for the difference in the Kaplan Meier curves for these cases was <0.001, which was highly statistically significant. Nineteen of 21 (90%) patients with an average MYC value of greater than 2.22 and Breslow's depth greater than 2.0 developed metastasis. Six of 9 (66%) patients with an average MYC value of 2.22 or less and Breslow's depth>2.0 developed metastasis. The difference in the Kaplan Meier curve for thes two groups was statistically significant by the Log-Rank and Wilcoxon test with a p-value of <0.0001 (see FIG. 4b).

A log regression analysis (see FIG. 5a), including average MYC value, CCND1/chromosome 6 value, presence/absence of ulceration, Clark's level, Breslow's depth, sex, age, site, mitotic count, identified average MYC value, and CCND1/chromosome 6 value as independent prognostic parameters, was performed. The multivariate analysis showed CCND1/chromosome 6 to have the highest prognostic power among all variables, and the MYC average value to have the second highest prognostic power.

Thus, copy number gains in two oncogenes, CCND1 and MYC, emerged as highly linked to metastasis. Copy number gains in CCND1 resulting in an average of CCND1/chromosome 6 value of greater than about 1.55 discriminated between cases with and without metastasis. The Cep6 serves as a reference probe, which helps avoid over-estimation of CCND1-specific gains by neutralizing the effects of tetraploidy (Isaac et al., Am. J. Dermatopathol. 32(2): 144-148 (2010)). This finding was highly specific (95%) and had a PPV for metastasis of 91%. Likewise, the MYC criterion of having an average copy number of greater than about 2.48 was highly specific (90%) and had a PPV of 80%. A number of additional statistical analyses, including Kaplan Meier analysis and logistic regression analysis, confirmed the strong association of these parameters with metastasis. In fact, in a multivariate analysis, the CCND1/chromosome 6 and MYC average copy number were more statistically powerful than other currently recognized AJCC prognosticators, such as Breslow's depth, Clark's level, ulceration status, sex, site and age.

The significance of the CCND1 and MYC gains remained evident throughout the various categories of Breslow's depth. This was evident by comparison of the Kaplan Meier curves for patients meeting the CCND1/chromosome 6 criterion versus those not meeting this criterion within the various Breslow's depth categories. Overall, among the 21 patients from the entire data set that had a positive CCND1/chromosome 6 value (i.e., greater than about 1.55), 20 had a Breslow's depth of greater than 1 mm and less than or equal to 4 mm. Hence, the vast majority of these patients would have been stage II or stage III, a group which may have great variability in outcome. Hence, improvement in prognostication among these patients is clearly relevant and beneficial. Among eight patients with an average MYC copy number of greater than about 2.6, seven had a Breslow's depth of greater than 1 mm and less than or equal to 4 mm. Compared to the entire cohort of 60 patients in this Breslow's depth group, patients meeting either of the CCND1 criterion or the MYC criterion were of significantly greater likelihood to be in the metastatic group. Hence, these markers may identify high risk patients within intermediate stages of traditional categorization, as well as patients with early stage of disease, to respond to targeted inhibitors specific for these oncogenes.

Figure 4B:
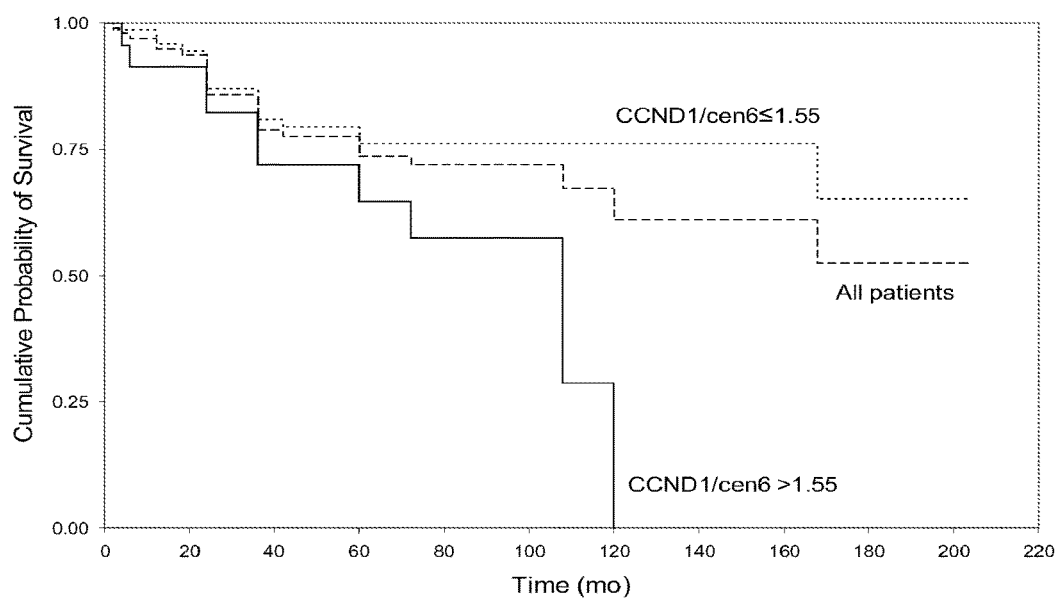
FIG. 4b is a graph of cumulative probability of survival vs. time (months (mo)) for CCND1/chromosome 6 (cen6)≤1.55, all patients, and CCND1/chromosome 6 (cen6)>1.55.

When the above markers are combined with traditional markers, such as Breslow's depth, additive information can be obtained. For example, in analysis of the subgroup of patients with a Breslow's depth over 2 mm, those patients with a CCND1/chromosome 6>1.55 had a significantly worse prognosis than those patients with CCND1/chromosome 6≤1.55. FIG. 4a shows how the combination of the Breslow's depth and the CCND1/chromosome 6 value results in four potential distinct curves with those patients with a Breslow's depth>2 mm and a CCND1/chromosome 6≤1.55 having the best prognosis and those patients with a Breslow's depth>2 mm and a CCND1/chromosome 6>1.55 having the worse prognosis. Similarly, patients with a Breslow's depth>2 mm and with an average MYC copy number>2.48 had significantly worse prognosis than those patients with a Breslow's depth>2 mm and a MYC copy number≤2.48. FIG. 4b demonstrates four distinct KM curves depending on the Breslow's depth and the MYC copy number with patients with a Breslow's depth>2 mm and an average MYC copy number>2.22 having the worse prognosis, and those with a Breslow's depth<2 mm and an average MYC copy number≤2.22 having the best prognosis.

The logistic regression analysis (see Tables 1 and 2) examining CCND1/chromosome 6 and MYC, as well as the Breslow's depth, the Clark's level, the presence/absence of ulceration, sex, age, site, and mitotic count further confirms that these FISH parameters are independent prognostic factors. Additionally, the multivariate analysis shows that the CCND1/chromosome 6 and MYC are first and second, respectively, in their prognostic power in comparison to the other prognosticators, which are listed above and which are currently used by the AJCC.

TABLE 1

Multivariate logistic regression analysis of the effect of CCND1/chromosome 6 > 1.55 on predicting metastases in the presence of various traditional melanoma prognostic factors (n = 92)

| Prognostic factor | chi-square | odds ratio** | 95% confidence level | p-value |
|---|---|---|---|---|
| CCND1/cen 6 > 1.55 | 11.21 | 27.4*** | 5.2-531.7 | 0.0008 |
| Ulceration (yes vs. no)* | 9.17 | 22.6 | 2.7-107.5 | 0.0025 |
| Clark's level (4 vs. 2) | 4.60 | 6.8 | 1.2-25.6 | 0.032 |
| Sex (female vs. male) | 2.70 | 2.9 | 0.8-11.2 | 0.10 |
| Site (extremities vs. trunk) | 1.77 | 0.49 | 0.2-2.3 | 0.18 |
| Breslow's depth (continuous) | 1.59 | 1.12*** | 0.92-1.47 | 0.21 |
| Site (head and neck vs. trunk) | 1.58 | 2.1 | 0.4-7.9 | 0.21 |
| Mitoses (+ vs. −) | 0.10 | 1.006 | 0.86-1.23 | 0.75 |
| Age (continuous) | 0.04 | 1.003*** | 0.968-1.041 | 0.83 |

*for each non-continuous factor, reference category is second category in parentheses
**odds of metastases in category of interest divided by odds of metastases in reference category
***odds ratio is fold-change in odds due to a one-unit change in factor

TABLE 2

Multivariate logistic regression analysis of the effect of MYC/cell > 2.48 on predicting metastases in the presence of various traditional melanoma prognostic factors (n = 88)

| Prognostic factor | chi-square | odds ratio** | 95% confidence interval | p-value |
|---|---|---|---|---|
| Ulceration (yes vs. no)* | 11.03 | 210 | 3.6-146.7 | 0.0009 |
| MYC/cell > 2.48 | 8.07 | 21.3*** | 2.6-176.4 | 0.0045 |
| Clark's level (4 vs. 2) | 4.28 | 5.5 | 1.1-27.5 | 0.038 |
| Sex (female vs. male) | 2.99 | 3.4 | 0.8-13.9 | 0.083 |
| Breslow's depth (continuous) | 2.81 | 1.3*** | 0.96-1.62 | 0.093 |
| Site (head and neck vs. trunk) | 2.30 | 2.3 | .5-10.9 | 0.13 |
| Site (extremities vs. trunk) | 2.16 | 0.6 | .1-2.3 | 0.14 |
| Age (continuous) | 0.37 | 1.011*** | .976-1.048 | 0.54 |
| Mitoses (+ vs. −) | 0.02 | 0.99 | .82-1.19 | 0.90 |

*for each non-continuous factor, reference category is second category in parentheses
**odds of metastases in category of interest divided by odds of metastases in reference category
***odds ratio is fold-change in odds due to a one-unit change in factor

TABLE 3

Specificity and sensitivity of CCND1/chromosome 6 and MYC/cell parameters for predicting metastasis

| Breslow's depth (mm) | CCND1/cen 6 > 1.55 (sensitivity) | CCND1/cen 6 > 1.55 (specificity) | Fisher's exact test CCND1/cen 6 > 1.55 | MYC/cell > 2.48 (sensitivity) | MYC/cell > 2.48 (specificity) | Fisher's exact test MYC/cell > 2.48 |
|---|---|---|---|---|---|---|
| all depths | 38% | 95% | 0.000069 | 32% | 90% | 0.0057 |
| ≤1.0 mm | 50% | 100% | 0.0005 | 67% | 100% | 0.0005 |

TABLE 3-continued

Specificity and sensitivity of CCND1/chromosome 6
and MYC/cell parameters for predicting metastasis

| Breslow's depth (mm) | CCND1/ cen 6 > 1.55 (sensitivity) | CCND1/ cen 6 > 1.55 (specificity) | Fisher's exact test CCND1/cen 6 > 1.55 | MYC/ cell > 2.48 (sensitivity) | MYC/ cell > 2.48 (specificity) | Fisher's exact test MYC/ cell > 2.48 |
|---|---|---|---|---|---|---|
| ≤2.0 mm | 42% | 94% | 0.0016 | 39% | 87% | 0.049 |
| >2.0 mm | 63% | 100% | 0.023 | 67% | 100% | 0.08 |

1) n = 97 for CCND1 for all depths and n = 91 for MYC for all depths
2) n = 16 for CCND1 for Breslow's depth ≤1 mm and n = 15 for MYC for Breslow's depth ≤1 mm
3) n = 57 for CCND1 for Breslow's depth ≤2 mm and n = 51 for MYC for Breslow's depth ≤2 mm
4) n = 40 for CCND1 for Breslow's depth >2 mm and n = 40 for MYC for Breslow's depth >2 mm The above data highly link specific copy number gains of the two oncogenes, namely CCND1 and MYC, with poor prognosis and further implicate them as driver genes in melanoma. Hence, both of these genes may be potential therapeutic targets.

Figure 7:
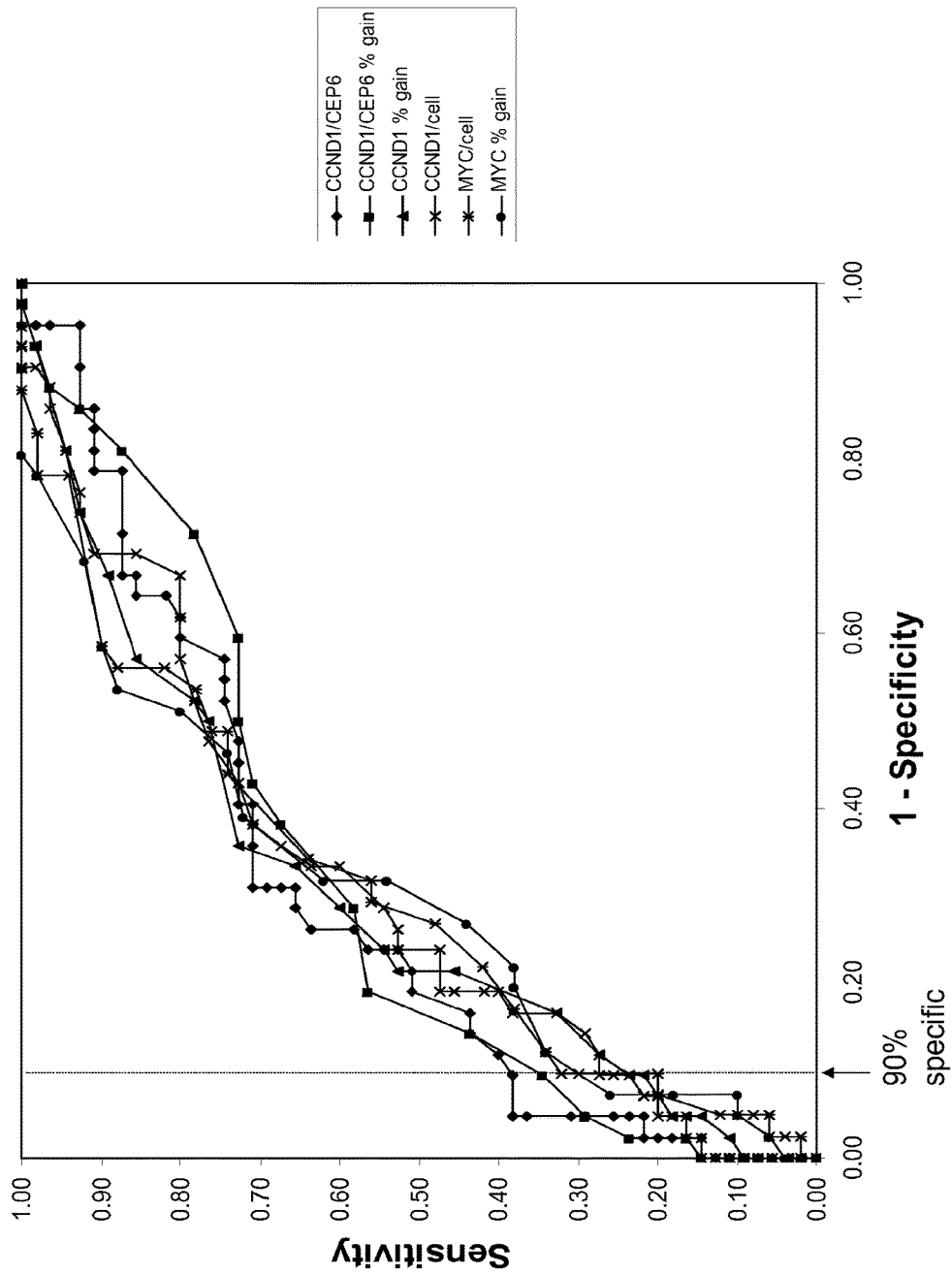
FIG. 7 is a graph of sensitivity vs. 1-specificity for CCND1/CEP6 (◆), CCND1/CEP6% gain (■), CCND1% gain (▲), CCND1/cell (x), MYC/cell (*), and MYC % gain (●).

In addition to the above, the increase in the copy number of CCND1 per cell, the percentage of cells having a gain of CCND1, the percentage of cells having a gain of MYC, and the percentage of cells having a gain of CCND1/control centromere (e.g., centromere of chromosome 6) were also evaluated in the prognosis of metastasis in patients with malignant melanoma. Such parameters were shown to discriminate, with statistical significance in logistic regression analysis, between those patients who progress to metastasis and those who do not. Receiver operator characteristic (ROC) curves were constructed to define cutoffs (see FIG. 7; see also Table 4). The cutoffs were selected to favor specificity, i.e., to minimize the chance of calling a patient with no metastasis "positive," with the optimal cutoff considered to be that which yielded a specificity of greater than about 90% and a sensitivity of greater than about 30%. It was discovered that such percentages were prognostic. The cutoffs were confirmed in survival analysis ($p<0.05$). A copy number of MYC greater than about 2.48 per cell (range of about 2.07 to about 2.53) indicates that metastasis will likely occur (corresponds to a sensitivity/specificity (%)=32/90 (84/44 (best by ROC) to 32/90 (no worse than selected cutoff))). A copy number ratio of CCND1/control centromere greater than about 1.55 per cell (range of about 1.33 to about 1.56) indicates that metastasis will likely occur (corresponds to a sensitivity/specificity (%)=34/93 (68/68 (best by ROC) to 32/95). An increase in the copy number of CCND1 per cell greater than about 2.81 (range of about 2.23 to about 2.96) indicates that metastasis will likely occur (corresponds to a sensitivity/specificity (%)=24/90 (68/66 (best by ROC) to 24/93). A percentage of cells having a gain of CCND1 of greater than about 51% (range of about 30% to about 53%) indicates that metastasis will likely occur (corresponds to a sensitivity/specificity (%)=26/90 (74/66 (best by ROC) to 26/90). A percentage of cells having a gain of MYC of greater than about 51% (range of about 20% to about 53%) indicates that metastasis will likely occur (corresponds to a sensitivity/specificity (%)=26/93 (90/46 (best by ROC) to 26/93). A percentage of cells having a gain of CCND1/control centromere (e.g., centromere of chromosome 6) of greater than about 61% (range of about 54% to about 63%) corresponds to a sensitivity/specificity (%)=32/90 (58/81 (best by ROC) to 32/90). A percentage of cells of greater than or equal to about 30% having a gain of CCND1 (Chi square=5.10296791, probability greater than Chi square=0.0239) and/or a percentage of cells of greater than about 20% having a gain of MYC (Chi square=6.12580207, probability greater than Chi square=0.0133) indicated that metastasis will likely occur.

TABLE 4

Ranges of Cutoffs

| | Cutoff at >90% Specificity | | Cutoff at Highest Sensitivity/Specificity | | Highest Cutoff at >90% Specificity | |
|---|---|---|---|---|---|---|
| Parameter | Cutoff | Survival Log Rank p value | Cutoff | Survival Log Rank p value | Cutoff | Survival Log Rank p value |
| MYC/cell | 2.48 | 0.0096 | 2.07 | 0.0058 | 2.53 | 0.0096 |
| CCND1/Cep6 | 1.55 | 0.007 | 1.33 | 0.0413 | 1.56 | 0.0064 |
| CCND1/Cep6 % gain | 61 | 0.004 | 54 | 0.0014 | 63 | 0.004 |
| CCND1 % gain | 51 | 0.0498 | 30 | 0.0058 | 53 | 0.0498 |
| MYC % gain | 51 | 0.0242 | 20 | 0.0004 | 53 | 0.0242 |
| CCND1/cell | 2.81 | 0.0665 | 2.23 | 0.0221 | 2.96 | 0.0282 |

Example 2

This example describes the determination of a probe set useful in the diagnosis of malignant melanoma.

Following approval from the Northwestern University Lurie Cancer Center (Chicago, Ill.) and the Northwestern University Internal Review Board (IRB) (Chicago, IL) a total of 425 specimens including 207 melanomas and 218 nevi were identified from the Archives of the Northwestern University Department of Dermatology for study with FISH. All specimens consisted of formalin-fixed paraffin-embedded (FFPE) tissue. All cases were evaluated, and the diagnoses were confirmed by a dermatopathologist. The specimens were studied in 4 separate cohorts. Cohort 1 consisted of 31 cases, which were identified by searching a database of melanomas for cases with an unequivocal histologic diagnosis of melanoma but a negative result for FISH with probe set 1 (RREB1 (ras-responsive element binding protein 1; 6p25), MYB (6q23), Cep6 (centromere 6), and CCND1 (11q13)). Also selected were 34 cases of unequivocally benign nevi with varying degrees of atypia, including mild, moderate and severe atypia. This cohort was used to develop the best combinations of probes for further analyses. Cases in cohort 2, 3 and 4 had not been previously studied by FISH. Cohort 2 consisted of 49 melanomas and 51 nevi. This cohort was used to further refine the combinations of probes. Cohort 3 consisted of 72 additional melanoma and 85 nevi and was used to develop cutoffs for the "best" probe combinations. A fourth cohort, consisting of 51 melanomas and 51 nevi, was used to validate the combinations and cutoffs developed using the previous cohorts.

FISH with the multi-colored probe sets described below was performed as previously described (Busam et al., J. Cutan. Pathol 37(2): 196-203 (2010)). The slides were analyzed with an epi-fluorescence microscope equipped with single band-pass filters (Abbott Molecular Inc., Des Plaines, Ill.). The analyses were performed by a trained technician and a dermatopathologist. All analyses were performed blinded of the specimens' diagnoses. Tumor-bearing areas were localized using the DAPI filter at low magnification. The tumor area was then thoroughly inspected for the presence of nuclei harboring abnormal copy numbers of any probe. Areas with the most significant copy number changes were selected for enumeration. Wherever possible, three or fewer abnormal areas were selected, and within each area a minimum of 10 random nuclei were analyzed under high-power (60× objective). To qualify, nuclei had to be non-overlapping and harbor sufficiently bright signals. Nuclei that showed no signals for more than two probes were not analyzed. Thirty cells were enumerated in each specimen. The enumeration was done by a technician highly experienced in FISH enumeration and histopathology.

Data were provided in the form of signal counts for each probe in individual cells of each specimen (30 cells enumerated per specimen). The data were then reduced to calculate the following parameters, per specimen, for each probe:

% Gain: percentage of cells with greater than two probe signals (number of cells with >2 signals, divided by the number of cells enumerated and multiplied by 100), and % Loss: percentage of cells with less than two probe signals (number of cells with <2 signals, divided by the number of cells enumerated and multiplied by 100).

In the case of CDKN2A (9p21), the percentage of homozygous deletion of the CDKN2A locus (or zero signals per cell) was additionally calculated. Additionally, in some instances ratios of two probes were constructed and percent gains, losses and imbalances for these ratios were calculated, considering a ratio gain per cell as greater than 1, and the ratio loss per cell as less than 1.

In general two analytical methods were used. One method involved the use of a logistic regression model to categorize the probability of being categorized as melanoma or nevi. The second method involved the use of varied cutoff values for each FISH parameter to calculate sensitivity and specificity of discriminating melanoma vs. nevi. For multi-probe combinations, varying cutoffs independently for each parameter generates a field of points on a graph, and the points with the highest sensitivity value at each specificity value are used to define the receiver operator characteristic (ROC) curve. From the ROC curves, the distance from ideal (DFI) and the area under the ROC curve (AUC) were calculated.

The DFI parameter was calculated as follows:

$$DFI = \sqrt{(1-SENS)^2 + (1-SPEC)^2}.$$

DFI represents the minimum distance from the ROC curve to the value of a sensitivity of 1 and a false positive rate (1−specificity) of 0. The DFI ranges from 0-1 with 0 being the ideal.

While statistical methods were used to generate possible combinations and cutoff values, scientific judgment was used to weigh the various tradeoffs to result in the final decision of cutoff values and probe combinations. Specifically, for each specimen cohort, the following analysis was carried out for probe selection, probe set definition, and validation.

Cohort 1

In a previous study in a combinatorial analysis of comparative genomic hybridization data on melanoma from Bastian et al., 14 loci were identified as being most frequently altered. This includes the probes used in probe set 1 (Busam et al. (2009), supra). Among the remaining probes from this list, the following eight additional probes were selected: CDKN2A (9p21), centromere 9 (Cep9), MYC (8q24), BRAF (7q34), centromere 17 (Cep17), centromere 10 (Cep10), ZNF217 (zinc finger protein 17; 20q13), and Cox2 (1q25) and arranged in two probe sets. This included CDKN2A (9p21), centromere 9 (Cep9), Cox2 (1q25) and centromere 17 (Cep17) in the first probe set and MYC (8q24), BRAF (7q34), centromere 10 (Cep10) and ZNF217 (20q13) in the second probe set. Both probe sets were applied to the 31 melanomas and 35 nevi from cohort 1. Analyses were carried out to determine which loci were most frequently gained or lost in melanoma specimens as compared to nevi specimens to select the four top-performing probes for further evaluation (referred to as probe set 2). The mean and standard deviation of each FISH parameter were calculated separately for the benign and malignant cases of each cohort and compared by the student t test. Parameters showing significant differences between the two groups (p<0.05) were selected for further analysis. This information was represented as sensitivity and specificity of different loci for detection of cancer. For each probe parameter—percent gain and loss—a ROC curve was constructed shifting individual thresholds for positivity across a range. The minimal distance from ideal (DFI) of sensitivity and specificity and AUC were calculated.

Cohort 2

In Cohort 2, parameter combinations that yielded the best combination of sensitivity and specificity were determined. The probe parameters were grouped in all possible combinations of two, three and four, and then analyzed using a logistic regression model. While not allowing for the calculation of individual cutoff values, the logistic regression allows for an estimation of the ROC curve and its area, as well as the minimum DFI. Based on this analysis, the four top-performing four-probe combinations, which included homozygous deletions in 9p21 as well as three other targets outside of chromosome 9, were identified.

Cohort 3

Cohort 3 consisted of 157 specimens, including 72 melanomas and 85 nevi, which were evaluated using the final selected probe set targeting RREB1 (6p25), p16 (9p21), CCND1 (11q13) and MYC (8q24). Building on the analyses from Cohort 2, the Cohort 3 data set was used to examine various cutoffs for probe parameters in order to select the optimal cutoff for positivity for the final probe set. Cutoffs were calculated on an individual probe basis within the combination of four probes, and also as a fixed value across four probes. Two additional rules were applied to the signal counts to reduce the influence of tetraploid cells and cells with sub-optimal hybridization. To reduce the influence of tetraploid cells, cells with 3-4 signals for CDKN2A, RREB1, CCND1 and MYC were not included in the numerator used to calculate percentages (loss, gain, imbalance or homozygous), but were included in the denominator. To reduce the influence of insufficient hybridization, cells with zero signals for any three or more of the four probes were excluded from the calculation of percentages (loss, gain, imbalance or homozygous). The ROC curves were constructed, and the DFI and AUC values were calculated.

Cohort 4

An independent cohort consisting of 51 melanoma and 51 nevi specimens was evaluated with newly determined probe set 3 and the predetermined criteria as a validation cohort. This cohort was also evaluated with probe set 1 using the original published cutoffs (Busam et al. (2009), supra). Probes in this data set were RREB1, MYB, CCND1 and Cep6 for probe set 1 and RREB1, CDKN2A, CCND1 and MYC for probe set 3.

Figure 5:
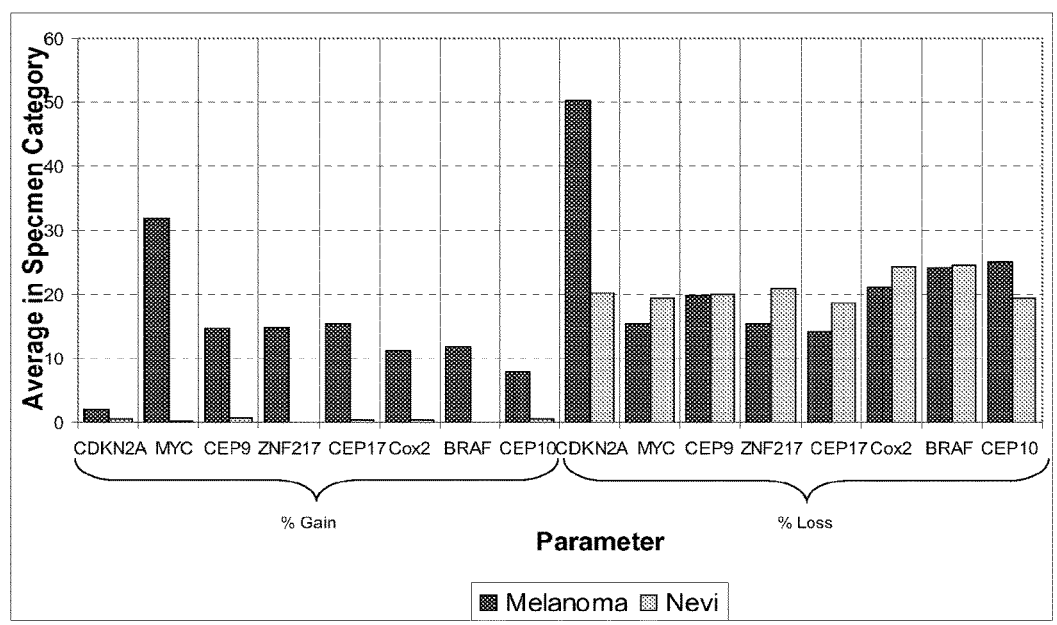
FIG. 5 is a bar graph of average in specimen category vs. parameter, which shows the proportion of cells with chromosomal abnormalities (gain or loss) in the melanoma group and the nevus group for representative parameters calculated for each of the probes CDKN2A, MYC, CEP9, ZNF217, Cox2, BRAF and CEP10.

FIG. 5 shows the results of the evaluation of the Cohort 1 analysis including 31 melanoma and 35 nevi with probes targeting CDKN2A (9p21), Cep9 (centromere 9), MYC (8q24), BRAF (7q34), Cep17, Cep10, ZNF217 (20q13), and Cox 2 (1q25). The plot illustrates the average proportion of cells with chromosomal abnormalities (gain or loss) in the melanoma and nevus groups for representative parameters calculated for each of the eight probes. Nevi specimens exhibited zero or very few cells with chromosomal gains and approximately 18-30% of cells with apparent chromosomal losses mostly related to nuclear truncation on FFPE specimens. Melanoma specimens demonstrated significant chromosomal copy number gains, as well as an elevated number of cells with deletions at the CDKN2A (9p21) locus.

Table 5 shows the top ten best parameters selected as a result of the discriminant analysis of the loci listed above, as judged by the highest AUC and DFI. The discriminant analysis identified CDKN2A (9p21), Cep9, ZNF217 (20q13) and MYC (8q24) as the most complementary set of probes to probe set 1. Each of the probes in the set showed a highly significant p value when comparing the average enumeration values between the melanoma group and the nevus group.

TABLE 5

| FISH parameter | AUC | DFI | Spec. | Sens. | Mean Positive (melanoma) | Mean Negative (nevus) | T-test p-value |
|---|---|---|---|---|---|---|---|
| CDKN2A % loss | 0.959 | 0.087 | 94.1 | 93.5 | 50.2 | 18 | <.0001 |
| ZNF217 % gain | 0.952 | 0.097 | 100 | 90.3 | 14.8 | 0 | <.0001 |
| CDKN2A/CEP9 ratio % loss | 0.944 | 0.216 | 79.4 | 93.5 | 44.8 | 16.5 | <.0001 |
| MYC % gain | 0.931 | 0.142 | 94.1 | 87.1 | 31.8 | 0.2 | <.0001 |
| CEP9 % gain | 0.928 | 0.113 | 94.1 | 90.3 | 14.7 | 0.7 | <.0001 |
| CEP17 % gain | 0.924 | 0.142 | 94.1 | 87.1 | 15.5 | 0.3 | <.0001 |
| BRAF % gain | 0.919 | 0.161 | 100 | 83.9 | 11.8 | 0 | <.0001 |
| Cox 2 % gain | 0.890 | 0.213 | 91.2 | 80.6 | 11.3 | 0.4 | <.0001 |
| CEP10 % gain | 0.837 | 0.273 | 91.2 | 74.2 | 7.8 | 0.6 | 0.0003 |
| CEP10 % loss | 0.651 | 0.537 | 52.9 | 74.2 | 25.2 | 19.4 | 0.1591 |

AUC = area under the ROC curve;
DFI = distance from ideal;
Spec. = specificity;
Sens. = sensitivity Additionally, parameters based on the probes selected for further study exhibited the highest AUC and DFI in ROC analysis. The DFI value was used for probe prioritization only. The most optimal combinations of probes were selected using Cohort 2 analyzed with probes for RREB1, MYB, CCND1, Cep6, CDKN2A, ZNF217, Cep9 and MYC. Using the logistic regression analysis, four combinations of four probe parameters with the highest AUC and lowest DFI were selected for further examination (Table 6).

TABLE 6

| Parameter Combination | Cutoff for Parameter No. | | | | Sensitivity (%) | Specificity (%) | AUC | DFI | FPR |
|---|---|---|---|---|---|---|---|---|---|
| | 1 | 2 | 3 | 4 | | | | | |
| CDKN2A % loss RREB1 % gain ZNF217 % gain CCND1 % gain | 66 | 31 | 31 | 21 | 89.8 | 90.2 | 0.969 | 0.142 | 0.098 |
| CDKN2A % loss MYC % gain ZNF217 % gain CCND1 % gain | 61 | 16 | 31 | 21 | 89.8 | 94.12 | 0.970 | 0.118 | 0.059 |
| CDKN2A % loss RREB1 % gain MYC % gain CCND1 % gain | 61 | 41 | 16 | 21 | 87.76 | 92.16 | 0.962 | 0.145 | 0.078 |

TABLE 6-continued

| Parameter Combination | Cutoff for Parameter No. | | | | Sensitivity (%) | Specificity (%) | AUC | DFI | FPR |
|---|---|---|---|---|---|---|---|---|---|
| | 1 | 2 | 3 | 4 | | | | | |
| CDKN2A % loss RREB1 % gain MYC % gain ZNF217 % gain | 61 | 41 | 16 | 31 | 91.84 | 92.16 | 0.973 | 0.113 | 0.078 |

AUC = area under the ROC curve;
DFI = distance from ideal;
FPR = false positive rate The DFI analysis from Cohort 2 identified two potential sets of probe targets among the top four probe combinations. These two combinations included CDKN2A (9p21), RREB1 (6p25), MYC (8q24) and CCND1 (11q13) in the first set and CDKN2A (9p21), RREB1 (6p25), MYC (8q24) and ZNF217 (20q13) in the second set. Both sets had excellent DFI with only a marginal difference, 0.145 versus 0.113, respectively. Since a previous prognostic study showed significant prognostic value of the 8q24 (Barnhill et al. (1999), supra) and 11q13 loci, the first combination was selected in order to maximize the prognostic potential of the assay. Therefore, the final probe set selected included CDKN2A (9p21), RREB1 (6p24.3), MYC (8q24) and CCND1 (11q13.3). This was labeled as probe set 3.

Figure 6:
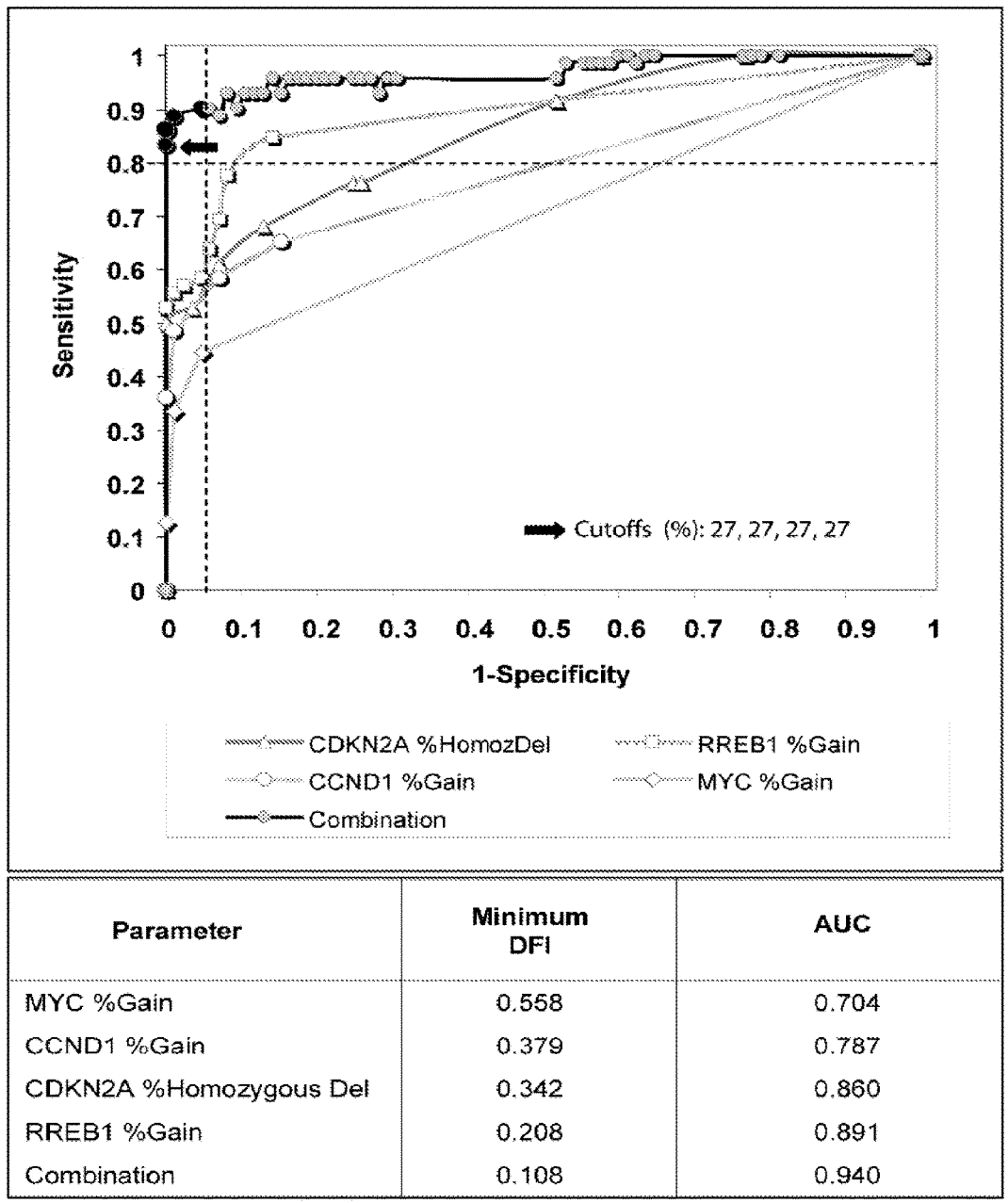
FIG. 6 is a graph of sensitivity vs. 1-specificity for CDKN2A % homozygous deletion (△), CCND1% gain (○), RREB1 % gain (□), MYC % gain (◇), and all probes (●).

Cutoffs were determined using Cohort 3. ROC curves for the 157 specimens of Cohort 3 tested with probe set 3 are shown in FIG. 6. A plot for each individual probe parameter is shown (CDKN2A Percent Homozygous, RREB1 Percent Gain, MYC Percent Gain, and CCND1 Percent Gain), as well as the combination of four parameters. In the targeted area of the curve with specificity in the 95% or greater region, several cutoff combinations for four probes were available, represented by the black-filled circles on the plot.

FIG. 6 is the ROC plot for individual FISH parameters (CDKN2A Percent Homozygous, RREB1 Percent Gain, MYC Percent Gain, and CCND1 Percent Gain) and the four-parameter combination. Parameters were calculated from the FISH evaluation of the 72 melanoma and 85 nevi specimens (Cohort 3). Highest sensitivity and specificity are shown at the point of minimum DFI. Performance with the conservatively selected set of cutoffs is shown by the arrow. The selected cutoff of 27% for each probe is shown as an error on the plot. The AUC highlighted by blackened circles indicate a targeted region of sensitivity and specificity.

The most conservative cutoff was selected using the condition that greater than or equal to 8 cells out of 30 must be abnormal to call the specimen positive, since in our practical experience cutoffs below this have some vulnerability to false positives as a result of tetraploidy. As evident from FIG. 6, the cutoffs satisfying this condition were the same for all four parameters (27, 27, 27, 27 for CDKN2A Percent Homozygous, RREB1 Percent Gain, MYC Percent Gain, and CCND1 Percent Gain, respectively), and resulted in a sensitivity of 83.33% and a specificity of 100.00%, which translates, in this cohort, to a positive predictive value of 1.0 and a negative predictive value of 0.88. Also evident from FIG. 6, a homozygous CDKN2A (9p21) deletion showed a high discriminatory value for distinguishing spitz nevi from spitzoid melanomas.

In addition to cutoff selection, the performance of a new probe set was compared to that of probe set 1. Table 7 shows performance of probe set 1 using published evaluation criteria and cutoffs for positivity (Gerami et al., Am. J. Surg. Pathol. 33(12): 1783-1788 (2009)) compared to performance of the new probe set with two different sets of cutoffs: the one resulting in highest sensitivity and specificity on the ROC curve and one chosen conservatively. Probe set 1 resulted in a sensitivity of 72% and a specificity of 98%, while the new probe set known as probe set 3, with conservatively selected cutoff, demonstrated a sensitivity of 83% and a specificity of 100%.

TABLE 7

| Description | True Pos. | True Neg. | False Pos. | False Neg. | Cutoff for Parameter No. | | | | DFI | Sensitivity (%) | Specificity (%) |
|---|---|---|---|---|---|---|---|---|---|---|---|
| | | | | | 1 | 2 | 3 | 4 | | | |
| RREB1 % gain, CCND1 % gain, RREB1/CEP6 % gain, MYB/CEP6 % loss | 51 | 84 | 2 | 20 | 29 | 38 | 55 | 40 | 0.283 | 71.8 | 97.7 |
| CDKN2A % homozygous, RREB1 % gain, MYC % gain, CCND1 % gain | 60 | 85 | 0 | 12 | 27 | 27 | 27 | 27 | 0.167 | 83.3 | 100.0 |

TABLE 7-continued

| Description | True Pos. | True Neg. | False Pos. | False Neg. | Cutoff for Parameter No. | | | | DFI | Sensitivity (%) | Specificity (%) |
| --- | --- | --- | --- | --- | --- | --- | --- | --- | --- | --- | --- |
| | | | | | 1 | 2 | 3 | 4 | | | |
| CDKN2A % homozygous, RREB1 % gain, MYC % gain, CCND1 % gain | 65 | 81 | 4 | 7 | 20 | 20 | 1 | 7 | 0.108 | 90.3 | 95.3 |

DFI = distance from ideal

In a validation study of the probe set consisting of CDKN2A (9p21), RREB1 (6p24.3), MYC (8q24), and CCND1 (11q13.3), which used the predetermined cutoffs established in Cohort 3, an independent cohort of 51 melanomas and 51 nevi specimens were analyzed. The following rules for calling cells positive were applied:

a cell is tetraploid for all three probes (MYC, CCND1 and RREB1), this cell is not counted as abnormal for MYC, CCND1 and RREB1, and if a cell is tetraploid for all three probes (MYC, CCND1 and RREB1), this cell is counted as abnormal if it is homozygous for 9p21 deletion.

In this validation cohort, using cutoffs of 27% (if ≥27% of the nuclei counted are abnormal, the specimen is positive) for each probe, the sensitivity was determined to be 94% and the specificity was determined to be 98%, confirming the superior performance of the new probe set (Table 8). Since 27% out of 30 cells is 8.1 cells, an analysis was also done using 8 cells as a cutoff (if ≥8 nuclei/30 nuclei counted are abnormal, the specimen is positive), resulting in an even higher sensitivity (Table 9).

TABLE 8

| Count Row % | FISH-negative | FISH-positive | |
| --- | --- | --- | --- |
| Melanoma | 3 | 48 | 51 |
| | 5.88 | 94.12 | |
| Nevi | 50 | 1 | 51 |
| | 98.04 | 1.96 | |
| | 53 | 49 | 102 |

TABLE 9

| Count Row % | FISH negative | FISH positive | |
| --- | --- | --- | --- |
| Melanoma | 2 | 49 | 51 |
| | 3.92 | 96.08 | |
| Nevi | 50 | 1 | 51 |
| | 98.04 | 1.96 | |
| | 52 | 50 | 102 |

Frequent loss of 9p21 and the targeting of loci from four distinct chromosomes makes this assay significantly less vulnerable to false positives as a result of tetraploidy. The presence of tetraploid cells in spitzoid neoplasms is the primary source of false positives with probe set 1. Tetraploid cells can be seen in benign spitz nevi, spitz tumors, and spitzoid melanomas and are, therefore, non-diagnostic, but for an inexperienced enumerator may give the false impression of imbalanced chromosomal gains, particularly when nuclei are truncated in sectioning. Since probe set 1 targets three loci from chromosome 6 and one locus from chromosome 11, distinguishing tetraploid cells from cells with whole chromosome 6 gains can prove challenging. Conversely, the four loci targeted by probe set 4 originate from four distinct loci and include 9p21, which is typically deleted, as a target. Hence, probability highly favors that a cell showing balanced gains in all four probes, including 9p21, is a tetraploid cell. Since tetraploid cells then can be recognized with greater confidence, a formula can be used to eliminate tetraploidy as a source of false positives. The formula eliminates tetraploid cells from being including in the numerator when calculating the percentage of aberrant cells but maintains them in the denominator. This essentially increases the demand for the number of clonally aberrant cells to be present among the enumerated cells in order to obtain a positive result without diminishing the sensitivity of the assay. In applying this rule, tetraploidy is eliminated as a source of false positives without any significant diminution of sensitivity.

Among the top four performing probe set combinations identified from Cohort 2, two probe sets showed prognostic potential (Table 6). One probe set targeted 6p25, 9p21, 11q13 and 20q13, and the other probe set targeted 6p25, 9p21, 11q13 and 8q24. The DFI value was slightly better for the probe set including 20q13 (0.113 compared to 0.145 for the probe set including 8q24 and 11q13). However, because of previously demonstrated prognostic value of 8q24 and 11q13 and the marginal difference in DFI, the probe set including 8q24 and 11q13 is expected to have the greatest prognostic potential in ambiguous spitz tumors.

Figure 8:
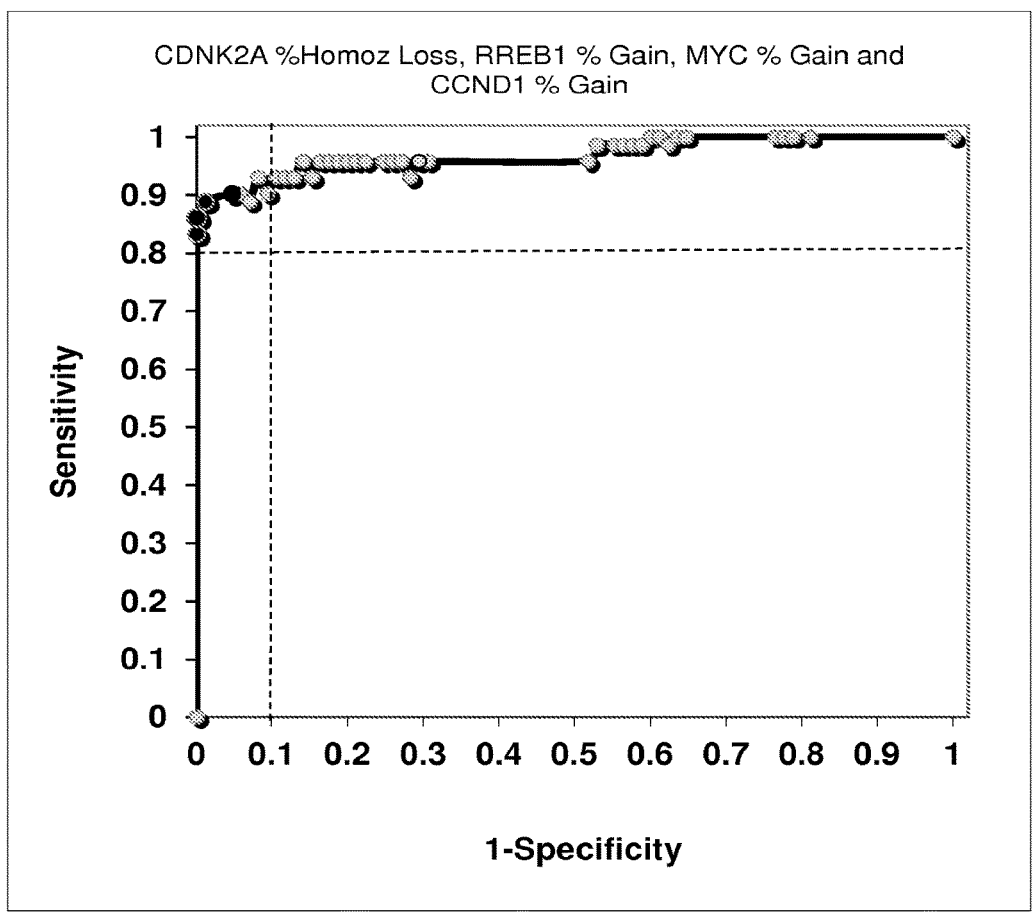
FIG. 8 is a graph of sensitivity vs. 1-specificity for CDNK2A % homozygous loss, RREB1 % gain, MYC % gain, and CCND1 % gain.

Receiver operator characteristic (ROC) curves were constructed to define cutoffs for CDKN2A (9p21), RREB1 (6p25), MYC (8q24), and CCND1 (11q13) for Cohort 3 (see FIG. 8; see also Table 10). A total of 30 cells was analyzed per specimen, and the percentage of abnormal cells was calculated. Cells that had three or four FISH signals for all of the probes except for CDKN2A but did not have a CDKN2A (9p21) deletion were considered tetraploid and were not counted as abnormal cells; instead, they were counted as normal cells for the purpose of calculating the percentage of abnormal cells. Cells that had three or four FISH signals for all of the probes except for CDKNA2 (9p21) and had a CDKN2A (9p21) deletion were counted as abnormal cells. Application of the above rule ("tetraploidy rule") increased specificity of discrimination of benign tetraploid nevi (the cells of which had 2× gain of all chromosomes in the genome) from melanoma (the cells of which had locus-specific chromosomal abnormalities). The cutoffs were selected to favor specificity, i.e., to minimize the chance of calling a patient with no metastasis "positive," with the optimal cutoff considered to be that which yielded a specificity of greater than about 90% and a sensitivity of greater than about 80%. It was discovered that such percentages were diagnostic.

Multiple combinations of cutoffs for the CDKN2A, RREB1, MYC, and CCND1 FISH parameters listed below yielded at least about 80% sensitivity and at least about 90% specificity (as defined by target performance):

CDKN2A % homozygous deletion of about 20 to about 33,
RREB1% gain of about 20 to about 33,
MYC % gain of about 1 to about 48, and
CCND1% gain of about 11 to about 46.

The specific cutoff combinations that defined the lowest and the highest performance within the acceptable range around the selected cutoff of about 27%, such as the selected cutoff of 27%, for each probe are shown in Table 10.

TABLE 10

Cutoff Range Combinations for CDKN2A, RREB1, MYC, and CCND1

| Parameter | Cutoff CDKN2A % homozygous | Cutoff RREB1 % gain | Cutoff MYC % gain | Cutoff CCND1 % gain | Sensitivity (%) | Specificity (%) |
|---|---|---|---|---|---|---|
| Upper Range of Cutoff | 33 | 33 | 48 | 46 | 80.6 | 100 |
| Chosen Cutoff | 27 | 27 | 27 | 27 | 83.3 | 100 |
| Lower Range of Cutoff | 20 | 20 | 1 | 5 | 90.3 | 91.8 |

Receiver operator characteristic (ROC) curves were constructed to define cutoffs for CDKN2A (9p21), RREB1 (6p25), either MYC (8q24) or CCND1 (11q13), and ZNF217 for Cohort 2 (see Table 11). A total of 30 cells was analyzed per specimen, and the percentage of abnormal cells was calculated. Cells that had three or four FISH signals for all of the probes except for CDKN2A but did not have a CDKN2A (9p21) deletion were considered tetraploid and were not counted as abnormal cells; instead, they were counted as normal cells for the purpose of calculating the percentage of abnormal cells. Cells that had three or four FISH signals for all of the probes except for CDKNA2 (9p21) and had a CDKN2A (9p21) deletion were counted as abnormal cells. Application of the tetraploidy rule increased specificity of discrimination of benign tetraploid nevi (the cells of which had 2× gain of all chromosomes in the genome) from melanoma (the cells of which had locus-specific chromosomal abnormalities). The cutoffs were selected to favor specificity, i.e., to minimize the chance of calling a patient with no metastasis "positive," with the optimal cutoff considered to be that which yielded a specificity of greater than about 90% and a sensitivity of greater than about 80%. It was discovered that such percentages were diagnostic.

Multiple combinations of cutoffs for the CDKN2A, RREB1, ZNF217, and CCND1 FISH parameters listed below yielded at least about 80% sensitivity and at least about 90% specificity (as defined by target performance):

CDKN2A % homozygous deletion of about 20 to about 30,
RREB1% gain of about 27 to about 30,
ZNF217% gain of about 14 to about 33, and
CCND1% gain of about 24 to about 29.

The specific cutoff combinations that defined the lowest and the highest performance within the acceptable range around the selected cutoff of about 27%, such as the selected cutoff of 27%, for each probe are shown in Table 11.

TABLE 11

Cutoff Range Combinations for CDKN2A, RREB1, ZNF217, and CCND1

| Parameter | Cutoff CDKN2A % homozygous | Cutoff RREB1 % gain | Cutoff ZNF217 % gain | Cutoff CCND1 % gain | Sensitivity (%) | Specificity (%) |
|---|---|---|---|---|---|---|
| Upper Range of Cutoff | 30 | 30 | 33 | 29 | 81.6 | 94.1 |
| Chosen Cutoff | 27 | 27 | 27 | 27 | 81.6 | 90.2 |
| Lower Range of Cutoff | 27 | 27 | 27 | 20 | 81.6 | 90.2 |

Multiple combinations of cutoffs for the CDKN2A, RREB1, MYC, and ZNF217 FISH parameters listed below yielded at least about 80% sensitivity and at least about 90% specificity (as defined by target performance):

CDKN2A % homozygous deletion of about 20 to about 30,
RREB1% gain of about 27 to about 33,
MYC % gain of about 14 to about 33, and
ZNF217% gain of about 24 to about 33.

The specific cutoff combinations that defined the lowest and the highest performance within the acceptable range around the selected cutoff of about 27%, such as the selected cutoff of 27%, for each probe are shown in Table 12.

TABLE 12

Cutoff Range Combinations for CDKN2A, RREB1, MYC, and ZNF217

| Parameter | Cutoff CDKN2A % homozygous | Cutoff RREB1 % gain | Cutoff MYC % gain | Cutoff ZNF217 % gain | Sensitivity (%) | Specificity (%) |
|---|---|---|---|---|---|---|
| Upper Range of Cutoff | 30 | 33 | 33 | 33 | 81.6 | 94.1 |
| Chosen Cutoff | 27 | 27 | 27 | 27 | 81.6 | 90.2 |
| Lower Range of Cutoff | 27 | 27 | 27 | 27 | 81.6 | 90.2 |

Example 3

This example describes the evaluation of RREB1, CCND1, CDKN2A and MYC in the prognosis of metastasis in patients with atypical Spitz tumors.

Following approval from the Northwestern University Lurie Cancer Center and the Northwestern University Internal Review Board (IRB) as well as the Institutional review boards of Memorial Sloan Kettering, University of Pennsylvania, MD Anderson, University of Michigan and the Melanoma Institute Australia, a total of 75 cases were identified that met inclusion criteria. This included a diagnosis of atypical Spitz tumor by the submitting pathologist. All cases were then reviewed by a minimum of three experienced dermatopathologists, who agreed with the diagnosis. Histologic features used to qualify a lesion as an atypical Spitz tumor included, but were not limited to, greater than typical nuclear atypia, expansile nodular or sheet-like growth, frequent, deep or atypical mitoses, lack of maturation, epidermal consumption or ulceration or necrosis, large size (>1 cm), or deep extension into the subcutaneous fat. Additionally, all cases had either of a minimum of five years of follow-up without evidence of tumor spread beyond a sentinel node or shorter follow-up time if the case had evidence of tumor spread beyond a sentinel lymph node resulting in advanced locoregional metastasis or distant metastasis and death. Seventy-five cases meeting inclusion criteria were identified. Clinical and histologic parameters were obtained for all 75 cases, including all seven important prognosticators for melanoma identified by the American Joint Committee on Cancer (AJCC) melanoma taskforce (Balch et al., J. Clin. Oncol. 27: 6199-6206 (2009)): primary tumor anatomic site, sex, age, ulceration status, mitotic rate, Breslow depth and Clark level. Also obtained for all cases were epidermal consumption, expansile nodular growth, presence of Kamino bodies and cytomorphology (predominantly epithelioid, spindled or both). The term "epidermal consumption" is used herein to refer to a process by which the epidermis is significantly thinned with loss of the rete ridge pattern often accompanied by squamitization of the basal layer and clefting, all as a result of closely opposed underlying expansile growth of melanocytes. Cases were classified into four groups by their outcome. Group 1 had three categories, namely 1x, 1a and 1b. Cases with no evidence of disease after re-excision but without sentinel lymph node biopsy performed were 1x. Those cases with no evidence of disease after re-excision and a negative sentinel lymph node were 1a, and those with positive sentinel lymph node were 1b. Those patients with locoregional disease beyond microscopic involvement of a sentinel lymph node but without distant metastasis were classified as group 2. This included patients with clinically palpable lymphadenopathy, tumor present in non-sentinel lymph nodes upon complete dissection and in-transit metastasis. Group 3 was patients with distant metastasis, and group 4 was patients with distant metastasis and death of disease. The group status of each patient is listed in Table 13, and more detailed clinical history is provided in Table 14.

TABLE 13

Summary of Clinical, Histological, and Molecular Data by Clinical Stage

| Clinical Stage | N | Average Age (y) | Sex Ratio (M:F:NA) | Average Breslow (mm) | Ulceration Status (Y:N) | Average Mitotic Rate (/mm$^2$) | Average Clark Level | % Patients with Positive FISH | Average FU Time (mo) |
|---|---|---|---|---|---|---|---|---|---|
| 1 | 64 | 20.9 | 28M:31F:5NA | 2.3 | 7Y:57N | 1.7 | 3.9 | 23.4 | 97.8 |
| 1a | 6 | | | | | | | | |
| 1b | 13 | | | | | | | | |
| 1x | 45 | | | | | | | | |
| 2 | 8 | 8.4 | 3M:4F:1NA | 3.2 | 4Y:4N | 6.1 | 4.2 | 100 | 22.9 |
| 4 | 3 | 36.3 | 2M:1F | 6.6 | 1Y:2N | 2.7 | 3.7 | 100 | 64 |

FU = follow up;
NA = not available;
M = male;
F = female;
Y = yes;
N = no;
mo = month

TABLE 14

Patients with Clinical Stages 2 to 4

| Case No. | Age/Sex | Site | FISH Data | % Cells Homozygous 9p Deletion | SLN Biopsy Result | Completion Dissection | In-transit Metastasis or Satellitosis | DM | DOD | FU Time (mo) | Clinical Stage* |
|---|---|---|---|---|---|---|---|---|---|---|---|
| 7 | 8/M | Rt arm | 9p del | 90% | 2 SLN+ | 4/6+ | Y | N | N | 120 | 2 |
| 17 | 13/M | Rt shoulder | 6p gain; 11q gain; 9p del | 100% | 1 SLN+ | NA | N | Y | Y | 96 | 4 |
| 33 | 15/NA | NA | 6p gain; 6q del; 11q gain | — | not done; developed clinically palpable LN disease | NA | N | N | N | NA | 2 |
| 35 | 38/M | Lt arm | 6p gain; 6p/Cep6; 11q gain; 9p del; 8q gain | 33.33% | NA | NA | N | Y | Y | 36 | 4 |
| 36 | 2/M | Lt cheek | 6p gain | — | 2/2 SLN+ | 2 more + nodes CLN, extensively involved | N | N | N | 3 | 2 |
| 37 | 24/F | Rt cheek | 9p del | 100% | 1/1 SLN+ | 1/9+ | Y | N | N | 4 | 2 |
| 48 | 2/F | Nose | 6p gain; 11q gain; +9p | 93.33% | 1/4 SLN+ | not done | Y | N | N | 5 | 2 |
| 49 | 8/M | Rt sin | 9p del | 73.33% | 1 SLN+ | 1/8+ | N | N | N | 4 | 2 |

TABLE 14-continued

Patients with Clinical Stages 2 to 4

| Case No. | Age/Sex | Site | FISH Data | % Cells Homozygous 9p Deletion | SLN Biopsy Result | Completion Dissection | In-transit Metastasis or Satellitosis | DM | DOD | FU Time (mo) | Clinical Stage* |
|---|---|---|---|---|---|---|---|---|---|---|---|
| 50 | 58/F | Vulva | 9p del | 40% | NA | NA | N | Y | Y | 60 | 4 |
| 66 | 2/F | Rt shoulder | 9p del | 90% | 3/3 SLN + bulky LN | 5/8 LN involved | Y | N | N | 1 | 2 |
| 75 | 6/F | Neck | 11q gain; 9p del | 100% | 1 SLN+ | 8/12 + nodes CLN, clinically palpable LN disease | N | N | N | 23 | 2 |

*clinical stage 2: disease beyond SLN + no evidence of distant metastasis; clinical stage 3: distant metastasis; clinical stage 4: distant metastasis and death due to disease
CLN = lymph node;
del = deletion;
DM = distant metastasis;
DOD = died of disease;
FU = follow up;
NA = not available;
LN = lymph node;
SLN = sentinel lymph node;
Rt = right;
Lt = left;
M = male;
F = female The hybridization procedure with multi-color FISH probe sets outlined below was performed as previously described (Gerami et al., Am. J. Surg. Pathol. 33: 1146-1156 (2009)). Two separate hybridizations were performed—one using the four-probe FISH assay targeting RREB1 (6p25), MYB (6q23), CCND1 (11q13), and chromosome 6 (using Cep6) and a second utilizing the four-probe FISH assay targeting RREB1 (6p25), CDKN2A (9p21), CCND1 (11q13), and MYC (8q24) Gerami et al. (2009), supra; and Gerami et al., Am. J. Surg. Pathol. 36: 808-817 (2012)). The slides were analyzed with an epi-fluorescence microscope equipped with single band-pass filters (Abbott Molecular Inc., Des Plaines, Ill.). A trained technician with significant experience in molecular diagnostics and FISH testing and a dermatopathologist blinded to any of the clinical data or outcome of the case performed the analyses. Tumor-bearing areas were localized using the DAPI filter at low magnification. The tumor area was then thoroughly inspected for the presence of nuclei harboring abnormal copy numbers of each probe. Areas with the most significant copy number changes were selected for enumeration. Wherever possible, 3 or less abnormal areas were selected, and within each area a minimum of 10 random nuclei were analyzed under high-power (60× objective). To qualify, nuclei had to be non-overlapping and harbor sufficiently bright signals. Nuclei that showed no signals for more than two probes were not analyzed. Thirty cells were enumerated in each specimen.

Criteria for FISH positivity were as previously published for each probe set (Gerami et al. (2009), supra; and Gerami et al. (2012), supra). For the original melanoma FISH assay positive criteria were: greater than 29% of cells with more than two copies of RREB1 (6p25), or greater than 55% of cells with more copies of RREB1 (6p25) than chromosome 6 (Cep6), or greater than 38% of cells with more than two copies of CCND1 (11q13) or more than 42% of cells with less copies of MYB (6q23) compared to chromosome 6 (Cep6). For the second probe set positive criteria were: greater than 29% of enumerated cells with homozygous deletion of CDKN2A (9p21) or more than 29% of cells with more than two copies of RREB1 (6p25), MYC (8q24) or CCND1 (11q13). Also when calculating percentage of cells with copy number aberrations, cells with copy number gains judged to be the result of tetraploidy were excluded from the numerator but left in the denominator in order to avoid false positives as a result of tetraploidy (Isaac et al., "Polyploidy in Spitz Nevi: A Not Uncommon Karyotypic Abnormality Identifiable by Fluorescence In Situ Hybridization," Am. J. Dermatopathol. 32(2): 144-148 (2010)). Cases were considered FISH-positive if any single criterion from either probe set was positive. Fisher exact test was used to compare the frequency of FISH positivity in cases from group 1 versus cases from group 2 through 4. The same analysis was also performed comparing groups 1, 2, and 3 versus 4. Fisher exact test was also used to examine the frequency of positivity for each individual probe in group 1 versus group 2-4 and p-values were calculated. Logistic regression analysis was also used to evaluate the p-value when comparing group 1 versus group 2 through 4 for all of the obtained variables including all of the AJCC-validated melanoma prognostic factors: primary tumor anatomic site, sex, age, Breslow depth, Clark level, ulceration status, and mitotic rate, as well as other histologic features, such as epidermal consumption, presence of Kamino bodies, expansile nodular growth, and cytomorphology. Multivariate analysis was performed utilizing all variables with significant ($p<0.05$) associations on univariate analysis.

A total of 75 atypical Spitz tumors with known clinical follow-up from 75 patients was analyzed using the two probe sets. The patients' ages ranged from two to 58 years with an average age of 20. Among the 75 patients, 11 had evidence of tumor spread beyond a sentinel lymph node and in three of these cases the patients developed distant metastasis and death (group 4) (Table 14). There were eight patients without distant metastasis but with disease beyond a sentinel lymph node. This included four patients with in-transit metastasis and tumor within the sentinel lymph node. Three of four of these sentinel node-positive patients also had tumor within non-sentinel nodes upon completion lymphadenectomy while one patient of two years of age did not undergo completion dissection. Among the remaining four patients without in-transit disease, three had positive sentinel nodes and further tumor detected in non-sentinel nodes upon completion dissection and two developed grossly palpable lymph node disease (Table 14). All 11 patients with advanced locoregional disease, distant metastasis or death (in groups 2-4) had a positive FISH result with copy number aberrations in at least one of the loci tested (Table 14). Among the remaining 64 cases, 15 (23.4%) had a positive FISH result. The p-value comparing the frequency of FISH positivity in group 1 versus groups 2-4 by Fisher exact test was <0.0001.

All three patients who died of disease and six of eight patients with advanced locoregional disease beyond the sentinel lymph node had evidence of homozygous deletion of CDKN2A (9p21) (Table 14). Among the nine patients who died of disease or had advanced locoregional disease and had a percentage of cells with homozygous CDKN2A (9p21) deletion above the cut-off for a positive FISH result, the average number of enumerated cells with homozygous CDKN2A (9p21) deletion was 80%. Conversely, only three of the remaining 64 patients with benign follow-up after five years had evidence of homozygous deletions of CDKN2A (9p21). In comparing the frequency of homozygous CDKN2A (9p21) deletion in group 1 versus groups 2 and 4 with a Fisher exact test, the p-value was highly significant at <0.0001. In evaluating the frequency of positivity of each of the individual probe parameters for RREB1 (6p25) gain, MYB (6q23)/chromosome 6 (Cep6) loss, RREB1 (6p25)/chromosome 6 (Cep6) gain, CCND1 (11q13) gain, CDKN2A (9p21) homozygous loss and MYC (8q24) gain using previously determined cut-offs in group 1 versus groups 2 and 4, statistical significance was found for RREB1 (6p25), CCND1 (11q13), and CDKN2A (9p21) with p-values of 0.02, 0.02 and <0.0001, respectively (Table 15).

cally significance associations with tumor progression beyond the sentinel lymph nodes. Furthermore, only CDKN2A (9p21) homozygous deletions showed a statistically significant association with death of disease (p=0.01) (Table 16).

TABLE 16

Multivariate Analysis Using Logistic Regression Model Evaluating All Prognostic Parameters Listed Below Relative to Patient Outcome

| Outcome Group | Variable | Estimate | OR | 95% CI for OR | P |
|---|---|---|---|---|---|
| Logistic regression model using 1a/1b/1x vs. 2/4 patient outcome as response | Mitotic | 0.33 | 1.40 | 1.04-1.87 | 0.03 |
|  | F9P (+ vs. −) | 2.06 | 61.51 | 8.41-449.9 | <0.0001 |
| Logistic regression model using 1a/1b/1x/2 vs. 4 patient outcome as response | F9P (+ vs. −) | 1.92 | 46.79 | 2.15-999 | 0.01 |

*Backward elimination method was used to derive the final multivariable models.
^Parameters included age, sex, site of disease, Breslow depth, mitotic rate, Clark level, ulceration status, Kamino bodies, consumption of epidermis, cytomorphology, and expansile nodules.
^^Note that only individual FISH probes, together with patient demographic and disease factors, were considered in the logistic regression models. No composite FISH outcomes were included in the logistic regression models.
CI = confidence interval;
OR = odds ratio Significantly, among the subset of six atypical Spitz tumors with isolated MYB (6q23) loss none developed advanced locoregional disease, distant metastasis, or death

TABLE 15

Comparison of Frequency of Chromosomal Copy Number Aberration by Outcome Group

|  | Group 1 vs. 2 and 4 | | | Groups 1 and 2 vs. 4 | | |
|---|---|---|---|---|---|---|
| FISH (No. +/No. −) | Group 1a/1b/1x | Group 2/4 | Fisher Exact Test | Group 1a/1b/1x/2 | Group 4 | Fisher Exact Test |
| 6p25 | 8/56 | 5/6 | 0.02 | 11/61 | 2/1 | 0.08 |
| 6q23 | 8/56 | 1/10 | 1.00 | 9/63 | 0/3 | 1.00 |
| 6p/Cep6 | 2/62 | 1/10 | 0.38 | 2/70 | 1/2 | 0.12 |
| 11q13 | 8/56 | 5/6 | 0.02 | 11/61 | 2/1 | 0.08 |
| 9p21 | 3/61 | 9/2 | <0.0001 | 9/63 | 3/0 | 0.003 |
| 8q24 | 1/63 | 1/10 | 0.27 | 1/71 | 1/2 | 0.08 |
| FISH + probe set 1 or 2* | 15/49 | 11/0 | <0.0001 | 23/49 | 3/0 | 0.04 |
| FISH + probe set 1^ | 15/49 | 6/5 | 0.06 | 19/53 | 2/1 | 0.19 |
| FISH + probe set 2^^ | 9/55 | 11/0 | <0.0001 | 17/55 | 3/0 | 0.02 |
| Cytogenetic risk§ (no. low/no. intermediate/no. high) | 55/6/3 | 0/2/9 | <0.0001 | 55/8/9 | 0/0/3 | 0.004 |

*FISH overall positivity (probe set 1 or 2) is defined as any of the individual FISH probes being positive.
^FISH probe set 1: 6p, 6p CEP 6, 6q, 11q
^^FISH probe set 2: 6p, 9p, 11q, 8q
§cytogenetic high risk: 9p positive; cytogenetic intermediate risk: 9p negative and (6p or 11q) positive; cytogenetic low risk: 9p and 6p and 11q negative In multivariate logistic regression analysis analyzing each individual FISH parameter and all the AJCC prognostic parameters including age, sex, primary tumor site, ulceration status, Breslow depth, Clark level, and mitotic rate, as well as other factors frequently assessed in Spitz tumors, such as presence or absence of epidermal consumption, Kamino bodies, expansile nodular growth, and epithelioid versus spindle morphology, only mitotic rate (p=0.03) and homozygous CDKN2A (9p21) deletion (p<0.0001) showed statistiwith follow-up duration ranging from 60 to 96 months. Four of these six patients did have a sentinel node biopsy, and all four patients had tumor within the sentinel lymph nodes. There were no atypical Spitz tumors with a negative FISH result by all of the probe parameters resulting in advanced local regional disease, distant metastasis, or death.

This study demonstrates that the presence of specific chromosomal aberrations, such as gain in RREB1 (6p25) or CCND1 (11q13) and homozygous loss of CDKN2A (9p21)

clearly identifies melanocytic tumors with a higher likelihood for aggressive behavior. Additionally, logistic regression analysis and multivariate analysis of the individual probe parameters provides compelling evidence that not all copy number aberrations among intermediate grade melanocytic tumors have equal value. Specifically, homozygous deletions at CDKN2A (9p21) were highly significant in their correlation with an aggressive disease course with nine of 11 patients with tumor extending beyond the sentinel lymph node showing evidence of homozygous CDKN2A (9p21) deletions. Also significant was that the average percentage of enumerated cells showing homozygous deletions within this group of nine patients was 80%. Hence although the cut-off threshold for a positive result determined in unequivocally benign and malignant tumors is >29% of cells having homozygous deletion, when evaluating atypical Spitz tumors in clinical practice a truly significant result is likely to be fairly dramatic and to have a significantly higher percentage of cells with homozygous CDKN2A (9p21) deletions.

Among the 75 atypical Spitz tumor patients in the study, 12 had homozygous CDKN2A (9p21) deletions above the predetermined cut-off value. Of these 12 patients, nine developed advanced locoregional disease, distant metastasis or death. Three of these patients had distant metastasis and death of disease. The p-value by Fisher exact test comparing the frequency of homozygous CDKN2A (9p21) deletions in the aggressive versus non-aggressive behaving group was <0.0001.

Interestingly, four patients (three children and one adult, cases 7, 37, 48, and 66 from Table 14, respectively) all from separate institutions showed a markedly similar course involving the presence of an atypical Spitzoid melanocytic neoplasm with many homozygous CDKN2A (9p21) deletions and persistent in-transit disease/satellitosis around the primary tumor site with four of four cases also showing involvement of sentinel lymph nodes. Three of these four patients had completion dissection and all three had evidence of tumor involvement of non-sentinel lymph nodes as well. Hence we propose the term "Spitzoid melanoma with homozygous CDKN2A (9p21) deletion" to describe this subtype of melanoma, which is likely of a lower grade than conventional melanoma, is more frequently seen in children than in adults, has spitzoid cytomorphology with homozygous CDKN2A (9p21) deletions in the vast majority of cells, frequently results in transit metastasis, and often has lymph node involvement including non-sentinel lymph nodes. Patient 7 has over eight years of clinical follow-up and remains disease-free following surgery and treatment with interferon. The remaining three patients have more limited follow-up time. Further follow-up studies of these patients are needed to determine the likelihood, frequency and time to development of distant metastasis and death.

Copy number gains in 6p25 and 11q13 were both statistically significantly more frequently seen in the aggressive group of atypical Spitz tumors with a p-value of 0.02 for both parameters. This suggests that atypical Spitzoid melanocytic tumors with these changes should be considered of higher risk for aggressive behavior compared to those which are FISH-negative, but less so than cases with homozygous CDKN2A (9p21) deletions. Provisionally, the term "Spitzoid melanoma with RREB1 (6p25) gain or CCND1 (11q13) gain" could be utilized with the understanding that the latter two are of considerably lower risk than cases with homozygous CDKN2A (9p21) deletions.

None of the six atypical Spitz tumors with isolated MYB (6q23) loss showed evidence of advanced local-regional disease, distant metastasis, or death despite a minimum of five years of follow-up. Hence, in the setting of an atypical Spitz tumor in which the FISH shows isolated losses of MYB (6q23), we suggest refraining from a diagnosis of melanoma and at least provisionally referring to this as "atypical Spitz tumor with MYB (6q23) deletion." This appears to be a subset of Spitzoid melanocytic neoplasms that frequently results in a positive sentinel lymph node biopsy but only infrequently progresses beyond this, although the data are limited and further follow-up studies are necessary. Regarding MYC (8q24), which has been shown to have a clearly significant prognostic effect in conventional melanomas (Gerami et al., J. Mol. Diagn. 13: 352-358 (2011)), there were too few cases positive in this study to have statistical significance. This is not surprising since we previously showed that 8q24 is most typical of amelanotic nodular or nevoid melanomas (Pouryazdanparast et al., Am. J. Surg. Pathol. 36: 253-264 (2012); Pouryazdanparast et al., "The Role of 8q24 Copy Number Gains and c-MYC Expression in Amelanotic Cutaneous Melanoma," Mod. Pathol. 25(9): 1221-1226 (2012)) but is an infrequent copy number aberration in Spitzoid neoplasms.

In summary, gains in RREB1 (6p25) or CCND1 (11q13) and homozygous deletions in CDKN2A (9p21) had statistically significant association with aggressive clinical behavior with p-values of 0.02, 0.02 and <0.0001, respectively. In multivariate analysis homozygous CDKN2A (9p21) deletion was highly associated with clinically aggressive behavior (p<0.0001) and death of disease (p=0.003). Cases with homozygous CDKN2A (9p21) deletions have the greatest risk to develop advanced loco-regional disease and even distant metastases and death. Cases with RREB1 (6p25) or CCND1 (11q13) gains also have higher risk for aggressive clinical behavior than FISH negative atypical Spitz tumors or cases with MYB (6q23) deletions. Thus, FISH detecting a limited number of chromosomal copy number aberrations can provide clinically useful and statistically significant risk assessment for atypical Spitz tumors.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. A method comprising:
   (a) contacting a Spitz tumor sample obtained from a human patient with a set of detectably labeled probes, wherein the set consists of:
      (i) a probe which hybridizes to the RREB1 gene on chromosome 6p25,
      (ii) a probe which hybridizes to the CDKN2A gene on chromosome 9p21,
      (iii) a probe which hybridizes to the CCND1 gene on chromosome 11q13, and
      (iv) a probe which hybridizes to the MYC gene on chromosome 8q24; and
   (b) detecting an increase in copy number of the RREB1, CCND1, and MYC genes and a homozygous deletion of the CDKN2A gene in the Spitz tumor sample using fluorescence in situ hybridization.

* * * * *